US009353420B2

(12) United States Patent
Lee

(10) Patent No.: US 9,353,420 B2

(45) Date of Patent: *May 31, 2016

(54) METHOD TO PREDICT OR DIAGNOSE A GASTOINTESTINAL DISORDER OR DISEASE

(71) Applicant: Nancy M. Lee, San Francisco, CA (US)

(72) Inventor: Nancy M. Lee, San Francisco, CA (US)

(73) Assignee: Nancy M. Lee, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/536,305

(22) Filed: Nov. 7, 2014

(65) Prior Publication Data

US 2015/0275311 A1 Oct. 1, 2015

Related U.S. Application Data

(63) Continuation of application No. 12/670,854, filed as application No. PCT/US2008/071090 on Jul. 25, 2008, now Pat. No. 8,883,440.

(60) Provisional application No. 60/952,194, filed on Jul. 26, 2007.

(51) Int. Cl.
*C12Q 1/68* (2006.01)
*A61B 1/31* (2006.01)

(52) U.S. Cl.
CPC ................ *C12Q 1/6886* (2013.01); *A61B 1/31* (2013.01); *C12Q 1/6841* (2013.01); *C12Q 2600/112* (2013.01); *C12Q 2600/158* (2013.01); *C12Q 2600/16* (2013.01)

(58) Field of Classification Search
CPC .................................................... C12Q 1/6841
See application file for complete search history.

(56) References Cited

U.S. PATENT DOCUMENTS 5,741,650 A 4/1998 Lapidus
5,837,452 A 11/1998 Clark
5,952,178 A 9/1999 Lapidus
6,025,336 A 2/2000 Goultry et al.
6,268,136 B1 7/2001 Shuber
6,303,304 B1 10/2001 Shuber
6,406,857 B1 6/2002 Shuber
6,423,491 B1 7/2002 Howe
6,586,177 B1 7/2003 Shuber
6,919,174 B1 7/2005 Shuber
6,964,846 B1 11/2005 Shuber
2001/0051344 A1 12/2001 Shalon et al.
2002/0119472 A1 8/2002 Lapidus
2002/0164631 A1 11/2002 Shuber
2004/0014104 A1 1/2004 Shuber
2004/0043467 A1 3/2004 Shuber
2004/0241710 A1 12/2004 Gish
2004/0259101 A1 12/2004 Shuber
2005/0014165 A1 1/2005 Lee et al.
2005/0260638 A1 11/2005 Shuber
2006/0088862 A1 4/2006 Lee
2006/0121495 A1 6/2006 Shuber
2008/0085524 A1 4/2008 Augusto
2008/0166719 A1 7/2008 Augusto

FOREIGN PATENT DOCUMENTS

JP 2005080524 A 3/2005
WO WO03078662 A1 9/2003

OTHER PUBLICATIONS

Mandel et al. The New England J of Medicine, 1993, 328(19):1365-1371.*

Ahern et al., "Biochemical, reagents kits offer scientists good return on investment." The Scientist, vol. 9, Issue 15, p. 20, Jul. 1995.

Bamba, H., et al., "High expression of cyclooxygenase-2 in macrophages fo human colonic adenorna," Int. J. Cancer, 83:470-475, 1999.

Barrier, Alain et al., Dis. Colon Rectum, 48:2238-2248, 2005.

Barrier, Alain et al., Oncogene, 24:6155-164, 2005.

Bernstein, Carol et al., Cancer Research, 59:2353-2357, 1999.

Bianchi et al., "The urokinase receptor is expressed in invasive breast cancer but not in normal breast tissue." Cancer Res. 54:861-866, 1994.

Buck et al., "Design Strategies and Performance of Custom DNA Sequencing Primers," Biotechniques, vol. 27, pp. 528-536, Sep. 1999.

Buckhaults et al., "Secreted and cell surface genes expressed in benign and malignant colorectal tumors." Cancer Res., 61:6996-7001, 2001.

Carlson M. et al., Gut, 50:501-506, 2002.

Chen Ling-Chun et al., Cancer Research, 64:3694-3700, 2004.

Chen, G. et al., "Discordant Protein and mRNA Expression in Lung Adenocarcinoma," Molecular and Cellular Proteomics, vol. 1, pp. 304-313, 2002.

Clark et al., "Gene expression profiling of human colon cancer cells following inhibition of signal transduction by 1-allylamioo-17-demethoxygeldanamycin, an nhibitor of the hsp90 molecular chaperone." Oncogene, vol. 19, pp, 4125-4133, 2000.

Clark et al., "gene expression microarray analysis in cancer biology, pharmacology and drug development: progress and potential." Biochemical Pharmacology, vol. 62, pp. 1311-1336, 2001.

Coussens and Werb, Inflammation and Cancer, Nature, 420:860-867, 2002.

Denhardt et al., "Osteopontin as a means to cope with environmental insults: regulation of inflammation, tissue remodeling and cell survival," J. Clin. Invest, 107:1055-1061, 2001.

De Villiers, et al., Cytokine, vol. 12, No. 9. pp. 1337-1347, 2000.

Dolara et al., Toxicology Letters, vol. 112-113, pp. 415-420, 2000.

Eberhart et al., "Up-regulation of cyclooxygense 2 gene expression in human colorectal adenomas and adenocarcinomas," Gastroenterology, vol. 107, pp. 1183-1188, 1994.

(Continued)

*Primary Examiner* — Bin Shen

(74) *Attorney, Agent, or Firm* — Joseph R. Baker, Jr.; Gavrilovich, Dodd & Lindsey LLP

(57) ABSTRACT

The disclosure provides methods and compositions useful for identifying a subject's predisposition to a gastrointestinal disease or disorder.

18 Claims, 5 Drawing Sheets

(56) References Cited

OTHER PUBLICATIONS

Feng et al., Pharmacogenomics, vol. 5, pp, 709-719, 2004.
Frank et al., Nature Rev. vol. 2, pp. 566-580, 2003.
Friedl, A. et al., The Histochemical Journal, vol. 31, pp. 433-441, 1999.
Fukushima K., et al., Digestive Diseases and Sciences, vol. 47, No. 7, pp. 1438-1446, 2002.
Futschik et al., "Gene Expression Profiling of Metastatic and Nonmetastatic Colorectal Cancer Cell Lines," Genome Letters, vol. 1, No. 1, pp. 22-34, 2002.
GeneBank accession No. M94582 (online), publicly available Apr. 27, 1993 (retrieved on Jul. 12, 2007), retrieved from the internet <url: ww.ncbi.nlm.nih.gov/entrez/viewer.fcgidb=nucleotide&val-186377>.
GeneBank accession No. NM_006238 (online), publicly available Jul. 13, 1999 (retrived on Jul. 12, 2007), retrieved from the internet <url: ww.ncbi.nlm.nih.gov/entrez/viewer..fcgi?543939:OLD02:501339>.
GenBank Accession No. M23698, GI: 758678, publicly available Apr. 1994.
Giordano, et al, "Organ-specific molecular classification of primary lung, colon, and ovarian adenocarcinomas using gene expression profiles." Am. J. Pathol, vol. 159, pp. 1231-1238, 2001.
Golub et al., "Molecular classificaiton of cancer: class discovery and class prediction by gene expression monitoring," Science Biol. vol. 286, pp. 531-537, Oct. 1999.
Gould et al., "BMP-7 regulates chemokine, cytokine and hemodynamic gene expression in proximal tubule cells," Kidney International vol. 61, pp. 51-60, Jan. 2002.
Guda et al., "Multistage gene expression profiling in a differentially susceptible mouse colon cancer model," Cancer Letter, vol. 191. pp. 17-25, 2003.
Gupta et al., "Aspriin, NSAIDS, and colon cancer prevention: mechanisms?" Gastroenterology, vol. 114, pp. 1094-1098, 1998.
Hao et al., Clinical Cancer Research, vol. 11, pp. 1400-1407, 2005.
Hao et al., Dis. Colon Rectum, vol. 48, pp. 2329-2335, 2005.
He et al., "Identification of c-MYC as a targe fo teh APC pathway," Science, vol. 281, pp. 1509-1512, 1998.
Hedge et al., "Identification of tumor markers in models of human colorectal cancer using a 19,200-element complementary DNA microarray," Cancer Res, vol. 61, pp. 7792-7792, 2001.
Hull et al., "Cyclooxygenase 2 is up-regulated and localized to macrophages in the intestine of Min mice," Br. J. Cancer, vol. 79, pp. 1399-1405, 1999.
Ieda et al., "Immunohistochemical analysis of p53 and ras p71 expression in colorectal adenomas and early carcinomas," Surg. Today, vol. 26: pp. 230-235, 1996.
Inaba et al., "Induction of cyclooxygenase 2 in mortocyte/macrophage by mucins secreted from colon cancer cells," Proc. Natl. Ada. Sci. U.S.A., vol. 100, pp. 2736-2741, 2003.
Kitahara et al., "Aleterations of gene expression during colorectal carcinogenesis revealed by cDNA microarrays after laser-capture microdissection of tumor tissues and normal epithelia," Cancer Res., vol. 61, pp. 2544-3549, 2001.
Koh et al., "Gastrin is a target of the beta-catenin/TCF-4 Growth-signaling pathway in a model of intestinal polyposis," J. Clin Invest. vol. 106, pp. 533-539, 2000.
Korfhage et al,. "Critical Factors for Successful Microarray and Real-Time Analyses," R&D Department, Qiagen GmbH, Holden German, Issue No. 5, 2002.
Li et al., "Expression of interleukin 8 and its receptors in human colon carcinoma cells with different metastatic potentials," Clin. Cancer Res., vol. 7, pp. 3298-3304, 2001.
Lin et al. , "Identification of AF17 as a downstream gene of the beta-catenin/T-cell factor pathway and its involvement in colorectal carcinogenesis," Cancer Res. vol. 61, pp. 6345-6349, 2001.
Loukinova et al, "Growth regulated oncogene-alpha expression by murine squamous cell carcinoma promotes tumor growth, metastasis, leukocyte infiltration and angiogenesis by a host CXC receptor-2 dependent mechanism," Oncogene, vol. 19, pp. 2477-3486, 2000.
Lucitini J., "Gene Association Studies Typically Wrong," The Scientist, p. 20, Dec. 20, 2004.
Marnett and DuBois, "COX-2: a atarget colon cancer prevention." Annu. Rev. Pharmacol Toxicol., vol. 42, pp. 55-80, 2002.
Muller-Decker et al., "Transenic cyclooxygenase-2 overexpression sensitizes mouse skin for carcinogenesis," Proc. Natl. Mad. Sci. U.S.A., vol. 99, pp. 12483-12488, 2002.
Muro et al., "Identification of expressed genes linked to malignancy of human colorectal carcinoma by parametric clustering of quantitative expression data," Geneome Biol, vol. 4, No. R21, 2003.
Notterman et al., "Trascriptional gene expression profiles of colorectal adenoma, adenocarcinoma, and normal tissue examined by oligonucleolide arrays," Cancer Res., vol. 61, pp. 3124-3130, 2001.
Oshima et al., "Suppression of intestinal polyposis in Apc deita716 knockout mice by inhibition of cyclooxygenase 2 (COX-2)," Cell, vol. 87, pp. 803-809, 1996.
Paulsen et al., "Qualitative and quantitative relationship between dyspiastic aberrant crypt foci and tumorigenesis in the Min/+ mouse colon," Cancer Res., vol. 61, pp. 5010-5015, 2001.
Pusztai and Hess, "Clinical trial design for microarray predictive marker discovery and assessment," Annals of Oncology, vol. 15, pp. 1731-1737, 2004.
Qiagen News, Issue 2, pp. 11-13, 1998.
Qiagen News, Issue 5, "RNAlater Tissue Protect Tubes," p. 21, 2002.
Roy et al., "Distal bowel selectivity in the chemopevention fo experimental colon carcinogenesis by the non-steroidal antiinflammatory drug nabumetone," Int. J. Cancer, vol. 92, p. 609-615, 2001.
Sherr, "The Pezcoller lecture: cancer cell cycles revisited," Cancer Res., vol. 60, pp. 3689-3695, 2000.
Siu et al, "The identification of monoclonality in human aberrant crypt foci," Cancer Res., vol. 59, pp. 63-66, 1999.
Stratagene Catalog, 1998, p. 39, "Gene characterization kits".
TaqMan (R) EZ RT-PCR kit protocol, Applied Biosystems, Printed in the USA, Apr. 2002.
Tureci et al., "Comoutational dissection of tissue contamination for identification of colon cancer-specific expression profiles," Faseb J, vol. 17, pp. 376-385, 2003.
Wagner, Dis. Markers, vol. 18, pp. 41-46, 2002.
Williams et al, "Identification and validation of gene involved in the pathogenesis of colorectal cancer using cDNA microarrays and RNA interference," Clin. Cancer Res., vol. 9, pp. 931-946, 2003.
Wu T.D., "Analysing Gene Expression Data from DNA Microarrays to Identify Candidate Genes," J. Pathol., vol. 195, No. 1, pp. 53-65, 2001.
Zou et al., Oncogene, vol. 21 No. 4855-4862, 2002.
Berghella et al., "Peripheral Blood Immunological Parameters for Use as Marker of Pre-invasive to Invasive Colorectal Cancer," Cancer Biotherapy & RadioPharm., vol. 17, No. 1, pp. 43-51, 2002.
Berghella et al., "Prognostic Significance of Immunological Evaluation in Colorecta Cancer," Cancer Biotherapy & Radiopharm., vol. 11, No. 6, pp. 355-362, 1996.
Grotowski et al., "Comparison of CA19-9, IL-6, IL-8, bFGF, sTNF RI, sTNF RII and sIL-2R in serum of colorectal cancer patients," Int. Rev. Alergol. Clin. Immunol. vol. 8, No. 4, pp. 225-232, 2002.
Manavi et al., "Detection of hepatitis C virus (HVC) RNA in normal cervical smears of HCV-seropositive patients", CID, 2002, 35:966-973.
Rall et al., "CD44 Isoform expression in primary and metastatic pancreatic adenocarcinoma", Cancer Research, 1995, 55:1831-1835.
Martin et al., "High-sensitivity array analysis of gene expression for the early detection of disseminated breast tumor cells in perpheral blood", PNAS, 2001, 98(5):2646-2651.
Spivack et al., "Gene-enviornment interaction signatures by quantitative mRNA profling in exfoliated buccal mucosal cells", Cancer Research, 2004, 64;6805-6813.

* cited by examiner

SEQUENCE LISTING

```
<160> NUMBER OF SEQ ID NOS: 88

<210> SEQ ID NO 1
<211> LENGTH: 1666
<212> TYPE: DNA
<213> ORGANISM: homo sapiens
<220> FEATURE:
```

```
<221> NAME/KEY: CDS
<222> LOCATION: (102)..(401)

<400> SEQUENCE: 1

ctccataagg cacaaacttt cagagacagc agagcacaca agcttctagg acaagagcca      60

ggaagaaacc accggaagga accatctcac tgtgtgtaaa c atg act tcc aag ctg    116
                                              Met Thr Ser Lys Leu
                                              1               5

gcc gtg gct ctc ttg gca gcc ttc ctg att tct gca gct ctg tgt gaa      164
Ala Val Ala Leu Leu Ala Ala Phe Leu Ile Ser Ala Ala Leu Cys Glu
                10                  15                  20

ggt gca gtt ttg cca agg agt gct aaa gaa ctt aga tgt cag tgc ata      212
Gly Ala Val Leu Pro Arg Ser Ala Lys Glu Leu Arg Cys Gln Cys Ile
            25                  30                  35

aag aca tac tcc aaa cct ttc cac ccc aaa ttt atc aaa gaa ctg aga      260
Lys Thr Tyr Ser Lys Pro Phe His Pro Lys Phe Ile Lys Glu Leu Arg
        40                  45                  50

gtg att gag agt gga cca cac tgc gcc aac aca gaa att att gta aag      308
Val Ile Glu Ser Gly Pro His Cys Ala Asn Thr Glu Ile Ile Val Lys
    55                  60                  65

ctt tct gat gga aga gag ctc tgt ctg gac ccc aag gaa aac tgg gtg      356
Leu Ser Asp Gly Arg Glu Leu Cys Leu Asp Pro Lys Glu Asn Trp Val
70                  75                  80                  85

cag agg gtt gtg gag aag ttt ttg aag agg gct gag aat tca taa          401
Gln Arg Val Val Glu Lys Phe Leu Lys Arg Ala Glu Asn Ser
                90                  95

aaaaattcat tctctgtggt atccaagaat cagtgaagat gccagtgaaa cttcaagcaa    461

atctacttca acacttcatg tattgtgtgg gtctgttgta gggttgccag atgcaataca    521

agattcctgg ttaaatttga atttcagtaa acaatgaata gtttttcatt gtaccatgaa    581

atatccagaa catacttata tgtaaagtat tatttatttg aatctacaaa aaacaacaaa    641

taatttttaa atataaggat tttcctagat attgcacggg agaatataca aatagcaaaa    701

ttgaggccaa gggccaagag aatatccgaa ctttaatttc aggaattgaa tgggtttgct    761

agaatgtgat atttgaagca tcacataaaa atgatgggac aataaatttt gccataaagt    821

caaatttagc tggaaatcct ggattttttt ctgttaaatc tggcaaccct agtctgctag    881

ccaggatcca caagtccttg ttccactgtg ccttggtttc tcctttattt ctaagtggaa    941

aaagtattag ccaccatctt acctcacagt gatgttgtga ggacatgtgg aagcacttta   1001

agtttttttca tcataacata aattattttc aagtgtaact tattaaccta tttattattt  1061

atgtatttat ttaagcatca aatatttgtg caagaatttg gaaaaataga agatgaatca   1121

ttgattgaat agttataaag atgttatagt aaatttattt tattttagat attaaatgat   1181

gttttattag ataaatttca atcagggttt ttagattaaa caaacaaaca attgggtacc   1241

cagttaaatt ttcatttcag ataaacaaca aataattttt tagtataagt acattattgt   1301

ttatctgaaa ttttaattga actaacaatc ctagtttgat actcccagtc ttgtcattgc   1361

cagctgtgtt ggtagtgctg tgttgaatta cggaataatg agttagaact attaaaacag   1421

ccaaaactcc acagtcaata ttagtaattt cttgctggtt gaaacttgtt tattatgtac   1481

aaatagattc ttataatatt atttaaatga ctgcattttt aaatacaagg ctttatattt   1541

ttaactttaa gatgttttta tgtgctctcc aaattttttt tactgtttct gattgtatgg   1601

aaatataaaa gtaaatatga aacatttaaa atataatttg ttgtcaaagt aaaaaaaaaa   1661

aaaaa                                                                1666
```

```
<210> SEQ ID NO 2
<211> LENGTH: 99
<212> TYPE: PRT
<213> ORGANISM: homo sapiens

<400> SEQUENCE: 2

Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
        35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser


<210> SEQ ID NO 3
<211> LENGTH: 2098
<212> TYPE: DNA
<213> ORGANISM: homo sapiens
<220> FEATURE:
<221> NAME/KEY: CDS
<222> LOCATION: (79)..(573)

<400> SEQUENCE: 3

cctgccgaag tcagttcctt gtggagccgg agctgggcgc ggattcgccg aggcaccgag      60

gcactcagag gaggcgcc atg tca gaa ccg gct ggg gat gtc cgt cag aac      111
                    Met Ser Glu Pro Ala Gly Asp Val Arg Gln Asn
                    1               5                   10

cca tgc ggc agc aag gcc tgc cgc cgc ctc ttc ggc cca gtg gac agc      159
Pro Cys Gly Ser Lys Ala Cys Arg Arg Leu Phe Gly Pro Val Asp Ser
            15                  20                  25

gag cag ctg agc cgc gac tgt gat gcg cta atg gcg ggc tgc atc cag      207
Glu Gln Leu Ser Arg Asp Cys Asp Ala Leu Met Ala Gly Cys Ile Gln
        30                  35                  40

gag gcc cgt gag cga tgg aac ttc gac ttt gtc acc gag aca cca ctg      255
Glu Ala Arg Glu Arg Trp Asn Phe Asp Phe Val Thr Glu Thr Pro Leu
    45                  50                  55

gag ggt gac ttc gcc tgg gag cgt gtg cgg ggc ctt ggc ctg ccc aag      303
Glu Gly Asp Phe Ala Trp Glu Arg Val Arg Gly Leu Gly Leu Pro Lys
60                  65                  70                  75

ctc tac ctt ccc acg ggg ccc cgg cga ggc cgg gat gag ttg gga gga      351
Leu Tyr Leu Pro Thr Gly Pro Arg Arg Gly Arg Asp Glu Leu Gly Gly
                80                  85                  90

ggc agg cgg cct ggc acc tca cct gct ctg ctg cag ggg aca gca gag      399
Gly Arg Arg Pro Gly Thr Ser Pro Ala Leu Leu Gln Gly Thr Ala Glu
            95                  100                 105

gaa gac cat gtg gac ctg tca ctg tct tgt acc ctt gtg cct cgc tca      447
Glu Asp His Val Asp Leu Ser Leu Ser Cys Thr Leu Val Pro Arg Ser
        110                 115                 120

ggg gag cag gct gaa ggg tcc cca ggt gga cct gga gac tct cag ggt      495
Gly Glu Gln Ala Glu Gly Ser Pro Gly Gly Pro Gly Asp Ser Gln Gly
    125                 130                 135

cga aaa cgg cgg cag acc agc atg aca gat ttc tac cac tcc aaa cgc      543
Arg Lys Arg Arg Gln Thr Ser Met Thr Asp Phe Tyr His Ser Lys Arg
```

```
140                 145                 150                 155

cgg ctg atc ttc tcc aag agg aag ccc taa tccgcccaca ggaagcctgc       593
Arg Leu Ile Phe Ser Lys Arg Lys Pro
                160

agtcctggaa gcgcgagggc ctcaaaggcc cgctctacat cttctgcctt agtctcagtt    653

tgtgtgtctt aattattatt tgtgttttaa tttaaacacc tcctcatgta cataccctgg    713

ccgcccccctg ccccccagcc tctggcatta gaattattta aacaaaaact aggcggttga    773

atgagaggtt cctaagagtg ctgggcattt ttattttatg aaatactatt taaagcctcc    833

tcatcccgtg ttctcctttt cctctctccc ggaggttggg tgggccggct tcatgccagc    893

tacttcctcc tccccacttg tccgctgggt ggtaccctct ggaggggtgt ggctccttcc    953

catcgctgtc acaggcggtt atgaaattca cccccttcc tggacactca gacctgaatt   1013

ctttttcatt tgagaagtaa acagatggca ctttgaaggg gcctcaccga gtgggggcat   1073

catcaaaaac tttggagtcc cctcacctcc tctaaggttg ggcagggtga ccctgaagtg   1133

agcacagcct agggctgagc tggggacctg gtaccctcct ggctcttgat acccccctct   1193

gtcttgtgaa ggcaggggga aggtggggtc ctggagcaga ccaccccgcc tgccctcatg   1253

gcccctctga cctgcactgg ggagcccgtc tcagtgttga gccttttccc tctttggctc   1313

ccctgtacct tttgaggagc cccagctacc cttcttctcc agctgggctc tgcaattccc   1373

ctctgctgct gtccctcccc cttgtccttt cccttcagta ccctctcagc tccaggtggc   1433

tctgaggtgc ctgtcccacc cccaccccca gctcaatgga ctggaagggg aagggacaca   1493

caagaagaag ggcaccctag ttctacctca ggcagctcaa gcagcgaccg cccctcctc    1553

tagctgtggg ggtgagggtc ccatgtggtg gcacaggccc ccttgagtgg ggttatctct   1613

gtgttagggg tatatgatgg gggagtagat ctttctagga gggagacact ggcccctcaa   1673

atcgtccagc gaccttcctc atccacccca tccctcccca gttcattgca ctttgattag   1733

cagcggaaca aggagtcaga cattttaaga tggtggcagt agaggctatg gacagggcat   1793

gccacgtggg ctcatatggg gctgggagta gttgtctttc ctggcactaa cgttgagccc   1853

ctggaggcac tgaagtgctt agtgtacttg gagtattggg gtctgacccc aaacaccttc   1913

cagctcctgt aacatactgg cctggactgt ttctctcggg ctccccatgt gtcctggttc   1973

ccgtttctcc acctagactg taaacctctc gagggcaggg accacaccct gtactgttct   2033

gtgtctttca cagctcctcc cacaatgctg atatacagca ggtgctcaat aaacgattct   2093

tagtg                                                               2098


<210> SEQ ID NO 4
<211> LENGTH: 164
<212> TYPE: PRT
<213> ORGANISM: homo sapiens

<400> SEQUENCE: 4

Met Ser Glu Pro Ala Gly Asp Val Arg Gln Asn Pro Cys Gly Ser Lys
1               5                   10                  15

Ala Cys Arg Arg Leu Phe Gly Pro Val Asp Ser Glu Gln Leu Ser Arg
            20                  25                  30

Asp Cys Asp Ala Leu Met Ala Gly Cys Ile Gln Glu Ala Arg Glu Arg
        35                  40                  45

Trp Asn Phe Asp Phe Val Thr Glu Thr Pro Leu Glu Gly Asp Phe Ala
    50                  55                  60

Trp Glu Arg Val Arg Gly Leu Gly Leu Pro Lys Leu Tyr Leu Pro Thr
```

```
65                  70                  75                  80

Gly Pro Arg Arg Gly Arg Asp Glu Leu Gly Gly Gly Arg Arg Pro Gly
                85                  90                  95

Thr Ser Pro Ala Leu Leu Gln Gly Thr Ala Glu Glu Asp His Val Asp
            100                 105                 110

Leu Ser Leu Ser Cys Thr Leu Val Pro Arg Ser Gly Glu Gln Ala Glu
        115                 120                 125

Gly Ser Pro Gly Gly Pro Gly Asp Ser Gln Gly Arg Lys Arg Arg Gln
    130                 135                 140

Thr Ser Met Thr Asp Phe Tyr His Ser Lys Arg Arg Leu Ile Phe Ser
145                 150                 155                 160

Lys Arg Lys Pro


<210> SEQ ID NO 5
<211> LENGTH: 3083
<212> TYPE: DNA
<213> ORGANISM: homo sapiens
<220> FEATURE:
<221> NAME/KEY: CDS
<222> LOCATION: (162)..(2390)

<400> SEQUENCE: 5

aaaaactgca gccaacttcc gaggcagcct cattgcccag cggaccccag cctctgccag      60

gttcggtccg ccatcctcgt cccgtcctcc gccggcccct gccccgcgcc cagggatcct     120

ccagctcctt tcgcccgcgc cctccgttcg ctccggacac c atg gac aag ttt tgg     176
                                              Met Asp Lys Phe Trp
                                              1               5

tgg cac gca gcc tgg gga ctc tgc ctc gtg ccg ctg agc ctg gcg cag       224
Trp His Ala Ala Trp Gly Leu Cys Leu Val Pro Leu Ser Leu Ala Gln
                10                  15                  20

atc gat ttg aat ata acc tgc cgc ttt gca ggt gta ttc cac gtg gag       272
Ile Asp Leu Asn Ile Thr Cys Arg Phe Ala Gly Val Phe His Val Glu
            25                  30                  35

aaa aat ggt cgc tac agc atc tct cgg acg gag gcc gct gac ctc tgc       320
Lys Asn Gly Arg Tyr Ser Ile Ser Arg Thr Glu Ala Ala Asp Leu Cys
        40                  45                  50

aag gct ttc aat agc acc ttg ccc aca atg gcc cag atg gag aaa gct       368
Lys Ala Phe Asn Ser Thr Leu Pro Thr Met Ala Gln Met Glu Lys Ala
    55                  60                  65

ctg agc atc gga ttt gag acc tgc agg tat ggg ttc ata gaa ggg cac       416
Leu Ser Ile Gly Phe Glu Thr Cys Arg Tyr Gly Phe Ile Glu Gly His
70                  75                  80                  85

gtg gtg att ccc cgg atc cac ccc aac tcc atc tgt gca gca aac aac       464
Val Val Ile Pro Arg Ile His Pro Asn Ser Ile Cys Ala Ala Asn Asn
                90                  95                  100

aca ggg gtg tac atc ctc aca tcc aac acc tcc cag tat gac aca tat       512
Thr Gly Val Tyr Ile Leu Thr Ser Asn Thr Ser Gln Tyr Asp Thr Tyr
            105                 110                 115

tgc ttc aat gct tca gct cca cct gaa gaa gat tgt aca tca gtc aca       560
Cys Phe Asn Ala Ser Ala Pro Pro Glu Glu Asp Cys Thr Ser Val Thr
        120                 125                 130

gac ctg ccc aat gcc ttt gat gga cca att acc ata act att gtt aac       608
Asp Leu Pro Asn Ala Phe Asp Gly Pro Ile Thr Ile Thr Ile Val Asn
    135                 140                 145

cgt gat ggc acc cgc tat gtc cag aaa gga gaa tac aga acg aat cct       656
Arg Asp Gly Thr Arg Tyr Val Gln Lys Gly Glu Tyr Arg Thr Asn Pro
150                 155                 160                 165

gaa gac atc tac ccc agc aac cct act gat gat gac gtg agc agc ggc       704
```

-continued

```
Glu Asp Ile Tyr Pro Ser Asn Pro Thr Asp Asp Asp Val Ser Ser Gly
                170                 175                 180

tcc tcc agt gaa agg agc agc act tca gga ggt tac atc ttt tac acc      752
Ser Ser Ser Glu Arg Ser Ser Thr Ser Gly Gly Tyr Ile Phe Tyr Thr
            185                 190                 195

ttt tct act gta cac ccc atc cca gac gaa gac agt ccc tgg atc acc      800
Phe Ser Thr Val His Pro Ile Pro Asp Glu Asp Ser Pro Trp Ile Thr
        200                 205                 210

gac agc aca gac aga atc cct gct acc act ttg atg agc act agt gct      848
Asp Ser Thr Asp Arg Ile Pro Ala Thr Thr Leu Met Ser Thr Ser Ala
    215                 220                 225

aca gca act gag aca gca acc aag agg caa gaa acc tgg gat tgg ttt      896
Thr Ala Thr Glu Thr Ala Thr Lys Arg Gln Glu Thr Trp Asp Trp Phe
230                 235                 240                 245

tca tgg ttg ttt cta cca tca gag tca aag aat cat ctt cac aca aca      944
Ser Trp Leu Phe Leu Pro Ser Glu Ser Lys Asn His Leu His Thr Thr
                250                 255                 260

aca caa atg gct ggt acg tct tca aat acc atc tca gca ggc tgg gag      992
Thr Gln Met Ala Gly Thr Ser Ser Asn Thr Ile Ser Ala Gly Trp Glu
            265                 270                 275

cca aat gaa gaa aat gaa gat gaa aga gac aga cac ctc agt ttt tct     1040
Pro Asn Glu Glu Asn Glu Asp Glu Arg Asp Arg His Leu Ser Phe Ser
        280                 285                 290

gga tca ggc att gat gat gat gaa gat ttt atc tcc agc acc att tca     1088
Gly Ser Gly Ile Asp Asp Asp Glu Asp Phe Ile Ser Ser Thr Ile Ser
    295                 300                 305

acc aca cca cgg gct ttt gac cac aca aaa cag aac cag gac tgg acc     1136
Thr Thr Pro Arg Ala Phe Asp His Thr Lys Gln Asn Gln Asp Trp Thr
310                 315                 320                 325

cag tgg aac cca agc cat tca aat ccg gaa gtg cta ctt cag aca acc     1184
Gln Trp Asn Pro Ser His Ser Asn Pro Glu Val Leu Leu Gln Thr Thr
                330                 335                 340

aca agg atg act gat gta gac aga aat ggc acc act gct tat gaa gga     1232
Thr Arg Met Thr Asp Val Asp Arg Asn Gly Thr Thr Ala Tyr Glu Gly
            345                 350                 355

aac tgg aac cca gaa gca cac cct ccc ctc att cac cat gag cat cat     1280
Asn Trp Asn Pro Glu Ala His Pro Pro Leu Ile His His Glu His His
        360                 365                 370

gag gaa gaa gag acc cca cat tct aca agc aca atc cag gca act cct     1328
Glu Glu Glu Glu Thr Pro His Ser Thr Ser Thr Ile Gln Ala Thr Pro
    375                 380                 385

agt agt aca acg gaa gaa aca gct acc cag aag gaa cag tgg ttt ggc     1376
Ser Ser Thr Thr Glu Glu Thr Ala Thr Gln Lys Glu Gln Trp Phe Gly
390                 395                 400                 405

aac aga tgg cat gag gga tat cgc caa aca ccc aaa gaa gac tcc cat     1424
Asn Arg Trp His Glu Gly Tyr Arg Gln Thr Pro Lys Glu Asp Ser His
                410                 415                 420

tcg aca aca ggg aca gct gca gcc tca gct cat acc agc cat cca atg     1472
Ser Thr Thr Gly Thr Ala Ala Ala Ser Ala His Thr Ser His Pro Met
            425                 430                 435

caa gga agg aca aca cca agc cca gag gac agt tcc tgg act gat ttc     1520
Gln Gly Arg Thr Thr Pro Ser Pro Glu Asp Ser Ser Trp Thr Asp Phe
        440                 445                 450

ttc aac cca atc tca cac ccc atg gga cga ggt cat caa gca gga aga     1568
Phe Asn Pro Ile Ser His Pro Met Gly Arg Gly His Gln Ala Gly Arg
    455                 460                 465

agg atg gat atg gac tcc agt cat agt ata acg ctt cag cct act gca     1616
Arg Met Asp Met Asp Ser Ser His Ser Ile Thr Leu Gln Pro Thr Ala
470                 475                 480                 485
```

```
aat cca aac aca ggt ttg gtg gaa gat ttg gac agg aca gga cct ctt      1664
Asn Pro Asn Thr Gly Leu Val Glu Asp Leu Asp Arg Thr Gly Pro Leu
                490                 495                 500

tca atg aca acg cag cag agt aat tct cag agc ttc tct aca tca cat      1712
Ser Met Thr Thr Gln Gln Ser Asn Ser Gln Ser Phe Ser Thr Ser His
            505                 510                 515

gaa ggc ttg gaa gaa gat aaa gac cat cca aca act tct act ctg aca      1760
Glu Gly Leu Glu Glu Asp Lys Asp His Pro Thr Thr Ser Thr Leu Thr
        520                 525                 530

tca agc aat agg aat gat gtc aca ggt gga aga aga gac cca aat cat      1808
Ser Ser Asn Arg Asn Asp Val Thr Gly Gly Arg Arg Asp Pro Asn His
    535                 540                 545

tct gaa ggc tca act act tta ctg gaa ggt tat acc tct cat tac cca      1856
Ser Glu Gly Ser Thr Thr Leu Leu Glu Gly Tyr Thr Ser His Tyr Pro
550                 555                 560                 565

cac acg aag gaa agc agg acc ttc atc cca gtg acc tca gct aag act      1904
His Thr Lys Glu Ser Arg Thr Phe Ile Pro Val Thr Ser Ala Lys Thr
                570                 575                 580

ggg tcc ttt gga gtt act gca gtt act gtt gga gat tcc aac tct aat      1952
Gly Ser Phe Gly Val Thr Ala Val Thr Val Gly Asp Ser Asn Ser Asn
            585                 590                 595

gtc aat cgt tcc tta tca gga gac caa gac aca ttc cac ccc agt ggg      2000
Val Asn Arg Ser Leu Ser Gly Asp Gln Asp Thr Phe His Pro Ser Gly
        600                 605                 610

ggg tcc cat acc act cat gga tct gaa tca gat gga cac tca cat ggg      2048
Gly Ser His Thr Thr His Gly Ser Glu Ser Asp Gly His Ser His Gly
    615                 620                 625

agt caa gaa ggt gga gca aac aca acc tct ggt cct ata agg aca ccc      2096
Ser Gln Glu Gly Gly Ala Asn Thr Thr Ser Gly Pro Ile Arg Thr Pro
630                 635                 640                 645

caa att cca gaa tgg ctg atc atc ttg gca tcc ctc ttg gcc ttg gct      2144
Gln Ile Pro Glu Trp Leu Ile Ile Leu Ala Ser Leu Leu Ala Leu Ala
                650                 655                 660

ttg att ctt gca gtt tgc att gca gtc aac agt cga aga agg tgt ggg      2192
Leu Ile Leu Ala Val Cys Ile Ala Val Asn Ser Arg Arg Arg Cys Gly
            665                 670                 675

cag aag aaa aag cta gtg atc aac agt ggc aat gga gct gtg gag gac      2240
Gln Lys Lys Lys Leu Val Ile Asn Ser Gly Asn Gly Ala Val Glu Asp
        680                 685                 690

aga aag cca agt gga ctc aac gga gag gcc agc aag tct cag gaa atg      2288
Arg Lys Pro Ser Gly Leu Asn Gly Glu Ala Ser Lys Ser Gln Glu Met
    695                 700                 705

gtg cat ttg gtg aac aag gag tcg tca gaa act cca gac cag ttt atg      2336
Val His Leu Val Asn Lys Glu Ser Ser Glu Thr Pro Asp Gln Phe Met
710                 715                 720                 725

aca gct gat gag aca agg aac ctg cag aat gtg gac atg aag att ggg      2384
Thr Ala Asp Glu Thr Arg Asn Leu Gln Asn Val Asp Met Lys Ile Gly
                730                 735                 740

gtg taa cacctacacc attatcttgg aaagaaacaa ccgttggaaa cataaccatt      2440
Val

acagggagct gggacactta acagatgcaa tgtgctactg attgtttcat tgcgaatctt   2500

ttttagcata aaattttcta ctctttttgt tttttgtgtt ttgttcttta aagtcaggtc   2560

caatttgtaa aaacagcatt gctttctgaa attagggccc aattaataat cagcaagaat   2620

ttgatcgttc cagttcccac ttggaggcct ttcatccctc gggtgtgcta tggatggctt   2680

ctaacaaaaa ctacacatat gtattcctga tcgccaacct ttcccccacc agctaaggac   2740

atttcccagg gttaataggg cctggtccct gggaggaaat ttgaatgggt ccattttgcc   2800
```

cttccatagc ctaatccctg ggcattgctt tccactgagg ttgggggttg gggtgtacta 2860
gttacacatc ttcaacagac cccctctaga aatttttcag atgcttctgg gagacaccca 2920
aagggtgaag ctatttatct gtagtaaact atttatctgt gtttttgaaa tattaaaccc 2980
tggatcagtc ctttgatcag tataattttt taaagttact ttgtcagagg cacaaaaggg 3040
tttaaactga ttcataataa atatctgtac ttcttcgatc ttc 3083

<210> SEQ ID NO 6
<211> LENGTH: 742
<212> TYPE: PRT
<213> ORGANISM: homo sapiens

<400> SEQUENCE: 6

Met Asp Lys Phe Trp Trp His Ala Ala Trp Gly Leu Cys Leu Val Pro
1 5 10 15

Leu Ser Leu Ala Gln Ile Asp Leu Asn Ile Thr Cys Arg Phe Ala Gly
20 25 30

Val Phe His Val Glu Lys Asn Gly Arg Tyr Ser Ile Ser Arg Thr Glu
35 40 45

Ala Ala Asp Leu Cys Lys Ala Phe Asn Ser Thr Leu Pro Thr Met Ala
50 55 60

Gln Met Glu Lys Ala Leu Ser Ile Gly Phe Glu Thr Cys Arg Tyr Gly
65 70 75 80

Phe Ile Glu Gly His Val Val Ile Pro Arg Ile His Pro Asn Ser Ile
85 90 95

Cys Ala Ala Asn Asn Thr Gly Val Tyr Ile Leu Thr Ser Asn Thr Ser
100 105 110

Gln Tyr Asp Thr Tyr Cys Phe Asn Ala Ser Ala Pro Pro Glu Glu Asp
115 120 125

Cys Thr Ser Val Thr Asp Leu Pro Asn Ala Phe Asp Gly Pro Ile Thr
130 135 140

Ile Thr Ile Val Asn Arg Asp Gly Thr Arg Tyr Val Gln Lys Gly Glu
145 150 155 160

Tyr Arg Thr Asn Pro Glu Asp Ile Tyr Pro Ser Asn Pro Thr Asp Asp
165 170 175

Asp Val Ser Ser Gly Ser Ser Ser Glu Arg Ser Ser Thr Ser Gly Gly
180 185 190

Tyr Ile Phe Tyr Thr Phe Ser Thr Val His Pro Ile Pro Asp Glu Asp
195 200 205

Ser Pro Trp Ile Thr Asp Ser Thr Asp Arg Ile Pro Ala Thr Thr Leu
210 215 220

Met Ser Thr Ser Ala Thr Ala Thr Glu Thr Ala Thr Lys Arg Gln Glu
225 230 235 240

Thr Trp Asp Trp Phe Ser Trp Leu Phe Leu Pro Ser Glu Ser Lys Asn
245 250 255

His Leu His Thr Thr Thr Gln Met Ala Gly Thr Ser Ser Asn Thr Ile
260 265 270

Ser Ala Gly Trp Glu Pro Asn Glu Glu Asn Glu Asp Glu Arg Asp Arg
275 280 285

His Leu Ser Phe Ser Gly Ser Gly Ile Asp Asp Asp Glu Asp Phe Ile
290 295 300

Ser Ser Thr Ile Ser Thr Thr Pro Arg Ala Phe Asp His Thr Lys Gln
305 310 315 320

Asn Gln Asp Trp Thr Gln Trp Asn Pro Ser His Ser Asn Pro Glu Val

```
                325                 330                 335

Leu Leu Gln Thr Thr Thr Arg Met Thr Asp Val Asp Arg Asn Gly Thr
            340                 345                 350

Thr Ala Tyr Glu Gly Asn Trp Asn Pro Glu Ala His Pro Pro Leu Ile
        355                 360                 365

His His Glu His His Glu Glu Glu Glu Thr Pro His Ser Thr Ser Thr
    370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro
                405                 410                 415

Lys Glu Asp Ser His Ser Thr Thr Gly Thr Ala Ala Ala Ser Ala His
            420                 425                 430

Thr Ser His Pro Met Gln Gly Arg Thr Thr Pro Ser Pro Glu Asp Ser
        435                 440                 445

Ser Trp Thr Asp Phe Phe Asn Pro Ile Ser His Pro Met Gly Arg Gly
    450                 455                 460

His Gln Ala Gly Arg Arg Met Asp Met Asp Ser Ser His Ser Ile Thr
465                 470                 475                 480

Leu Gln Pro Thr Ala Asn Pro Asn Thr Gly Leu Val Glu Asp Leu Asp
                485                 490                 495

Arg Thr Gly Pro Leu Ser Met Thr Thr Gln Gln Ser Asn Ser Gln Ser
            500                 505                 510

Phe Ser Thr Ser His Glu Gly Leu Glu Glu Asp Lys Asp His Pro Thr
        515                 520                 525

Thr Ser Thr Leu Thr Ser Ser Asn Arg Asn Asp Val Thr Gly Gly Arg
    530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
                565                 570                 575

Thr Ser Ala Lys Thr Gly Ser Phe Gly Val Thr Ala Val Thr Val Gly
            580                 585                 590

Asp Ser Asn Ser Asn Val Asn Arg Ser Leu Ser Gly Asp Gln Asp Thr
        595                 600                 605

Phe His Pro Ser Gly Gly Ser His Thr Thr His Gly Ser Glu Ser Asp
    610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn Ser
            660                 665                 670

Arg Arg Arg Cys Gly Gln Lys Lys Lys Leu Val Ile Asn Ser Gly Asn
        675                 680                 685

Gly Ala Val Glu Asp Arg Lys Pro Ser Gly Leu Asn Gly Glu Ala Ser
    690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
                725                 730                 735

Asp Met Lys Ile Gly Val
            740
```

```
<210> SEQ ID NO 7
<211> LENGTH: 1750
<212> TYPE: DNA
<213> ORGANISM: homo sapiens
<220> FEATURE:
<221> NAME/KEY: CDS
<222> LOCATION: (53)..(1135)

<400> SEQUENCE: 7

cctacaggtg aaaagcccag cgacccagtc aggatttaag tttacctcaa aa atg gaa      58
                                                          Met Glu
                                                          1

gat ttt aac atg gag agt gac agc ttt gaa gat ttc tgg aaa ggt gaa      106
Asp Phe Asn Met Glu Ser Asp Ser Phe Glu Asp Phe Trp Lys Gly Glu
        5                   10                  15

gat ctt agt aat tac agt tac agc tct acc ctg ccc cct ttt cta cta      154
Asp Leu Ser Asn Tyr Ser Tyr Ser Ser Thr Leu Pro Pro Phe Leu Leu
    20                  25                  30

gat gcc gcc cca tgt gaa cca gaa tcc ctg gaa atc aac aag tat ttt      202
Asp Ala Ala Pro Cys Glu Pro Glu Ser Leu Glu Ile Asn Lys Tyr Phe
35                  40                  45                  50

gtg gtc att atc tat gcc ctg gta ttc ctg ctg agc ctg ctg gga aac      250
Val Val Ile Ile Tyr Ala Leu Val Phe Leu Leu Ser Leu Leu Gly Asn
                55                  60                  65

tcc ctc gtg atg ctg gtc atc tta tac agc agg gtc ggc cgc tcc gtc      298
Ser Leu Val Met Leu Val Ile Leu Tyr Ser Arg Val Gly Arg Ser Val
            70                  75                  80

act gat gtc tac ctg ctg aac cta gcc ttg gcc gac cta ctc ttt gcc      346
Thr Asp Val Tyr Leu Leu Asn Leu Ala Leu Ala Asp Leu Leu Phe Ala
        85                  90                  95

ctg acc ttg ccc atc tgg gcc gcc tcc aag gtg aat ggc tgg att ttt      394
Leu Thr Leu Pro Ile Trp Ala Ala Ser Lys Val Asn Gly Trp Ile Phe
    100                 105                 110

ggc aca ttc ctg tgc aag gtg gtc tca ctc ctg aag gaa gtc aac ttc      442
Gly Thr Phe Leu Cys Lys Val Val Ser Leu Leu Lys Glu Val Asn Phe
115                 120                 125                 130

tat agt ggc atc ctg cta ctg gcc tgc atc agt gtg gac cgt tac ctg      490
Tyr Ser Gly Ile Leu Leu Leu Ala Cys Ile Ser Val Asp Arg Tyr Leu
                135                 140                 145

gcc att gtc cat gcc aca cgc aca ctg acc cag aag cgc tac ttg gtc      538
Ala Ile Val His Ala Thr Arg Thr Leu Thr Gln Lys Arg Tyr Leu Val
            150                 155                 160

aaa ttc ata tgt ctc agc atc tgg ggt ctg tcc ttg ctc ctg gcc ctg      586
Lys Phe Ile Cys Leu Ser Ile Trp Gly Leu Ser Leu Leu Leu Ala Leu
        165                 170                 175

cct gtc tta ctt ttc cga agg acc gtc tac tca tcc aat gtt agc cca      634
Pro Val Leu Leu Phe Arg Arg Thr Val Tyr Ser Ser Asn Val Ser Pro
    180                 185                 190

gcc tgc tat gag gac atg ggc aac aat aca gca aac tgg cgg atg ctg      682
Ala Cys Tyr Glu Asp Met Gly Asn Asn Thr Ala Asn Trp Arg Met Leu
195                 200                 205                 210

tta cgg atc ctg ccc cag tcc ttt ggc ttc atc gtg cca ctg ctg atc      730
Leu Arg Ile Leu Pro Gln Ser Phe Gly Phe Ile Val Pro Leu Leu Ile
                215                 220                 225

atg ctg ttc tgc tac gga ttc acc ctg cgt acg ctg ttt aag gcc cac      778
Met Leu Phe Cys Tyr Gly Phe Thr Leu Arg Thr Leu Phe Lys Ala His
            230                 235                 240

atg ggg cag aag cac cgg gcc atg cgg gtc atc ttt gct gtc gtc ctc      826
Met Gly Gln Lys His Arg Ala Met Arg Val Ile Phe Ala Val Val Leu
        245                 250                 255
```

```
atc ttc ctg ctt tgc tgg ctg ccc tac aac ctg gtc ctg ctg gca gac      874
Ile Phe Leu Leu Cys Trp Leu Pro Tyr Asn Leu Val Leu Leu Ala Asp
    260                 265                 270

acc ctc atg agg acc cag gtg atc cag gag acc tgt gag cgc cgc aat      922
Thr Leu Met Arg Thr Gln Val Ile Gln Glu Thr Cys Glu Arg Arg Asn
275                 280                 285                 290

cac atc gac cgg gct ctg gat gcc acc gag att ctg ggc atc ctt cac      970
His Ile Asp Arg Ala Leu Asp Ala Thr Glu Ile Leu Gly Ile Leu His
                295                 300                 305

agc tgc ctc aac ccc ctc atc tac gcc ttc att ggc cag aag ttt cgc     1018
Ser Cys Leu Asn Pro Leu Ile Tyr Ala Phe Ile Gly Gln Lys Phe Arg
            310                 315                 320

cat gga ctc ctc aag att cta gct ata cat ggc ttg atc agc aag gac     1066
His Gly Leu Leu Lys Ile Leu Ala Ile His Gly Leu Ile Ser Lys Asp
        325                 330                 335

tcc ctg ccc aaa gac agc agg cct tcc ttt gtt ggc tct tct tca ggg     1114
Ser Leu Pro Lys Asp Ser Arg Pro Ser Phe Val Gly Ser Ser Ser Gly
    340                 345                 350

cac act tcc act act ctc taa gacctcctgc ctaagtgcag ccccgtgggg        1165
His Thr Ser Thr Thr Leu
355                 360

ttcctccctt ctcttcacag tcacattcca agcctcatgt ccactggttc ttcttggtct   1225

cagtgtcaat gcagccccca ttgtggtcac aggaagcaga ggaggccacg ttcttactag   1285

tttcccttgc atggtttaga aagcttgccc tggtgcctca ccccttgcca taattactat   1345

gtcatttgct ggagctctgc ccatcctgcc cctgagccca tggcactcta tgttctaaga   1405

agtgaaaatc tacactccag tgagacagct ctgcatactc attaggatgg ctagtatcaa   1465

aagaaagaaa atcaggctgg ccaacgggat gaaaccctgt ctctactaaa aatacaaaaa   1525

aaaaaaaaaa aattagccgg gcgtggtggt gagtgcctgt aatcacagct acttgggagg   1585

ctgagatggg agaatcactt gaacccggga ggcagaggtt gcagtgagcc gagattgtgc   1645

ccctgcactc cagcctgagc gacagtgaga ctctgtctca gtccatgaag atgtagagga   1705

gaaactggaa ctctcgagcg ttgctggggg ggattgtaaa atggt                   1750


<210> SEQ ID NO 8
<211> LENGTH: 360
<212> TYPE: PRT
<213> ORGANISM: homo sapiens

<400> SEQUENCE: 8

Met Glu Asp Phe Asn Met Glu Ser Asp Ser Phe Glu Asp Phe Trp Lys
1               5                   10                  15

Gly Glu Asp Leu Ser Asn Tyr Ser Tyr Ser Ser Thr Leu Pro Pro Phe
            20                  25                  30

Leu Leu Asp Ala Ala Pro Cys Glu Pro Glu Ser Leu Glu Ile Asn Lys
        35                  40                  45

Tyr Phe Val Val Ile Ile Tyr Ala Leu Val Phe Leu Leu Ser Leu Leu
    50                  55                  60

Gly Asn Ser Leu Val Met Leu Val Ile Leu Tyr Ser Arg Val Gly Arg
65                  70                  75                  80

Ser Val Thr Asp Val Tyr Leu Leu Asn Leu Ala Leu Ala Asp Leu Leu
                85                  90                  95

Phe Ala Leu Thr Leu Pro Ile Trp Ala Ala Ser Lys Val Asn Gly Trp
            100                 105                 110

Ile Phe Gly Thr Phe Leu Cys Lys Val Val Ser Leu Leu Lys Glu Val
```

```
        115                 120                 125

Asn Phe Tyr Ser Gly Ile Leu Leu Leu Ala Cys Ile Ser Val Asp Arg
    130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu Leu
                165                 170                 175

Ala Leu Pro Val Leu Leu Phe Arg Arg Thr Val Tyr Ser Ser Asn Val
            180                 185                 190

Ser Pro Ala Cys Tyr Glu Asp Met Gly Asn Asn Thr Ala Asn Trp Arg
        195                 200                 205

Met Leu Leu Arg Ile Leu Pro Gln Ser Phe Gly Phe Ile Val Pro Leu
    210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
        275                 280                 285

Arg Asn His Ile Asp Arg Ala Leu Asp Ala Thr Glu Ile Leu Gly Ile
    290                 295                 300

Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
            340                 345                 350

Ser Gly His Thr Ser Thr Thr Leu
        355                 360


<210> SEQ ID NO 9
<211> LENGTH: 324
<212> TYPE: DNA
<213> ORGANISM: homo sapiens
<220> FEATURE:
<221> NAME/KEY: CDS
<222> LOCATION: (1)..(324)

<400> SEQUENCE: 9

atg gcc cgc gct gct ctc tcc gcc gcc ccc agc aat ccc cgg ctc ctg       48
Met Ala Arg Ala Ala Leu Ser Ala Ala Pro Ser Asn Pro Arg Leu Leu
1               5                   10                  15

cga gtg gca ctg ctg ctc ctg ctc ctg gta gcc gct ggc cgg cgc gca       96
Arg Val Ala Leu Leu Leu Leu Leu Leu Val Ala Ala Gly Arg Arg Ala
            20                  25                  30

gca gga gcg tcc gtg gcc act gaa ctg cgc tgc cag tgc ttg cag acc      144
Ala Gly Ala Ser Val Ala Thr Glu Leu Arg Cys Gln Cys Leu Gln Thr
        35                  40                  45

ctg cag gga att cac ccc aag aac atc caa agt gtg aac gtg aag tcc      192
Leu Gln Gly Ile His Pro Lys Asn Ile Gln Ser Val Asn Val Lys Ser
    50                  55                  60

ccc gga ccc cac tgc gcc caa acc gaa gtc ata gcc aca ctc aag aat      240
Pro Gly Pro His Cys Ala Gln Thr Glu Val Ile Ala Thr Leu Lys Asn
65                  70                  75                  80

ggg cgg aaa gct tgc ctc aat cct gca tcc ccc ata gtt aag aaa atc      288
```

```
Gly Arg Lys Ala Cys Leu Asn Pro Ala Ser Pro Ile Val Lys Lys Ile
            85                  90                  95

atc gaa aag atg ctg aac agt gac aaa tcc aac tga                 324
Ile Glu Lys Met Leu Asn Ser Asp Lys Ser Asn
            100                 105


<210> SEQ ID NO 10
<211> LENGTH: 107
<212> TYPE: PRT
<213> ORGANISM: homo sapiens

<400> SEQUENCE: 10

Met Ala Arg Ala Ala Leu Ser Ala Ala Pro Ser Asn Pro Arg Leu Leu
1               5                   10                  15

Arg Val Ala Leu Leu Leu Leu Leu Leu Val Ala Ala Gly Arg Arg Ala
            20                  25                  30

Ala Gly Ala Ser Val Ala Thr Glu Leu Arg Cys Gln Cys Leu Gln Thr
        35                  40                  45

Leu Gln Gly Ile His Pro Lys Asn Ile Gln Ser Val Asn Val Lys Ser
    50                  55                  60

Pro Gly Pro His Cys Ala Gln Thr Glu Val Ile Ala Thr Leu Lys Asn
65                  70                  75                  80

Gly Arg Lys Ala Cys Leu Asn Pro Ala Ser Pro Ile Val Lys Lys Ile
            85                  90                  95

Ile Glu Lys Met Leu Asn Ser Asp Lys Ser Asn
            100                 105


<210> SEQ ID NO 11
<211> LENGTH: 1166
<212> TYPE: DNA
<213> ORGANISM: homo sapiens
<220> FEATURE:
<221> NAME/KEY: CDS
<222> LOCATION: (163)..(486)

<400> SEQUENCE: 11

gctccgggaa tttccctggc ccggccgctc cgggctttcc agtctcaacc atgcataaaa     60

agggttcgcc gatcttgggg agccacacag cccgggtcgc aggcacctcc ccgccagctc    120

tcccgcttct cgcacagctt cccgacgcgt ctgctgagcc cc atg gcc cac gcc       174
                                               Met Ala His Ala
                                               1

acg ctc tcc gcc gcc ccc agc aat ccc cgg ctc ctg cgg gtg gcg ctg      222
Thr Leu Ser Ala Ala Pro Ser Asn Pro Arg Leu Leu Arg Val Ala Leu
5                   10                  15                  20

ctg ctc ctg ctc ctg gtg gcc gcc agc cgg cgc gca gca gga gcg tcc      270
Leu Leu Leu Leu Leu Val Ala Ala Ser Arg Arg Ala Ala Gly Ala Ser
                25                  30                  35

gtg gtc act gaa ctg cgc tgc cag tgc ttg cag aca ctg cag gga att      318
Val Val Thr Glu Leu Arg Cys Gln Cys Leu Gln Thr Leu Gln Gly Ile
            40                  45                  50

cac ctc aag aac atc caa agt gtg aat gta agg tcc ccc gga ccc cac      366
His Leu Lys Asn Ile Gln Ser Val Asn Val Arg Ser Pro Gly Pro His
        55                  60                  65

tgc gcc caa acc gaa gtc ata gcc aca ctc aag aat ggg aag aaa gct      414
Cys Ala Gln Thr Glu Val Ile Ala Thr Leu Lys Asn Gly Lys Lys Ala
    70                  75                  80

tgt ctc aac ccc gca tcc ccc atg gtt cag aaa atc atc gaa aag ata      462
Cys Leu Asn Pro Ala Ser Pro Met Val Gln Lys Ile Ile Glu Lys Ile
85                  90                  95                  100
```

```
ctg aac aag ggg agc acc aac tga caggagagaa gtaagaagct tatcagcgta     516
Leu Asn Lys Gly Ser Thr Asn
                105

tcattgacac ttcctgcagg gtggtccctg cccttaccag agctgaaaat gaaaaagaga    576

acagcagctt tctagggaca gctggaaagg acttaatgtg tttgactatt tcttacgagg    636

gttctactta tttatgtatt tatttttgaa agcttgtatt ttaatatttt acatgctgtt    696

atttaaagat gtgagtgtgt ttcatcaaac atagctcagt cctgattatt taattggaat    756

atgatgggtt ttaaatgtgt cattaaacta atatttagtg ggagaccata atgtgtcagc    816

caccttgata aatgacaggg tggggaactg gagggtgggg ggattgaaat gcaagcaatt    876

agtggatcac tgttagggta agggaatgta tgtacacatc tattttttat acttttttt     936

taaaaaaaga atgtcagttg ttatttattc aaattatctc acattatgtg ttcaacattt    996

ttatgctgaa gtttccctta gacattttat gtcttgcttg tagggcataa tgccttgttt   1056

aatgtccatt ctgcagcgtt tctctttccc ttggaaaaga gaatttatca ttactgttac   1116

atttgtacaa atgacatgat aataaaagtt ttatgaaaaa aaaaaaaaaa              1166


<210> SEQ ID NO 12
<211> LENGTH: 107
<212> TYPE: PRT
<213> ORGANISM: homo sapiens

<400> SEQUENCE: 12

Met Ala His Ala Thr Leu Ser Ala Ala Pro Ser Asn Pro Arg Leu Leu
1               5                   10                  15

Arg Val Ala Leu Leu Leu Leu Leu Leu Val Ala Ala Ser Arg Arg Ala
            20                  25                  30

Ala Gly Ala Ser Val Val Thr Glu Leu Arg Cys Gln Cys Leu Gln Thr
        35                  40                  45

Leu Gln Gly Ile His Leu Lys Asn Ile Gln Ser Val Asn Val Arg Ser
    50                  55                  60

Pro Gly Pro His Cys Ala Gln Thr Glu Val Ile Ala Thr Leu Lys Asn
65                  70                  75                  80

Gly Lys Lys Ala Cys Leu Asn Pro Ala Ser Pro Met Val Gln Lys Ile
                85                  90                  95

Ile Glu Lys Ile Leu Asn Lys Gly Ser Thr Asn
            100                 105


<210> SEQ ID NO 13
<211> LENGTH: 1609
<212> TYPE: DNA
<213> ORGANISM: homo sapiens
<220> FEATURE:
<221> NAME/KEY: CDS
<222> LOCATION: (92)..(1609)

<400> SEQUENCE: 13

ttcaagtctt tttcttttaa cggattgatc ttttgctaga tagagacaaa atatcagtgt     60

gaattacagc aaacccctat tccatgctgt t atg ggt gaa act ctg gga gat      112
                                   Met Gly Glu Thr Leu Gly Asp
                                   1               5

tct cct att gac cca gaa agc gat tcc ttc act gat aca ctg tct gca      160
Ser Pro Ile Asp Pro Glu Ser Asp Ser Phe Thr Asp Thr Leu Ser Ala
        10                  15                  20

aac ata tca caa gaa atg acc atg gtt gac aca gag atg cca ttc tgg      208
Asn Ile Ser Gln Glu Met Thr Met Val Asp Thr Glu Met Pro Phe Trp
    25                  30                  35
```

```
ccc acc aac ttt ggg atc agc tcc gtg gat ctc tcc gta atg gaa gac      256
Pro Thr Asn Phe Gly Ile Ser Ser Val Asp Leu Ser Val Met Glu Asp
40                  45                  50                  55

cac tcc cac tcc ttt gat atc aag ccc ttc act act gtt gac ttc tcc      304
His Ser His Ser Phe Asp Ile Lys Pro Phe Thr Thr Val Asp Phe Ser
                60                  65                  70

agc att tct act cca cat tac gaa gac att cca ttc aca aga aca gat      352
Ser Ile Ser Thr Pro His Tyr Glu Asp Ile Pro Phe Thr Arg Thr Asp
            75                  80                  85

cca gtg gtt gca gat tac aag tat gac ctg aaa ctt caa gag tac caa      400
Pro Val Val Ala Asp Tyr Lys Tyr Asp Leu Lys Leu Gln Glu Tyr Gln
        90                  95                  100

agt gca atc aaa gtg gag cct gca tct cca cct tat tat tct gag aag      448
Ser Ala Ile Lys Val Glu Pro Ala Ser Pro Pro Tyr Tyr Ser Glu Lys
    105                 110                 115

act cag ctc tac aat aag cct cat gaa gag cct tcc aac tcc ctc atg      496
Thr Gln Leu Tyr Asn Lys Pro His Glu Glu Pro Ser Asn Ser Leu Met
120                 125                 130                 135

gca att gaa tgt cgt gtc tgt gga gat aaa gct tct gga ttt cac tat      544
Ala Ile Glu Cys Arg Val Cys Gly Asp Lys Ala Ser Gly Phe His Tyr
                140                 145                 150

gga gtt cat gct tgt gaa gga tgc aag ggt ttc ttc cgg aga aca atc      592
Gly Val His Ala Cys Glu Gly Cys Lys Gly Phe Phe Arg Arg Thr Ile
            155                 160                 165

aga ttg aag ctt atc tat gac aga tgt gat ctt aac tgt cgg atc cac      640
Arg Leu Lys Leu Ile Tyr Asp Arg Cys Asp Leu Asn Cys Arg Ile His
        170                 175                 180

aaa aaa agt aga aat aaa tgt cag tac tgt cgg ttt cag aaa tgc ctt      688
Lys Lys Ser Arg Asn Lys Cys Gln Tyr Cys Arg Phe Gln Lys Cys Leu
    185                 190                 195

gca gtg ggg atg tct cat aat gcc atc agg ttt ggg cgg atg cca cag      736
Ala Val Gly Met Ser His Asn Ala Ile Arg Phe Gly Arg Met Pro Gln
200                 205                 210                 215

gcc gag aag gag aag ctg ttg gcg gag atc tcc agt gat atc gac cag      784
Ala Glu Lys Glu Lys Leu Leu Ala Glu Ile Ser Ser Asp Ile Asp Gln
                220                 225                 230

ctg aat cca gag tcc gct gac ctc cgg gcc ctg gca aaa cat ttg tat      832
Leu Asn Pro Glu Ser Ala Asp Leu Arg Ala Leu Ala Lys His Leu Tyr
            235                 240                 245

gac tca tac ata aag tcc ttc ccg ctg acc aaa gca aag gcg agg gcg      880
Asp Ser Tyr Ile Lys Ser Phe Pro Leu Thr Lys Ala Lys Ala Arg Ala
        250                 255                 260

atc ttg aca gga aag aca aca gac aaa tca cca ttc gtt atc tat gac      928
Ile Leu Thr Gly Lys Thr Thr Asp Lys Ser Pro Phe Val Ile Tyr Asp
    265                 270                 275

atg aat tcc tta atg atg gga gaa gat aaa atc aag ttc aaa cac atc      976
Met Asn Ser Leu Met Met Gly Glu Asp Lys Ile Lys Phe Lys His Ile
280                 285                 290                 295

acc ccc ctg cag gag cag agc aaa gag gtg gcc atc cgc atc ttt cag     1024
Thr Pro Leu Gln Glu Gln Ser Lys Glu Val Ala Ile Arg Ile Phe Gln
                300                 305                 310

ggc tgc cag ttt cgc tcc gtg gag gct gtg cag gag atc aca gag tat     1072
Gly Cys Gln Phe Arg Ser Val Glu Ala Val Gln Glu Ile Thr Glu Tyr
            315                 320                 325

gcc aaa agc att cct ggt ttt gta aat ctt gac ttg aac gac caa gta     1120
Ala Lys Ser Ile Pro Gly Phe Val Asn Leu Asp Leu Asn Asp Gln Val
        330                 335                 340

act ctc ctc aaa tat gga gtc cac gag atc att tac aca atg ctg gcc     1168
Thr Leu Leu Lys Tyr Gly Val His Glu Ile Ile Tyr Thr Met Leu Ala
```

```
    345                 350                 355

tcc ttg atg aat aaa gat ggg gtt ctc ata tcc gag ggc caa ggc ttc      1216
Ser Leu Met Asn Lys Asp Gly Val Leu Ile Ser Glu Gly Gln Gly Phe
360                 365                 370                 375

atg aca agg gag ttt cta aag agc ctg cga aag cct ttt ggt gac ttt      1264
Met Thr Arg Glu Phe Leu Lys Ser Leu Arg Lys Pro Phe Gly Asp Phe
                380                 385                 390

atg gag ccc aag ttt gag ttt gct gtg aag ttc aat gca ctg gaa tta      1312
Met Glu Pro Lys Phe Glu Phe Ala Val Lys Phe Asn Ala Leu Glu Leu
            395                 400                 405

gat gac agc gac ttg gca ata ttt att gct gtc att att ctc agt gga      1360
Asp Asp Ser Asp Leu Ala Ile Phe Ile Ala Val Ile Ile Leu Ser Gly
        410                 415                 420

gac cgc cca ggt ttg ctg aat gtg aag ccc att gaa gac att caa gac      1408
Asp Arg Pro Gly Leu Leu Asn Val Lys Pro Ile Glu Asp Ile Gln Asp
    425                 430                 435

aac ctg cta caa gcc ctg gag ctc cag ctg aag ctg aac cac cct gag      1456
Asn Leu Leu Gln Ala Leu Glu Leu Gln Leu Lys Leu Asn His Pro Glu
440                 445                 450                 455

tcc tca cag ctg ttt gcc aag ctg ctc cag aaa atg aca gac ctc aga      1504
Ser Ser Gln Leu Phe Ala Lys Leu Leu Gln Lys Met Thr Asp Leu Arg
                460                 465                 470

cag att gtc acg gaa cac gtg cag cta ctg cag gtg atc aag aag acg      1552
Gln Ile Val Thr Glu His Val Gln Leu Leu Gln Val Ile Lys Lys Thr
            475                 480                 485

gag aca gac atg agt ctt cac ccg ctc ctg cag gag atc tac aag gac      1600
Glu Thr Asp Met Ser Leu His Pro Leu Leu Gln Glu Ile Tyr Lys Asp
        490                 495                 500

ttg tac tag                                                          1609
Leu Tyr
    505


<210> SEQ ID NO 14
<211> LENGTH: 505
<212> TYPE: PRT
<213> ORGANISM: homo sapiens

<400> SEQUENCE: 14

Met Gly Glu Thr Leu Gly Asp Ser Pro Ile Asp Pro Glu Ser Asp Ser
1               5                   10                  15

Phe Thr Asp Thr Leu Ser Ala Asn Ile Ser Gln Glu Met Thr Met Val
            20                  25                  30

Asp Thr Glu Met Pro Phe Trp Pro Thr Asn Phe Gly Ile Ser Ser Val
        35                  40                  45

Asp Leu Ser Val Met Glu Asp His Ser His Ser Phe Asp Ile Lys Pro
    50                  55                  60

Phe Thr Thr Val Asp Phe Ser Ser Ile Ser Thr Pro His Tyr Glu Asp
65                  70                  75                  80

Ile Pro Phe Thr Arg Thr Asp Pro Val Val Ala Asp Tyr Lys Tyr Asp
                85                  90                  95

Leu Lys Leu Gln Glu Tyr Gln Ser Ala Ile Lys Val Glu Pro Ala Ser
            100                 105                 110

Pro Pro Tyr Tyr Ser Glu Lys Thr Gln Leu Tyr Asn Lys Pro His Glu
        115                 120                 125

Glu Pro Ser Asn Ser Leu Met Ala Ile Glu Cys Arg Val Cys Gly Asp
    130                 135                 140

Lys Ala Ser Gly Phe His Tyr Gly Val His Ala Cys Glu Gly Cys Lys
145                 150                 155                 160
```

```
Gly Phe Phe Arg Arg Thr Ile Arg Leu Lys Leu Ile Tyr Asp Arg Cys
                165                 170                 175

Asp Leu Asn Cys Arg Ile His Lys Lys Ser Arg Asn Lys Cys Gln Tyr
            180                 185                 190

Cys Arg Phe Gln Lys Cys Leu Ala Val Gly Met Ser His Asn Ala Ile
        195                 200                 205

Arg Phe Gly Arg Met Pro Gln Ala Glu Lys Glu Lys Leu Leu Ala Glu
    210                 215                 220

Ile Ser Ser Asp Ile Asp Gln Leu Asn Pro Glu Ser Ala Asp Leu Arg
225                 230                 235                 240

Ala Leu Ala Lys His Leu Tyr Asp Ser Tyr Ile Lys Ser Phe Pro Leu
                245                 250                 255

Thr Lys Ala Lys Ala Arg Ala Ile Leu Thr Gly Lys Thr Thr Asp Lys
            260                 265                 270

Ser Pro Phe Val Ile Tyr Asp Met Asn Ser Leu Met Met Gly Glu Asp
        275                 280                 285

Lys Ile Lys Phe Lys His Ile Thr Pro Leu Gln Glu Gln Ser Lys Glu
    290                 295                 300

Val Ala Ile Arg Ile Phe Gln Gly Cys Gln Phe Arg Ser Val Glu Ala
305                 310                 315                 320

Val Gln Glu Ile Thr Glu Tyr Ala Lys Ser Ile Pro Gly Phe Val Asn
                325                 330                 335

Leu Asp Leu Asn Asp Gln Val Thr Leu Leu Lys Tyr Gly Val His Glu
            340                 345                 350

Ile Ile Tyr Thr Met Leu Ala Ser Leu Met Asn Lys Asp Gly Val Leu
        355                 360                 365

Ile Ser Glu Gly Gln Gly Phe Met Thr Arg Glu Phe Leu Lys Ser Leu
    370                 375                 380

Arg Lys Pro Phe Gly Asp Phe Met Glu Pro Lys Phe Glu Phe Ala Val
385                 390                 395                 400

Lys Phe Asn Ala Leu Glu Leu Asp Asp Ser Asp Leu Ala Ile Phe Ile
                405                 410                 415

Ala Val Ile Ile Leu Ser Gly Asp Arg Pro Gly Leu Leu Asn Val Lys
            420                 425                 430

Pro Ile Glu Asp Ile Gln Asp Asn Leu Leu Gln Ala Leu Glu Leu Gln
        435                 440                 445

Leu Lys Leu Asn His Pro Glu Ser Ser Gln Leu Phe Ala Lys Leu Leu
    450                 455                 460

Gln Lys Met Thr Asp Leu Arg Gln Ile Val Thr Glu His Val Gln Leu
465                 470                 475                 480

Leu Gln Val Ile Lys Lys Thr Glu Thr Asp Met Ser Leu His Pro Leu
                485                 490                 495

Leu Gln Glu Ile Tyr Lys Asp Leu Tyr
            500                 505


<210> SEQ ID NO 15
<211> LENGTH: 3734
<212> TYPE: DNA
<213> ORGANISM: homo sapiens
<220> FEATURE:
<221> NAME/KEY: CDS
<222> LOCATION: (310)..(1635)

<400> SEQUENCE: 15

gcggagcgtg tgacgctgcg gccgccgcgg acctggggat taatgggaaa agttttggca      60
```

```
ggagcgggag aattctgcgg agcctgcggg acggcggcgg tggcgccgta ggcagccggg    120

acagtgttgt acagtgtttt gggcatgcac gtgatactca cacagtggct tctgctcacc    180

aacagatgaa gacagatgca ccaacgaggc tgatgggaac caccctgtag aggtccatct    240

gcgttcagac ccagacgatg ccagagctat gactgggcct gcaggtgtgg cgccgagggg    300

agatcagcc atg gag cag cca cag gag gaa gcc cct gag gtc cgg gaa gag    351
          Met Glu Gln Pro Gln Glu Glu Ala Pro Glu Val Arg Glu Glu
          1               5                   10

gag gag aaa gag gaa gtg gca gag gca gaa gga gcc cca gag ctc aat      399
Glu Glu Lys Glu Glu Val Ala Glu Ala Glu Gly Ala Pro Glu Leu Asn
15                  20                  25                  30

ggg gga cca cag cat gca ctt cct tcc agc agc tac aca gac ctc tcc      447
Gly Gly Pro Gln His Ala Leu Pro Ser Ser Ser Tyr Thr Asp Leu Ser
                35                  40                  45

cgg agc tcc tcg cca ccc tca ctg ctg gac caa ctg cag atg ggc tgt      495
Arg Ser Ser Ser Pro Pro Ser Leu Leu Asp Gln Leu Gln Met Gly Cys
            50                  55                  60

gac ggg gcc tca tgc ggc agc ctc aac atg gag tgc cgg gtg tgc ggg      543
Asp Gly Ala Ser Cys Gly Ser Leu Asn Met Glu Cys Arg Val Cys Gly
        65                  70                  75

gac aag gca tcg ggc ttc cac tac ggt gtt cat gca tgt gag ggg tgc      591
Asp Lys Ala Ser Gly Phe His Tyr Gly Val His Ala Cys Glu Gly Cys
    80                  85                  90

aag ggc ttc ttc cgt cgt acg atc cgc atg aag ctg gag tac gag aag      639
Lys Gly Phe Phe Arg Arg Thr Ile Arg Met Lys Leu Glu Tyr Glu Lys
95                  100                 105                 110

tgt gag cgc agc tgc aag att cag aag aag aac cgc aac aag tgc cag      687
Cys Glu Arg Ser Cys Lys Ile Gln Lys Lys Asn Arg Asn Lys Cys Gln
                115                 120                 125

tac tgc cgc ttc cag aag tgc ctg gca ctg ggc atg tca cac aac gct      735
Tyr Cys Arg Phe Gln Lys Cys Leu Ala Leu Gly Met Ser His Asn Ala
            130                 135                 140

atc cgt ttt ggt cgg atg ccg gag gct gag aag agg aag ctg gtg gca      783
Ile Arg Phe Gly Arg Met Pro Glu Ala Glu Lys Arg Lys Leu Val Ala
        145                 150                 155

ggg ctg act gca aac gag ggg agc cag tac aac cca cag gtg gcc gac      831
Gly Leu Thr Ala Asn Glu Gly Ser Gln Tyr Asn Pro Gln Val Ala Asp
    160                 165                 170

ctg aag gcc ttc tcc aag cac atc tac aat gcc tac ctg aaa aac ttc      879
Leu Lys Ala Phe Ser Lys His Ile Tyr Asn Ala Tyr Leu Lys Asn Phe
175                 180                 185                 190

aac atg acc aaa aag aag gcc cgc agc atc ctc acc ggc aaa gcc agc      927
Asn Met Thr Lys Lys Lys Ala Arg Ser Ile Leu Thr Gly Lys Ala Ser
                195                 200                 205

cac acg gcg ccc ttt gtg atc cac gac atc gag aca ttg tgg cag gca      975
His Thr Ala Pro Phe Val Ile His Asp Ile Glu Thr Leu Trp Gln Ala
            210                 215                 220

gag aag ggg ctg gtg tgg aag cag ttg gtg aat ggc ctg cct ccc tac     1023
Glu Lys Gly Leu Val Trp Lys Gln Leu Val Asn Gly Leu Pro Pro Tyr
        225                 230                 235

aag gag atc agc gtg cac gtc ttc tac cgc tgc cag tgc acc aca gtg     1071
Lys Glu Ile Ser Val His Val Phe Tyr Arg Cys Gln Cys Thr Thr Val
    240                 245                 250

gag acc gtg cgg gag ctc act gag ttc gcc aag agc atc ccc agc ttc     1119
Glu Thr Val Arg Glu Leu Thr Glu Phe Ala Lys Ser Ile Pro Ser Phe
255                 260                 265                 270

agc agc ctc ttc ctc aac gac cag gtt acc ctt ctc aag tat ggc gtg     1167
Ser Ser Leu Phe Leu Asn Asp Gln Val Thr Leu Leu Lys Tyr Gly Val
```

```
                275                 280                 285

cac gag gcc atc ttc gcc atg ctg gcc tct atc gtc aac aag gac ggg     1215
His Glu Ala Ile Phe Ala Met Leu Ala Ser Ile Val Asn Lys Asp Gly
            290                 295                 300

ctg ctg gta gcc aac ggc agt ggc ttt gtc acc cgt gag ttc ctg cgc     1263
Leu Leu Val Ala Asn Gly Ser Gly Phe Val Thr Arg Glu Phe Leu Arg
        305                 310                 315

agc ctc cgc aaa ccc ttc agt gat atc att gag cct aag ttt gaa ttt     1311
Ser Leu Arg Lys Pro Phe Ser Asp Ile Ile Glu Pro Lys Phe Glu Phe
    320                 325                 330

gct gtc aag ttc aac gcc ctg gaa ctt gat gac agt gac ctg gcc cta     1359
Ala Val Lys Phe Asn Ala Leu Glu Leu Asp Asp Ser Asp Leu Ala Leu
335                 340                 345                 350

ttc att gcg gcc atc att ctg tgt gga gac cgg cca ggc ctc atg aac     1407
Phe Ile Ala Ala Ile Ile Leu Cys Gly Asp Arg Pro Gly Leu Met Asn
                355                 360                 365

gtt cca cgg gtg gag gct atc cag gac acc atc ctg cgt gcc ctc gaa     1455
Val Pro Arg Val Glu Ala Ile Gln Asp Thr Ile Leu Arg Ala Leu Glu
            370                 375                 380

ttc cac ctg cag gcc aac cac cct gat gcc cag tac ctc ttc ccc aag     1503
Phe His Leu Gln Ala Asn His Pro Asp Ala Gln Tyr Leu Phe Pro Lys
        385                 390                 395

ctg ctg cag aag atg gct gac ctg cgg caa ctg gtc acc gag cac gcc     1551
Leu Leu Gln Lys Met Ala Asp Leu Arg Gln Leu Val Thr Glu His Ala
    400                 405                 410

cag atg atg cag cgg atc aag aag acc gaa acc gag acc tcg ctg cac     1599
Gln Met Met Gln Arg Ile Lys Lys Thr Glu Thr Glu Thr Ser Leu His
415                 420                 425                 430

cct ctg ctc cag gag atc tac aag gac atg tac taa cggcggcacc          1645
Pro Leu Leu Gln Glu Ile Tyr Lys Asp Met Tyr
                435                 440

caggcctccc tgcagactcc aatggggcca gcactggagg ggcccaccca catgactttt   1705

ccattgacca gcccttgagc acccggcctg gagcagcaga gtcccacgat cgccctcaga   1765

cacatgacac ccacggcctc tggctccctg tgccctctct cccgcttcct ccagccagct   1825

ctcttcctgt ctttgttgtc tccctctttc tcagttcctc tttcttttct aattcctgtt   1885

gctctgtttc ttcctttctg taggtttctc tcttcccttc tcccttgccc tccctttctc   1945

tctccacccc ccacgtctgt cctcctttct tattctgtga gatgttttgt attatttcac   2005

cagcagcata gaacaggacc tctgcttttg cacacctttt ccccaggagc agaagagagt   2065

ggggcctgcc ctctgcccca tcattgcacc tgcaggctta ggtcctcact tctgtctcct   2125

gtcttcagag caaaagactt gagccatcca aagaaacact aagctctctg ggcctgggtt   2185

ccagggaagg ctaagcatgg cctggactga ctgcagcccc ctatagtcat ggggtccctg   2245

ctgcaaagga cagtgggcag gaggccccag gctgagagcc agatgcctcc ccaagactgt   2305

cattgcccct ccgatgctga ggccacccac tgacccaact gatcctgctc cagcagcaca   2365

cctcagcccc actgacaccc agtgtccttc catcttcaca ctggtttgcc aggccaatgt   2425

tgctgatggc cccctgcact ggccgctgga cggcactctc ccagcttgga agtaggcagg   2485

gttccctcca ggtgggcccc cacctcactg aagaggagca agtctcaaga gaaggagggg   2545

ggattggtgg ttggaggaag cagcacaccc aattctgccc ctaggactcg ggtctgagt    2605

cctggggtca ggccagggag agctcggggc aggccttccg ccagcactcc cactgccccc   2665

ctgcccagta gcagccgccc acattgtgtc agcatccagg gccagggcct ggcctcacat   2725

ccccctgctc ctttctctag ctggctccac gggagttcag gccccactcc ccctgaagct   2785
```

```
gcccctccag cacacacaca taagcactga aatcacttta cctgcaggct ccatgcacct   2845

cccttccctc cctgaggcag gtgagaaccc agagagaggg gcctgcaggt gagcaggcag   2905

ggctgggcca ggtctccggg gaggcagggg tcctgcaggt cctggtgggt cagcccagca   2965

cctgctccca gtgggagctt cccgggataa actgagcctg ttcattctga tgtccatttg   3025

tcccaatagc tctactgccc tccccttccc ctttactcag cccagctggc cacctagaag   3085

tctccctgca cagcctctag tgtccgggga ccttgtggga ccagtcccac accgctggtc   3145

cctgccctcc cctgctccca ggttgaggtg cgctcacctc agagcagggc caaagcacag   3205

ctgggcatgc catgtctgag cggcgcagag ccctccaggc ctgcaggggc aaggggctgg   3265

ctggagtctc agagcacaga ggtaggagaa ctggggttca agcccaggct tcctgggtcc   3325

tgcctggtcc tccctcccaa ggagccattc tgtgtgtgac tctgggtgga agtgcccagc   3385

ccctgcccct acgggcgctg cagcctccct tccatgcccc aggatcactc tctgctggca   3445

ggattcttcc cgctccccac ctacccagct gatgggggtt ggggtgcttc ctttcaggcc   3505

aaggctatga agggacagct gctgggaccc acctccccct ccccggccac atgccgcgtc   3565

cctgccccga cccgggtctg gtgctgagga tacagctctt ctcagtgtct gaacaatctc   3625

caaaattgaa atgtatattt ttgctaggag ccccagcttc ctgtgttttt aatataaata   3685

gtgtacacag actgacgaaa ctttaaataa atgggaatta aatatttaa                3734
```

<210> SEQ ID NO 16
<211> LENGTH: 441
<212> TYPE: PRT
<213> ORGANISM: homo sapiens

<400> SEQUENCE: 16

```
Met Glu Gln Pro Gln Glu Glu Ala Pro Glu Val Arg Glu Glu Glu Glu
1               5                   10                  15

Lys Glu Glu Val Ala Glu Ala Glu Gly Ala Pro Glu Leu Asn Gly Gly
            20                  25                  30

Pro Gln His Ala Leu Pro Ser Ser Ser Tyr Thr Asp Leu Ser Arg Ser
        35                  40                  45

Ser Ser Pro Pro Ser Leu Leu Asp Gln Leu Gln Met Gly Cys Asp Gly
    50                  55                  60

Ala Ser Cys Gly Ser Leu Asn Met Glu Cys Arg Val Cys Gly Asp Lys
65                  70                  75                  80

Ala Ser Gly Phe His Tyr Gly Val His Ala Cys Glu Gly Cys Lys Gly
                85                  90                  95

Phe Phe Arg Arg Thr Ile Arg Met Lys Leu Glu Tyr Glu Lys Cys Glu
            100                 105                 110

Arg Ser Cys Lys Ile Gln Lys Lys Asn Arg Asn Lys Cys Gln Tyr Cys
        115                 120                 125

Arg Phe Gln Lys Cys Leu Ala Leu Gly Met Ser His Asn Ala Ile Arg
    130                 135                 140

Phe Gly Arg Met Pro Glu Ala Glu Lys Arg Lys Leu Val Ala Gly Leu
145                 150                 155                 160

Thr Ala Asn Glu Gly Ser Gln Tyr Asn Pro Gln Val Ala Asp Leu Lys
                165                 170                 175

Ala Phe Ser Lys His Ile Tyr Asn Ala Tyr Leu Lys Asn Phe Asn Met
            180                 185                 190

Thr Lys Lys Lys Ala Arg Ser Ile Leu Thr Gly Lys Ala Ser His Thr
        195                 200                 205
```

```
Ala Pro Phe Val Ile His Asp Ile Glu Thr Leu Trp Gln Ala Glu Lys
    210                 215                 220

Gly Leu Val Trp Lys Gln Leu Val Asn Gly Leu Pro Pro Tyr Lys Glu
225                 230                 235                 240

Ile Ser Val His Val Phe Tyr Arg Cys Gln Cys Thr Thr Val Glu Thr
                245                 250                 255

Val Arg Glu Leu Thr Glu Phe Ala Lys Ser Ile Pro Ser Phe Ser Ser
            260                 265                 270

Leu Phe Leu Asn Asp Gln Val Thr Leu Leu Lys Tyr Gly Val His Glu
        275                 280                 285

Ala Ile Phe Ala Met Leu Ala Ser Ile Val Asn Lys Asp Gly Leu Leu
    290                 295                 300

Val Ala Asn Gly Ser Gly Phe Val Thr Arg Glu Phe Leu Arg Ser Leu
305                 310                 315                 320

Arg Lys Pro Phe Ser Asp Ile Ile Glu Pro Lys Phe Glu Phe Ala Val
                325                 330                 335

Lys Phe Asn Ala Leu Glu Leu Asp Asp Ser Asp Leu Ala Leu Phe Ile
            340                 345                 350

Ala Ala Ile Ile Leu Cys Gly Asp Arg Pro Gly Leu Met Asn Val Pro
        355                 360                 365

Arg Val Glu Ala Ile Gln Asp Thr Ile Leu Arg Ala Leu Glu Phe His
    370                 375                 380

Leu Gln Ala Asn His Pro Asp Ala Gln Tyr Leu Phe Pro Lys Leu Leu
385                 390                 395                 400

Gln Lys Met Ala Asp Leu Arg Gln Leu Val Thr Glu His Ala Gln Met
                405                 410                 415

Met Gln Arg Ile Lys Lys Thr Glu Thr Glu Thr Ser Leu His Pro Leu
            420                 425                 430

Leu Gln Glu Ile Tyr Lys Asp Met Tyr
        435                 440


<210> SEQ ID NO 17
<211> LENGTH: 2121
<212> TYPE: DNA
<213> ORGANISM: homo sapiens
<220> FEATURE:
<221> NAME/KEY: CDS
<222> LOCATION: (559)..(1878)

<400> SEQUENCE: 17

ctgctcgcgg ccgccaccgc cgggccccgg ccgtccctgg ctcccctcct gcctcgagaa      60

gggcagggct tctcagaggc ttggcgggaa aaaagaacgg agggagggat cgcgctgagt     120

ataaaagccg gttttcgggg ctttatctaa ctcgctgtag taattccagc gagaggcaga     180

gggagcgagc gggcggccgg ctagggtgga agagccgggc gagcagagct gcgctgcggg     240

cgtcctggga agggagatcc ggagcgaata gggggcttcg cctctggccc agccctcccg     300

cttgatcccc caggccagcg gtccgcaacc cttgccgcat ccacgaaact ttgcccatag     360

cagcgggcgg gcactttgca ctggaactta caacacccga gcaaggacgc gactctcccg     420

acgcggggag gctattctgc ccatttgggg acacttcccc gccgctgcca ggacccgctt     480

ctctgaaagg ctctccttgc agctgcttag acgctggatt tttttcgggt agtggaaaac     540

cagcagcctc ccgcgacg atg ccc ctc aac gtt agc ttc acc aac agg aac       591
                    Met Pro Leu Asn Val Ser Phe Thr Asn Arg Asn
                    1               5                   10
```

```
tat gac ctc gac tac gac tcg gtg cag ccg tat ttc tac tgc gac gag      639
Tyr Asp Leu Asp Tyr Asp Ser Val Gln Pro Tyr Phe Tyr Cys Asp Glu
            15                  20                  25

gag gag aac ttc tac cag cag cag cag cag agc gag ctg cag ccc ccg      687
Glu Glu Asn Phe Tyr Gln Gln Gln Gln Gln Ser Glu Leu Gln Pro Pro
        30                  35                  40

gcg ccc agc gag gat atc tgg aag aaa ttc gag ctg ctg ccc acc ccg      735
Ala Pro Ser Glu Asp Ile Trp Lys Lys Phe Glu Leu Leu Pro Thr Pro
    45                  50                  55

ccc ctg tcc cct agc cgc cgc tcc ggg ctc tgc tcg ccc tcc tac gtt      783
Pro Leu Ser Pro Ser Arg Arg Ser Gly Leu Cys Ser Pro Ser Tyr Val
60                  65                  70                  75

gcg gtc aca ccc ttc tcc ctt cgg gga gac aac gac ggc ggt ggc ggg      831
Ala Val Thr Pro Phe Ser Leu Arg Gly Asp Asn Asp Gly Gly Gly Gly
                80                  85                  90

agc ttc tcc acg gcc gac cag ctg gag atg gtg acc gag ctg ctg gga      879
Ser Phe Ser Thr Ala Asp Gln Leu Glu Met Val Thr Glu Leu Leu Gly
            95                  100                 105

gga gac atg gtg aac cag agt ttc atc tgc gac ccg gac gac gag acc      927
Gly Asp Met Val Asn Gln Ser Phe Ile Cys Asp Pro Asp Asp Glu Thr
        110                 115                 120

ttc atc aaa aac atc atc atc cag gac tgt atg tgg agc ggc ttc tcg      975
Phe Ile Lys Asn Ile Ile Ile Gln Asp Cys Met Trp Ser Gly Phe Ser
    125                 130                 135

gcc gcc gcc aag ctc gtc tca gag aag ctg gcc tcc tac cag gct gcg     1023
Ala Ala Ala Lys Leu Val Ser Glu Lys Leu Ala Ser Tyr Gln Ala Ala
140                 145                 150                 155

cgc aaa gac agc ggc agc ccg aac ccc gcc cgc ggc cac agc gtc tgc     1071
Arg Lys Asp Ser Gly Ser Pro Asn Pro Ala Arg Gly His Ser Val Cys
                160                 165                 170

tcc acc tcc agc ttg tac ctg cag gat ctg agc gcc gcc gcc tca gag     1119
Ser Thr Ser Ser Leu Tyr Leu Gln Asp Leu Ser Ala Ala Ala Ser Glu
            175                 180                 185

tgc atc gac ccc tcg gtg gtc ttc ccc tac cct ctc aac gac agc agc     1167
Cys Ile Asp Pro Ser Val Val Phe Pro Tyr Pro Leu Asn Asp Ser Ser
        190                 195                 200

tcg ccc aag tcc tgc gcc tcg caa gac tcc agc gcc ttc tct ccg tcc     1215
Ser Pro Lys Ser Cys Ala Ser Gln Asp Ser Ser Ala Phe Ser Pro Ser
    205                 210                 215

tcg gat tct ctg ctc tcc tcg acg gag tcc tcc ccg cag ggc agc ccc     1263
Ser Asp Ser Leu Leu Ser Ser Thr Glu Ser Ser Pro Gln Gly Ser Pro
220                 225                 230                 235

gag ccc ctg gtg ctc cat gag gag aca ccg ccc acc acc agc agc gac     1311
Glu Pro Leu Val Leu His Glu Glu Thr Pro Pro Thr Thr Ser Ser Asp
                240                 245                 250

tct gag gag gaa caa gaa gat gag gaa gaa atc gat gtt gtt tct gtg     1359
Ser Glu Glu Glu Gln Glu Asp Glu Glu Glu Ile Asp Val Val Ser Val
            255                 260                 265

gaa aag agg cag gct cct ggc aaa agg tca gag tct gga tca cct tct     1407
Glu Lys Arg Gln Ala Pro Gly Lys Arg Ser Glu Ser Gly Ser Pro Ser
        270                 275                 280

gct gga ggc cac agc aaa cct cct cac agc cca ctg gtc ctc aag agg     1455
Ala Gly Gly His Ser Lys Pro Pro His Ser Pro Leu Val Leu Lys Arg
    285                 290                 295

tgc cac gtc tcc aca cat cag cac aac tac gca gcg cct ccc tcc act     1503
Cys His Val Ser Thr His Gln His Asn Tyr Ala Ala Pro Pro Ser Thr
300                 305                 310                 315

cgg aag gac tat cct gct gcc aag agg gtc aag ttg gac agt gtc aga     1551
Arg Lys Asp Tyr Pro Ala Ala Lys Arg Val Lys Leu Asp Ser Val Arg
                320                 325                 330
```

```
gtc ctg aga cag atc agc aac aac cga aaa tgc acc agc ccc agg tcc     1599
Val Leu Arg Gln Ile Ser Asn Asn Arg Lys Cys Thr Ser Pro Arg Ser
            335                 340                 345

tcg gac acc gag gag aat gtc aag agg cga aca cac aac gtc ttg gag     1647
Ser Asp Thr Glu Glu Asn Val Lys Arg Arg Thr His Asn Val Leu Glu
        350                 355                 360

cgc cag agg agg aac gag cta aaa cgg agc ttt ttt gcc ctg cgt gac     1695
Arg Gln Arg Arg Asn Glu Leu Lys Arg Ser Phe Phe Ala Leu Arg Asp
    365                 370                 375

cag atc ccg gag ttg gaa aac aat gaa aag gcc ccc aag gta gtt atc     1743
Gln Ile Pro Glu Leu Glu Asn Asn Glu Lys Ala Pro Lys Val Val Ile
380                 385                 390                 395

ctt aaa aaa gcc aca gca tac atc ctg tcc gtc caa gca gag gag caa     1791
Leu Lys Lys Ala Thr Ala Tyr Ile Leu Ser Val Gln Ala Glu Glu Gln
                400                 405                 410

aag ctc att tct gaa gag gac ttg ttg cgg aaa cga cga gaa cag ttg     1839
Lys Leu Ile Ser Glu Glu Asp Leu Leu Arg Lys Arg Arg Glu Gln Leu
            415                 420                 425

aaa cac aaa ctt gaa cag cta cgg aac tct tgt gcg taa ggaaaagtaa      1888
Lys His Lys Leu Glu Gln Leu Arg Asn Ser Cys Ala
        430                 435

ggaaaacgat tccttctaac agaaatgtcc tgagcaatca cctatgaact tgtttcaaat   1948

gcatgatcaa atgcaacctc acaaccttgg ctgagtcttg agactgaaag atttagccat   2008

aatgtaaact gcctcaaatt ggactttggg cataaaagaa ctttttatg cttaccatct    2068

ttttttttc tttaacagat ttgtatttaa gaattgtttt taaaaaattt taa           2121


<210> SEQ ID NO 18
<211> LENGTH: 439
<212> TYPE: PRT
<213> ORGANISM: homo sapiens

<400> SEQUENCE: 18

Met Pro Leu Asn Val Ser Phe Thr Asn Arg Asn Tyr Asp Leu Asp Tyr
1               5                   10                  15

Asp Ser Val Gln Pro Tyr Phe Tyr Cys Asp Glu Glu Glu Asn Phe Tyr
            20                  25                  30

Gln Gln Gln Gln Gln Ser Glu Leu Gln Pro Pro Ala Pro Ser Glu Asp
        35                  40                  45

Ile Trp Lys Lys Phe Glu Leu Leu Pro Thr Pro Pro Leu Ser Pro Ser
    50                  55                  60

Arg Arg Ser Gly Leu Cys Ser Pro Ser Tyr Val Ala Val Thr Pro Phe
65                  70                  75                  80

Ser Leu Arg Gly Asp Asn Asp Gly Gly Gly Gly Ser Phe Ser Thr Ala
                85                  90                  95

Asp Gln Leu Glu Met Val Thr Glu Leu Leu Gly Gly Asp Met Val Asn
            100                 105                 110

Gln Ser Phe Ile Cys Asp Pro Asp Asp Glu Thr Phe Ile Lys Asn Ile
        115                 120                 125

Ile Ile Gln Asp Cys Met Trp Ser Gly Phe Ser Ala Ala Ala Lys Leu
    130                 135                 140

Val Ser Glu Lys Leu Ala Ser Tyr Gln Ala Ala Arg Lys Asp Ser Gly
145                 150                 155                 160

Ser Pro Asn Pro Ala Arg Gly His Ser Val Cys Ser Thr Ser Ser Leu
                165                 170                 175

Tyr Leu Gln Asp Leu Ser Ala Ala Ala Ser Glu Cys Ile Asp Pro Ser
```

```
            180                 185                 190

Val Val Phe Pro Tyr Pro Leu Asn Asp Ser Ser Ser Pro Lys Ser Cys
        195                 200                 205

Ala Ser Gln Asp Ser Ser Ala Phe Ser Pro Ser Ser Asp Ser Leu Leu
    210                 215                 220

Ser Ser Thr Glu Ser Ser Pro Gln Gly Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Ala
            260                 265                 270

Pro Gly Lys Arg Ser Glu Ser Gly Ser Pro Ser Ala Gly Gly His Ser
        275                 280                 285

Lys Pro Pro His Ser Pro Leu Val Leu Lys Arg Cys His Val Ser Thr
    290                 295                 300

His Gln His Asn Tyr Ala Ala Pro Pro Ser Thr Arg Lys Asp Tyr Pro
305                 310                 315                 320

Ala Ala Lys Arg Val Lys Leu Asp Ser Val Arg Val Leu Arg Gln Ile
                325                 330                 335

Ser Asn Asn Arg Lys Cys Thr Ser Pro Arg Ser Ser Asp Thr Glu Glu
            340                 345                 350

Asn Val Lys Arg Arg Thr His Asn Val Leu Glu Arg Gln Arg Arg Asn
        355                 360                 365

Glu Leu Lys Arg Ser Phe Phe Ala Leu Arg Asp Gln Ile Pro Glu Leu
    370                 375                 380

Glu Asn Asn Glu Lys Ala Pro Lys Val Val Ile Leu Lys Lys Ala Thr
385                 390                 395                 400

Ala Tyr Ile Leu Ser Val Gln Ala Glu Glu Gln Lys Leu Ile Ser Glu
                405                 410                 415

Glu Asp Leu Leu Arg Lys Arg Arg Glu Gln Leu Lys His Lys Leu Glu
            420                 425                 430

Gln Leu Arg Asn Ser Cys Ala
        435


<210> SEQ ID NO 19
<211> LENGTH: 1641
<212> TYPE: DNA
<213> ORGANISM: homo sapiens
<220> FEATURE:
<221> NAME/KEY: CDS
<222> LOCATION: (166)..(1110)

<400> SEQUENCE: 19

ctccctgtgt tggtggagga tgtctgcagc agcatttaaa ttctgggagg gcttggttgt      60

cagcagcagc aggaggaggc agagcacagc atcgtcggga ccagactcgt ctcaggccag     120

ttgcagcctt ctcagccaaa cgccgaccaa ggaaaactca ctacc atg aga att gca     177
                                                  Met Arg Ile Ala
                                                  1

gtg att tgc ttt tgc ctc cta ggc atc acc tgt gcc ata cca gtt aaa       225
Val Ile Cys Phe Cys Leu Leu Gly Ile Thr Cys Ala Ile Pro Val Lys
5                   10                  15                  20

cag gct gat tct gga agt tct gag gaa aag cag ctt tac aac aaa tac       273
Gln Ala Asp Ser Gly Ser Ser Glu Glu Lys Gln Leu Tyr Asn Lys Tyr
                25                  30                  35

cca gat gct gtg gcc aca tgg cta aac cct gac cca tct cag aag cag       321
Pro Asp Ala Val Ala Thr Trp Leu Asn Pro Asp Pro Ser Gln Lys Gln
```

```
            40                  45                  50

aat ctc cta gcc cca cag aat gct gtg tcc tct gaa gaa acc aat gac      369
Asn Leu Leu Ala Pro Gln Asn Ala Val Ser Ser Glu Glu Thr Asn Asp
        55                  60                  65

ttt aaa caa gag acc ctt cca agt aag tcc aac gaa agc cat gac cac      417
Phe Lys Gln Glu Thr Leu Pro Ser Lys Ser Asn Glu Ser His Asp His
    70                  75                  80

atg gat gat atg gat gat gaa gat gat gat gac cat gtg gac agc cag      465
Met Asp Asp Met Asp Asp Glu Asp Asp Asp Asp His Val Asp Ser Gln
85                  90                  95                  100

gac tcc att gac tcg aac gac tct gat gat gta gat gac act gat gat      513
Asp Ser Ile Asp Ser Asn Asp Ser Asp Asp Val Asp Asp Thr Asp Asp
                105                 110                 115

tct cac cag tct gat gag tct cac cat tct gat gaa tct gat gaa ctg      561
Ser His Gln Ser Asp Glu Ser His His Ser Asp Glu Ser Asp Glu Leu
            120                 125                 130

gtc act gat ttt ccc acg gac ctg cca gca acc gaa gtt ttc act cca      609
Val Thr Asp Phe Pro Thr Asp Leu Pro Ala Thr Glu Val Phe Thr Pro
        135                 140                 145

gtt gtc ccc aca gta gac aca tat gat ggc cga ggt gat agt gtg gtt      657
Val Val Pro Thr Val Asp Thr Tyr Asp Gly Arg Gly Asp Ser Val Val
    150                 155                 160

tat gga ctg agg tca aaa tct aag aag ttt cgc aga cct gac atc cag      705
Tyr Gly Leu Arg Ser Lys Ser Lys Lys Phe Arg Arg Pro Asp Ile Gln
165                 170                 175                 180

tac cct gat gct aca gac gag gac atc acc tca cac atg gaa agc gag      753
Tyr Pro Asp Ala Thr Asp Glu Asp Ile Thr Ser His Met Glu Ser Glu
                185                 190                 195

gag ttg aat ggt gca tac aag gcc atc ccc gtt gcc cag gac ctg aac      801
Glu Leu Asn Gly Ala Tyr Lys Ala Ile Pro Val Ala Gln Asp Leu Asn
            200                 205                 210

gcg cct tct gat tgg gac agc cgt ggg aag gac agt tat gaa acg agt      849
Ala Pro Ser Asp Trp Asp Ser Arg Gly Lys Asp Ser Tyr Glu Thr Ser
        215                 220                 225

cag ctg gat gac cag agt gct gaa acc cac agc cac aag cag tcc aga      897
Gln Leu Asp Asp Gln Ser Ala Glu Thr His Ser His Lys Gln Ser Arg
    230                 235                 240

tta tat aag cgg aaa gcc aat gat gag agc aat gag cat tcc gat gtg      945
Leu Tyr Lys Arg Lys Ala Asn Asp Glu Ser Asn Glu His Ser Asp Val
245                 250                 255                 260

att gat agt cag gaa ctt tcc aaa gtc agc cgt gaa ttc cac agc cat      993
Ile Asp Ser Gln Glu Leu Ser Lys Val Ser Arg Glu Phe His Ser His
                265                 270                 275

gaa ttt cac agc cat gaa gat atg ctg gtt gta gac ccc aaa agt aag     1041
Glu Phe His Ser His Glu Asp Met Leu Val Val Asp Pro Lys Ser Lys
            280                 285                 290

gaa gaa gat aaa cac ctg aaa ttt cgt att tct cat gaa tta gat agt     1089
Glu Glu Asp Lys His Leu Lys Phe Arg Ile Ser His Glu Leu Asp Ser
        295                 300                 305

gca tct tct gag gtc aat taa aaggagaaaa aatacaattt ctcactttgc       1140
Ala Ser Ser Glu Val Asn
    310

atttagtcaa aagaaaaaat gctttatagc aaaatgaaag agaacatgaa atgcttcttt   1200

ctcagtttat tggttgaatg tgtatctatt tgagtctgga aataactaat gtgtttgata   1260

attagtttag tttgtggctt catggaaact ccctgtaaac taaaagcttc agggttatgt   1320

ctatgttcat tctatagaag aaatgcaaac tatcactgta ttttaatatt tgttattctc   1380

tcatgaatag aaatttatgt agaagcaaac aaaatacttt tacccactta aaaagagaat   1440
```

```
ataacatttt atgtcactat aatcttttgt tttttaagtt agtgtatatt ttgttgtgat   1500

tatctttttg tggtgtgaat aaatctttta tcttgaatgt aataagaatt tggtggtgtc   1560

aattgcttat ttgttttccc acggttgtcc agcaattaat aaaacataac ctttttttact   1620

gcctaaaaaa aaaaaaaaaa a                                              1641


<210> SEQ ID NO 20
<211> LENGTH: 314
<212> TYPE: PRT
<213> ORGANISM: homo sapiens

<400> SEQUENCE: 20

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Asp Glu Asp Asp Asp Asp His
                85                  90                  95

Val Asp Ser Gln Asp Ser Ile Asp Ser Asn Asp Ser Asp Asp Val Asp
            100                 105                 110

Asp Thr Asp Asp Ser His Gln Ser Asp Glu Ser His His Ser Asp Glu
        115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg
                165                 170                 175

Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
        275                 280                 285

Pro Lys Ser Lys Glu Glu Asp Lys His Leu Lys Phe Arg Ile Ser His
    290                 295                 300

Glu Leu Asp Ser Ala Ser Ser Glu Val Asn
305                 310


<210> SEQ ID NO 21
```

```
<211> LENGTH: 2539
<212> TYPE: DNA
<213> ORGANISM: homo sapiens
<220> FEATURE:
<221> NAME/KEY: CDS
<222> LOCATION: (321)..(1793)

<400> SEQUENCE: 21

ggagtctctt gctctggttc ttgctgttcc tgctcctgct cccgccgctc cccgtcctgc      60

tcgcggaccc aggggcgccc acgccagtga atccctgttg ttactatcca tgccagcacc     120

agggcatctg tgtccgcttc ggccttgacc gctaccagtg tgactgcacc cgcacgggct     180

attccggccc caactgcacc atccctggcc tgtggacctg gctccggaat tcactgcggc     240

ccagcccctc tttcacccac ttcctgctca ctcacgggcg ctggttctgg gagtttgtca     300

atgccacctt catccgagag atg ctc atg cgc ctg gta ctc aca gtg cgc tcc     353
                      Met Leu Met Arg Leu Val Leu Thr Val Arg Ser
                      1               5                   10

aac ctt atc ccc agt ccc ccc acc tac aac tca gca cat gac tac atc      401
Asn Leu Ile Pro Ser Pro Pro Thr Tyr Asn Ser Ala His Asp Tyr Ile
            15                  20                  25

agc tgg gag tct ttc tcc aac gtg agc tat tac act cgt att ctg ccc      449
Ser Trp Glu Ser Phe Ser Asn Val Ser Tyr Tyr Thr Arg Ile Leu Pro
        30                  35                  40

tct gtg cct aaa gat tgc ccc aca ccc atg gga acc aaa ggg aag aag      497
Ser Val Pro Lys Asp Cys Pro Thr Pro Met Gly Thr Lys Gly Lys Lys
    45                  50                  55

cag ttg cca gat gcc cag ctc ctg gcc cgc cgc ttc ctg ctc agg agg      545
Gln Leu Pro Asp Ala Gln Leu Leu Ala Arg Arg Phe Leu Leu Arg Arg
60                  65                  70                  75

aag ttc ata cct gac ccc caa ggc acc aac ctc atg ttt gcc ttc ttt      593
Lys Phe Ile Pro Asp Pro Gln Gly Thr Asn Leu Met Phe Ala Phe Phe
                80                  85                  90

gca caa cac ttc acc cac cag ttc ttc aaa act tct ggc aag atg ggt      641
Ala Gln His Phe Thr His Gln Phe Phe Lys Thr Ser Gly Lys Met Gly
            95                  100                 105

cct ggc ttc acc aag gcc ttg ggc cat ggg gta gac ctc ggc cac att      689
Pro Gly Phe Thr Lys Ala Leu Gly His Gly Val Asp Leu Gly His Ile
        110                 115                 120

tat gga gac aat ctg gag cgt cag tat caa ctg cgg ctc ttt aag gat      737
Tyr Gly Asp Asn Leu Glu Arg Gln Tyr Gln Leu Arg Leu Phe Lys Asp
    125                 130                 135

ggg aaa ctc aag tac cag gtg ctg gat gga gaa atg tac ccg ccc tcg      785
Gly Lys Leu Lys Tyr Gln Val Leu Asp Gly Glu Met Tyr Pro Pro Ser
140                 145                 150                 155

gta gaa gag gcg cct gtg ttg atg cac tac ccc cga ggc atc ccg ccc      833
Val Glu Glu Ala Pro Val Leu Met His Tyr Pro Arg Gly Ile Pro Pro
                160                 165                 170

cag agc cag atg gct gtg ggc cag gag gtg ttt ggg ctg ctt cct ggg      881
Gln Ser Gln Met Ala Val Gly Gln Glu Val Phe Gly Leu Leu Pro Gly
            175                 180                 185

ctc atg ctg tat gcc acg ctc tgg cta cgt gag cac aac cgt gtg tgt      929
Leu Met Leu Tyr Ala Thr Leu Trp Leu Arg Glu His Asn Arg Val Cys
        190                 195                 200

gac ctg ctg aag gct gag cac ccc acc tgg ggc gat gag cag ctt ttc      977
Asp Leu Leu Lys Ala Glu His Pro Thr Trp Gly Asp Glu Gln Leu Phe
    205                 210                 215

cag acg acc cgc ctc atc ctc ata ggg gag acc atc aag att gtc atc     1025
Gln Thr Thr Arg Leu Ile Leu Ile Gly Glu Thr Ile Lys Ile Val Ile
220                 225                 230                 235
```

```
gag gag tac gtg cag cag ctg agt ggc tat ttc ctg cag ctg aaa ttt      1073
Glu Glu Tyr Val Gln Gln Leu Ser Gly Tyr Phe Leu Gln Leu Lys Phe
                240                 245                 250

gac cca gag ctg ctg ttc ggt gtc cag ttc caa tac cgc aac cgc att      1121
Asp Pro Glu Leu Leu Phe Gly Val Gln Phe Gln Tyr Arg Asn Arg Ile
            255                 260                 265

gcc atg gag ttc aac cat ctc tac cac tgg cac ccc ctc atg cct gac      1169
Ala Met Glu Phe Asn His Leu Tyr His Trp His Pro Leu Met Pro Asp
        270                 275                 280

tcc ttc aag gtg ggc tcc cag gag tac agc tac gag cag ttc ttg ttc      1217
Ser Phe Lys Val Gly Ser Gln Glu Tyr Ser Tyr Glu Gln Phe Leu Phe
    285                 290                 295

aac acc tcc atg ttg gtg gac tat ggg gtt gag gcc ctg gtg gat gcc      1265
Asn Thr Ser Met Leu Val Asp Tyr Gly Val Glu Ala Leu Val Asp Ala
300                 305                 310                 315

ttc tct cgc cag att gct ggc cgg atc ggt ggg ggc agg aac atg gac      1313
Phe Ser Arg Gln Ile Ala Gly Arg Ile Gly Gly Gly Arg Asn Met Asp
                320                 325                 330

cac cac atc ctg cat gtg gct gtg gat gtc atc agg gag tct cgg gag      1361
His His Ile Leu His Val Ala Val Asp Val Ile Arg Glu Ser Arg Glu
            335                 340                 345

atg cgg ctg cag ccc ttc aat gag tac cgc aag agg ttt ggc atg aaa      1409
Met Arg Leu Gln Pro Phe Asn Glu Tyr Arg Lys Arg Phe Gly Met Lys
        350                 355                 360

ccc tac acc tcc ttc cag gag ctc gta gga gag aag gag atg gca gca      1457
Pro Tyr Thr Ser Phe Gln Glu Leu Val Gly Glu Lys Glu Met Ala Ala
    365                 370                 375

gag ttg gag gaa ttg tat gga gac att gat gcg ttg gag ttc tac cct      1505
Glu Leu Glu Glu Leu Tyr Gly Asp Ile Asp Ala Leu Glu Phe Tyr Pro
380                 385                 390                 395

gga ctg ctt ctt gaa aag tgc cat cca aac tct atc ttt ggg gag agt      1553
Gly Leu Leu Leu Glu Lys Cys His Pro Asn Ser Ile Phe Gly Glu Ser
                400                 405                 410

atg ata gag att ggg gct ccc ttt tcc ctc aag ggt ctc cta ggg aat      1601
Met Ile Glu Ile Gly Ala Pro Phe Ser Leu Lys Gly Leu Leu Gly Asn
            415                 420                 425

ccc atc tgt tct ccg gag tac tgg aag ccg agc aca ttt ggc ggc gag      1649
Pro Ile Cys Ser Pro Glu Tyr Trp Lys Pro Ser Thr Phe Gly Gly Glu
        430                 435                 440

gtg ggc ttt aac att gtc aag acg gcc aca ctg aag aag ctg gtc tgc      1697
Val Gly Phe Asn Ile Val Lys Thr Ala Thr Leu Lys Lys Leu Val Cys
    445                 450                 455

ctc aac acc aag acc tgt ccc tac gtt tcc ttc cgt gtg ccg gat gcc      1745
Leu Asn Thr Lys Thr Cys Pro Tyr Val Ser Phe Arg Val Pro Asp Ala
460                 465                 470                 475

agt cag gat gat ggg cct gct gtg gag cga cca tcc aca gag ctc tga      1793
Ser Gln Asp Asp Gly Pro Ala Val Glu Arg Pro Ser Thr Glu Leu
                480                 485                 490

ggggcaggaa agcagcattc tggaggggag agctttgtgc ttgtcattcc agagtgctga   1853

ggccagggct gatggtctta aatgctcatt ttctggtttg gcatggtgag tgttggggtt   1913

gacatttaga actttaagtc tcacccatta tctggaatat tgtgattctg tttattcttc   1973

cagaatgctg aactccttgt tagcccttca gattgttagg agtggttctc atttggtctg   2033

ccagaatact gggttcttag ttgacaacct agaatgtcag atttctggtt gatttgtaac   2093

acagtcattc taggatgtgg agctactgat gaaatctgct agaaagttag gggttcttta   2153

ttttgcattc cagaatcttg actttctgat tggtgattca aagtgttgtg ttcctggctg   2213

atgatccaga acagtggctc gtatcccaaa tctgtcagca tctggctgtc tagaatgtgg   2273
```

```
atttgattca ttttcctgtt cagtgagata tcatagagac ggagatccta aggtccaaca   2333

agaatgcatt ccctgaatct gtgcctgcac tgagagggca aggaagtggg gtgttcttct   2393

tgggaccccc actaagaccc tggtctgagg atgtagagag aacaggtggg ctgtattcac   2453

gccattggtt ggaagctacc agagctctat ccccatccag gtcttgactc atggcagctg   2513

tttctcatga agctaataaa attcgc                                         2539


<210> SEQ ID NO 22
<211> LENGTH: 490
<212> TYPE: PRT
<213> ORGANISM: homo sapiens

<400> SEQUENCE: 22

Met Leu Met Arg Leu Val Leu Thr Val Arg Ser Asn Leu Ile Pro Ser
1               5                   10                  15

Pro Pro Thr Tyr Asn Ser Ala His Asp Tyr Ile Ser Trp Glu Ser Phe
            20                  25                  30

Ser Asn Val Ser Tyr Tyr Thr Arg Ile Leu Pro Ser Val Pro Lys Asp
        35                  40                  45

Cys Pro Thr Pro Met Gly Thr Lys Gly Lys Lys Gln Leu Pro Asp Ala
    50                  55                  60

Gln Leu Leu Ala Arg Arg Phe Leu Leu Arg Arg Lys Phe Ile Pro Asp
65                  70                  75                  80

Pro Gln Gly Thr Asn Leu Met Phe Ala Phe Phe Ala Gln His Phe Thr
                85                  90                  95

His Gln Phe Phe Lys Thr Ser Gly Lys Met Gly Pro Gly Phe Thr Lys
            100                 105                 110

Ala Leu Gly His Gly Val Asp Leu Gly His Ile Tyr Gly Asp Asn Leu
        115                 120                 125

Glu Arg Gln Tyr Gln Leu Arg Leu Phe Lys Asp Gly Lys Leu Lys Tyr
    130                 135                 140

Gln Val Leu Asp Gly Glu Met Tyr Pro Pro Ser Val Glu Glu Ala Pro
145                 150                 155                 160

Val Leu Met His Tyr Pro Arg Gly Ile Pro Pro Gln Ser Gln Met Ala
                165                 170                 175

Val Gly Gln Glu Val Phe Gly Leu Leu Pro Gly Leu Met Leu Tyr Ala
            180                 185                 190

Thr Leu Trp Leu Arg Glu His Asn Arg Val Cys Asp Leu Leu Lys Ala
        195                 200                 205

Glu His Pro Thr Trp Gly Asp Glu Gln Leu Phe Gln Thr Thr Arg Leu
    210                 215                 220

Ile Leu Ile Gly Glu Thr Ile Lys Ile Val Ile Glu Glu Tyr Val Gln
225                 230                 235                 240

Gln Leu Ser Gly Tyr Phe Leu Gln Leu Lys Phe Asp Pro Glu Leu Leu
                245                 250                 255

Phe Gly Val Gln Phe Gln Tyr Arg Asn Arg Ile Ala Met Glu Phe Asn
            260                 265                 270

His Leu Tyr His Trp His Pro Leu Met Pro Asp Ser Phe Lys Val Gly
        275                 280                 285

Ser Gln Glu Tyr Ser Tyr Glu Gln Phe Leu Phe Asn Thr Ser Met Leu
    290                 295                 300

Val Asp Tyr Gly Val Glu Ala Leu Val Asp Ala Phe Ser Arg Gln Ile
305                 310                 315                 320
```

```
Ala Gly Arg Ile Gly Gly Gly Arg Asn Met Asp His His Ile Leu His
                325                 330                 335

Val Ala Val Asp Val Ile Arg Glu Ser Arg Glu Met Arg Leu Gln Pro
            340                 345                 350

Phe Asn Glu Tyr Arg Lys Arg Phe Gly Met Lys Pro Tyr Thr Ser Phe
        355                 360                 365

Gln Glu Leu Val Gly Glu Lys Glu Met Ala Ala Glu Leu Glu Glu Leu
    370                 375                 380

Tyr Gly Asp Ile Asp Ala Leu Glu Phe Tyr Pro Gly Leu Leu Leu Glu
385                 390                 395                 400

Lys Cys His Pro Asn Ser Ile Phe Gly Glu Ser Met Ile Glu Ile Gly
                405                 410                 415

Ala Pro Phe Ser Leu Lys Gly Leu Leu Gly Asn Pro Ile Cys Ser Pro
            420                 425                 430

Glu Tyr Trp Lys Pro Ser Thr Phe Gly Gly Glu Val Gly Phe Asn Ile
        435                 440                 445

Val Lys Thr Ala Thr Leu Lys Lys Leu Val Cys Leu Asn Thr Lys Thr
    450                 455                 460

Cys Pro Tyr Val Ser Phe Arg Val Pro Asp Ala Ser Gln Asp Asp Gly
465                 470                 475                 480

Pro Ala Val Glu Arg Pro Ser Thr Glu Leu
                485                 490


<210> SEQ ID NO 23
<211> LENGTH: 3356
<212> TYPE: DNA
<213> ORGANISM: homo sapiens
<220> FEATURE:
<221> NAME/KEY: CDS
<222> LOCATION: (98)..(1912)

<400> SEQUENCE: 23

gtccaggaac tcctcagcag cgcctccttc agctccacag ccagacgccc tcagacagca      60

aagcctaccc ccgcgccgcg ccctgcccgc cgctgcg atg ctc gcc cgc gcc ctg      115
                                         Met Leu Ala Arg Ala Leu
                                         1               5

ctg ctg tgc gcg gtc ctg gcg ctc agc cat aca gca aat cct tgc tgt      163
Leu Leu Cys Ala Val Leu Ala Leu Ser His Thr Ala Asn Pro Cys Cys
            10                  15                  20

tcc cac cca tgt caa aac cga ggt gta tgt atg agt gtg gga ttt gac      211
Ser His Pro Cys Gln Asn Arg Gly Val Cys Met Ser Val Gly Phe Asp
        25                  30                  35

cag tat aag tgc gat tgt acc cgg aca gga ttc tat gga gaa aac tgc      259
Gln Tyr Lys Cys Asp Cys Thr Arg Thr Gly Phe Tyr Gly Glu Asn Cys
    40                  45                  50

tca aca ccg gaa ttt ttg aca aga ata aaa tta ttt ctg aaa ccc act      307
Ser Thr Pro Glu Phe Leu Thr Arg Ile Lys Leu Phe Leu Lys Pro Thr
55                  60                  65                  70

cca aac aca gtg cac tac ata ctt acc cac ttc aag gga ttt tgg aac      355
Pro Asn Thr Val His Tyr Ile Leu Thr His Phe Lys Gly Phe Trp Asn
                75                  80                  85

gtt gtg aat aac att ccc ttc ctt cga aat gca att atg agt tat gtg      403
Val Val Asn Asn Ile Pro Phe Leu Arg Asn Ala Ile Met Ser Tyr Val
            90                  95                  100

ttg aca tcc aga tca cat ttg att gac agt cca cca act tac aat gct      451
Leu Thr Ser Arg Ser His Leu Ile Asp Ser Pro Pro Thr Tyr Asn Ala
        105                 110                 115

gac tat ggc tac aaa agc tgg gaa gcc ttc tct aac ctc tcc tat tat      499
```

-continued

```
Asp Tyr Gly Tyr Lys Ser Trp Glu Ala Phe Ser Asn Leu Ser Tyr Tyr
    120                 125                 130

act aga gcc ctt cct cct gtg cct gat gat tgc ccg act ccc ttg ggt      547
Thr Arg Ala Leu Pro Pro Val Pro Asp Asp Cys Pro Thr Pro Leu Gly
135                 140                 145                 150

gtc aaa ggt aaa aag cag ctt cct gat tca aat gag att gtg gaa aaa      595
Val Lys Gly Lys Lys Gln Leu Pro Asp Ser Asn Glu Ile Val Glu Lys
                155                 160                 165

ttg ctt cta aga aga aag ttc atc cct gat ccc cag ggc tca aac atg      643
Leu Leu Leu Arg Arg Lys Phe Ile Pro Asp Pro Gln Gly Ser Asn Met
            170                 175                 180

atg ttt gca ttc ttt gcc cag cac ttc acg cat cag ttt ttc aag aca      691
Met Phe Ala Phe Phe Ala Gln His Phe Thr His Gln Phe Phe Lys Thr
        185                 190                 195

gat cat aag cga ggg cca gct ttc acc aac ggg ctg ggc cat ggg gtg      739
Asp His Lys Arg Gly Pro Ala Phe Thr Asn Gly Leu Gly His Gly Val
    200                 205                 210

gac tta aat cat att tac ggt gaa act ctg gct aga cag cgt aaa ctg      787
Asp Leu Asn His Ile Tyr Gly Glu Thr Leu Ala Arg Gln Arg Lys Leu
215                 220                 225                 230

cgc ctt ttc aag gat gga aaa atg aaa tat cag ata att gat gga gag      835
Arg Leu Phe Lys Asp Gly Lys Met Lys Tyr Gln Ile Ile Asp Gly Glu
                235                 240                 245

atg tat cct ccc aca gtc aaa gat act cag gca gag atg atc tac cct      883
Met Tyr Pro Pro Thr Val Lys Asp Thr Gln Ala Glu Met Ile Tyr Pro
            250                 255                 260

cct caa gtc cct gag cat cta cgg ttt gct gtg ggg cag gag gtc ttt      931
Pro Gln Val Pro Glu His Leu Arg Phe Ala Val Gly Gln Glu Val Phe
        265                 270                 275

ggt ctg gtg cct ggt ctg atg atg tat gcc aca atc tgg ctg cgg gaa      979
Gly Leu Val Pro Gly Leu Met Met Tyr Ala Thr Ile Trp Leu Arg Glu
    280                 285                 290

cac aac aga gta tgc gat gtg ctt aaa cag gag cat cct gaa tgg ggt     1027
His Asn Arg Val Cys Asp Val Leu Lys Gln Glu His Pro Glu Trp Gly
295                 300                 305                 310

gat gag cag ttg ttc cag aca agc agg cta ata ctg ata gga gag act     1075
Asp Glu Gln Leu Phe Gln Thr Ser Arg Leu Ile Leu Ile Gly Glu Thr
                315                 320                 325

att aag att gtg att gaa gat tat gtg caa cac ttg agt ggc tat cac     1123
Ile Lys Ile Val Ile Glu Asp Tyr Val Gln His Leu Ser Gly Tyr His
            330                 335                 340

ttc aaa ctg aaa ttt gac cca gaa cta ctt ttc aac aaa caa ttc cag     1171
Phe Lys Leu Lys Phe Asp Pro Glu Leu Leu Phe Asn Lys Gln Phe Gln
        345                 350                 355

tac caa aat cgt att gct gct gaa ttt aac acc ctc tat cac tgg cat     1219
Tyr Gln Asn Arg Ile Ala Ala Glu Phe Asn Thr Leu Tyr His Trp His
    360                 365                 370

ccc ctt ctg cct gac acc ttt caa att cat gac cag aaa tac aac tat     1267
Pro Leu Leu Pro Asp Thr Phe Gln Ile His Asp Gln Lys Tyr Asn Tyr
375                 380                 385                 390

caa cag ttt atc tac aac aac tct ata ttg ctg gaa cat gga att acc     1315
Gln Gln Phe Ile Tyr Asn Asn Ser Ile Leu Leu Glu His Gly Ile Thr
                395                 400                 405

cag ttt gtt gaa tca ttc acc agg caa att gct ggc agg gtt gct ggt     1363
Gln Phe Val Glu Ser Phe Thr Arg Gln Ile Ala Gly Arg Val Ala Gly
            410                 415                 420

ggt agg aat gtt cca ccc gca gta cag aaa gta tca cag gct tcc att     1411
Gly Arg Asn Val Pro Pro Ala Val Gln Lys Val Ser Gln Ala Ser Ile
        425                 430                 435
```

```
gac cag agc agg cag atg aaa tac cag tct ttt aat gag tac cgc aaa     1459
Asp Gln Ser Arg Gln Met Lys Tyr Gln Ser Phe Asn Glu Tyr Arg Lys
    440                 445                 450

cgc ttt atg ctg aag ccc tat gaa tca ttt gaa gaa ctt aca gga gaa     1507
Arg Phe Met Leu Lys Pro Tyr Glu Ser Phe Glu Glu Leu Thr Gly Glu
455                 460                 465                 470

aag gaa atg tct gca gag ttg gaa gca ctc tat ggt gac atc gat gct     1555
Lys Glu Met Ser Ala Glu Leu Glu Ala Leu Tyr Gly Asp Ile Asp Ala
                475                 480                 485

gtg gag ctg tat cct gcc ctt ctg gta gaa aag cct cgg cca gat gcc     1603
Val Glu Leu Tyr Pro Ala Leu Leu Val Glu Lys Pro Arg Pro Asp Ala
            490                 495                 500

atc ttt ggt gaa acc atg gta gaa gtt gga gca cca ttc tcc ttg aaa     1651
Ile Phe Gly Glu Thr Met Val Glu Val Gly Ala Pro Phe Ser Leu Lys
        505                 510                 515

gga ctt atg ggt aat gtt ata tgt tct cct gcc tac tgg aag cca agc     1699
Gly Leu Met Gly Asn Val Ile Cys Ser Pro Ala Tyr Trp Lys Pro Ser
    520                 525                 530

act ttt ggt gga gaa gtg ggt ttt caa atc atc aac act gcc tca att     1747
Thr Phe Gly Gly Glu Val Gly Phe Gln Ile Ile Asn Thr Ala Ser Ile
535                 540                 545                 550

cag tct ctc atc tgc aat aac gtg aag ggc tgt ccc ttt act tca ttc     1795
Gln Ser Leu Ile Cys Asn Asn Val Lys Gly Cys Pro Phe Thr Ser Phe
                555                 560                 565

agt gtt cca gat cca gag ctc att aaa aca gtc acc atc aat gca agt     1843
Ser Val Pro Asp Pro Glu Leu Ile Lys Thr Val Thr Ile Asn Ala Ser
            570                 575                 580

tct tcc cgc tcc gga cta gat gat atc aat ccc aca gta cta cta aaa     1891
Ser Ser Arg Ser Gly Leu Asp Asp Ile Asn Pro Thr Val Leu Leu Lys
        585                 590                 595

gaa cgt tcg act gaa ctg tag aagtctaatg atcatattta tttatttata        1942
Glu Arg Ser Thr Glu Leu
    600

tgaaccatgt ctattaattt aattatttaa taatatttat attaaactcc ttatgttact   2002

taacatcttc tgtaacagaa gtcagtactc ctgttgcgga gaaaggagtc atacttgtga   2062

agacttttat gtcactactc taaagatttt gctgttgctg ttaagtttgg aaaacagttt   2122

ttattctgtt ttataaacca gagagaaatg agttttgacg tctttttact tgaatttcaa   2182

cttatattat aagaacgaaa gtaaagatgt ttgaatactt aaacactgtc acaagatggc   2242

aaaatgctga aagtttttac actgtcgatg tttccaatgc atcttccatg atgcattaga   2302

agtaactaat gtttgaaatt ttaaagtact tttggttatt tttctgtcat caaacaaaaa   2362

caggtatcag tgcattatta aatgaatatt taaattagac attaccagta atttcatgtc   2422

tactttttaa aatcagcaat gaaacaataa tttgaaattt ctaaattcat agggtagaat   2482

cacctgtaaa agcttgtttg atttcttaaa gttattaaac ttgtacatat accaaaaaga   2542

agctgtcttg gatttaaatc tgtaaaatca gtagaaattt tactacaatt gcttgttaaa   2602

atattttata agtgatgttc ctttttcacc aagagtataa accttttag tgtgactgtt    2662

aaaacttcct tttaaatcaa aatgccaaat ttattaaggt ggtggagcca ctgcagtgtt   2722

atcttaaaat aagaatattt tgttgagata ttccagaatt tgtttatatg gctggtaaca   2782

tgtaaaatct atatcagcaa aagggtctac ctttaaaata agcaataaca aagaagaaaa   2842

ccaaattatt gttcaaattt aggtttaaac ttttgaagca aacttttttt tatccttgtg   2902

cactgcaggc ctggtactca gattttgcta tgaggttaat gaagtaccaa gctgtgcttg   2962

aataatgata tgttttctca gattttctgt tgtacagttt aatttagcag tccatatcac   3022
```

```
attgcaaaag tagcaatgac ctcataaaat acctcttcaa aatgcttaaa ttcatttcac   3082

acattaattt tatctcagtc ttgaagccaa ttcagtaggt gcattggaat caagcctggc   3142

tacctgcatg ctgttccttt tcttttcttc ttttagccat tttgctaaga gacacagtct   3202

tctcatcact tcgtttctcc tattttgttt tactagtttt aagatcagag ttcactttct   3262

ttggactctg cctatatttt cttacctgaa cttttgcaag ttttcaggta aacctcagct   3322

caggactgct atttagctcc tcttaagaag atta                               3356
```

<210> SEQ ID NO 24
<211> LENGTH: 604
<212> TYPE: PRT
<213> ORGANISM: homo sapiens

<400> SEQUENCE: 24

```
Met Leu Ala Arg Ala Leu Leu Leu Cys Ala Val Leu Ala Leu Ser His
1               5                   10                  15

Thr Ala Asn Pro Cys Cys Ser His Pro Cys Gln Asn Arg Gly Val Cys
            20                  25                  30

Met Ser Val Gly Phe Asp Gln Tyr Lys Cys Asp Cys Thr Arg Thr Gly
        35                  40                  45

Phe Tyr Gly Glu Asn Cys Ser Thr Pro Glu Phe Leu Thr Arg Ile Lys
    50                  55                  60

Leu Phe Leu Lys Pro Thr Pro Asn Thr Val His Tyr Ile Leu Thr His
65                  70                  75                  80

Phe Lys Gly Phe Trp Asn Val Val Asn Asn Ile Pro Phe Leu Arg Asn
                85                  90                  95

Ala Ile Met Ser Tyr Val Leu Thr Ser Arg Ser His Leu Ile Asp Ser
            100                 105                 110

Pro Pro Thr Tyr Asn Ala Asp Tyr Gly Tyr Lys Ser Trp Glu Ala Phe
        115                 120                 125

Ser Asn Leu Ser Tyr Tyr Thr Arg Ala Leu Pro Pro Val Pro Asp Asp
    130                 135                 140

Cys Pro Thr Pro Leu Gly Val Lys Gly Lys Lys Gln Leu Pro Asp Ser
145                 150                 155                 160

Asn Glu Ile Val Glu Lys Leu Leu Leu Arg Arg Lys Phe Ile Pro Asp
                165                 170                 175

Pro Gln Gly Ser Asn Met Met Phe Ala Phe Phe Ala Gln His Phe Thr
            180                 185                 190

His Gln Phe Phe Lys Thr Asp His Lys Arg Gly Pro Ala Phe Thr Asn
        195                 200                 205

Gly Leu Gly His Gly Val Asp Leu Asn His Ile Tyr Gly Glu Thr Leu
    210                 215                 220

Ala Arg Gln Arg Lys Leu Arg Leu Phe Lys Asp Gly Lys Met Lys Tyr
225                 230                 235                 240

Gln Ile Ile Asp Gly Glu Met Tyr Pro Pro Thr Val Lys Asp Thr Gln
                245                 250                 255

Ala Glu Met Ile Tyr Pro Pro Gln Val Pro Glu His Leu Arg Phe Ala
            260                 265                 270

Val Gly Gln Glu Val Phe Gly Leu Val Pro Gly Leu Met Met Tyr Ala
        275                 280                 285

Thr Ile Trp Leu Arg Glu His Asn Arg Val Cys Asp Val Leu Lys Gln
    290                 295                 300

Glu His Pro Glu Trp Gly Asp Glu Gln Leu Phe Gln Thr Ser Arg Leu
```

```
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
            340                 345                 350

Phe Asn Lys Gln Phe Gln Tyr Gln Asn Arg Ile Ala Ala Glu Phe Asn
        355                 360                 365

Thr Leu Tyr His Trp His Pro Leu Leu Pro Asp Thr Phe Gln Ile His
    370                 375                 380

Asp Gln Lys Tyr Asn Tyr Gln Gln Phe Ile Tyr Asn Asn Ser Ile Leu
385                 390                 395                 400

Leu Glu His Gly Ile Thr Gln Phe Val Glu Ser Phe Thr Arg Gln Ile
                405                 410                 415

Ala Gly Arg Val Ala Gly Gly Arg Asn Val Pro Pro Ala Val Gln Lys
            420                 425                 430

Val Ser Gln Ala Ser Ile Asp Gln Ser Arg Gln Met Lys Tyr Gln Ser
        435                 440                 445

Phe Asn Glu Tyr Arg Lys Arg Phe Met Leu Lys Pro Tyr Glu Ser Phe
    450                 455                 460

Glu Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
                485                 490                 495

Lys Pro Arg Pro Asp Ala Ile Phe Gly Glu Thr Met Val Glu Val Gly
            500                 505                 510

Ala Pro Phe Ser Leu Lys Gly Leu Met Gly Asn Val Ile Cys Ser Pro
        515                 520                 525

Ala Tyr Trp Lys Pro Ser Thr Phe Gly Gly Glu Val Gly Phe Gln Ile
    530                 535                 540

Ile Asn Thr Ala Ser Ile Gln Ser Leu Ile Cys Asn Asn Val Lys Gly
545                 550                 555                 560

Cys Pro Phe Thr Ser Phe Ser Val Pro Asp Pro Glu Leu Ile Lys Thr
                565                 570                 575

Val Thr Ile Asn Ala Ser Ser Ser Arg Ser Gly Leu Asp Asp Ile Asn
            580                 585                 590

Pro Thr Val Leu Leu Lys Glu Arg Ser Thr Glu Leu
        595                 600


<210> SEQ ID NO 25
<211> LENGTH: 10049
<212> TYPE: DNA
<213> ORGANISM: homo sapiens
<220> FEATURE:
<221> NAME/KEY: CDS
<222> LOCATION: (267)..(1673)

<400> SEQUENCE: 25

gcgccgcctc cttcggcgtt cgccccacgg accggcaggc ggcggaccgc ggcccaggct      60

gaagctcagg gccctgtctg ctctgtggac tcaacagttt gtggcaagac aagctcagaa     120

ctgagaagct gtcaccacag ttctggaggc tgggaagttc aagatcaaag tgccagcaga     180

ttcagtgtca tgtgaggacg tgcttcctgc ttcatagata agagtagctt ggagctcggc     240

ggcacaacca gcaccatctg gtcgcg atg gtg gac acg gaa agc cca ctc tgc      293
                             Met Val Asp Thr Glu Ser Pro Leu Cys
                             1               5
```

-continued

```
ccc ctc tcc cca ctc gag gcc ggc gat cta gag agc ccg tta tct gaa      341
Pro Leu Ser Pro Leu Glu Ala Gly Asp Leu Glu Ser Pro Leu Ser Glu
10                  15                  20                  25

gag ttc ctg caa gaa atg gga aac atc caa gag att tcg caa tcc atc      389
Glu Phe Leu Gln Glu Met Gly Asn Ile Gln Glu Ile Ser Gln Ser Ile
                30                  35                  40

ggc gag gat agt tct gga agc ttt ggc ttt acg gaa tac cag tat tta      437
Gly Glu Asp Ser Ser Gly Ser Phe Gly Phe Thr Glu Tyr Gln Tyr Leu
            45                  50                  55

gga agc tgt cct ggc tca gat ggc tcg gtc atc acg gac acg ctt tca      485
Gly Ser Cys Pro Gly Ser Asp Gly Ser Val Ile Thr Asp Thr Leu Ser
        60                  65                  70

cca gct tcg agc ccc tcc tcg gtg act tat cct gtg gtc ccc ggc agc      533
Pro Ala Ser Ser Pro Ser Ser Val Thr Tyr Pro Val Val Pro Gly Ser
    75                  80                  85

gtg gac gag tct ccc agt gga gca ttg aac atc gaa tgt aga atc tgc      581
Val Asp Glu Ser Pro Ser Gly Ala Leu Asn Ile Glu Cys Arg Ile Cys
90                  95                  100                 105

ggg gac aag gcc tca ggc tat cat tac gga gtc cac gcg tgt gaa ggc      629
Gly Asp Lys Ala Ser Gly Tyr His Tyr Gly Val His Ala Cys Glu Gly
                110                 115                 120

tgc aag ggc ttc ttt cgg cga acg att cga ctc aag ctg gtg tat gac      677
Cys Lys Gly Phe Phe Arg Arg Thr Ile Arg Leu Lys Leu Val Tyr Asp
            125                 130                 135

aag tgc gac cgc agc tgc aag atc cag aaa aag aac aga aac aaa tgc      725
Lys Cys Asp Arg Ser Cys Lys Ile Gln Lys Lys Asn Arg Asn Lys Cys
        140                 145                 150

cag tat tgt cga ttt cac aag tgc ctt tct gtc ggg atg tca cac aac      773
Gln Tyr Cys Arg Phe His Lys Cys Leu Ser Val Gly Met Ser His Asn
    155                 160                 165

gcg att cgt ttt gga cga atg cca aga tct gag aaa gca aaa ctg aaa      821
Ala Ile Arg Phe Gly Arg Met Pro Arg Ser Glu Lys Ala Lys Leu Lys
170                 175                 180                 185

gca gaa att ctt acc tgt gaa cat gac ata gaa gat tct gaa act gca      869
Ala Glu Ile Leu Thr Cys Glu His Asp Ile Glu Asp Ser Glu Thr Ala
                190                 195                 200

gat ctc aaa tct ctg gcc aag aga atc tac gag gcc tac ttg aag aac      917
Asp Leu Lys Ser Leu Ala Lys Arg Ile Tyr Glu Ala Tyr Leu Lys Asn
            205                 210                 215

ttc aac atg aac aag gtc aaa gcc cgg gtc atc ctc tca gga aag gcc      965
Phe Asn Met Asn Lys Val Lys Ala Arg Val Ile Leu Ser Gly Lys Ala
        220                 225                 230

agt aac aat cca cct ttt gtc ata cat gat atg gag aca ctg tgt atg     1013
Ser Asn Asn Pro Pro Phe Val Ile His Asp Met Glu Thr Leu Cys Met
    235                 240                 245

gct gag aag acg ctg gtg gcc aag ctg gtg gcc aat ggc atc cag aac     1061
Ala Glu Lys Thr Leu Val Ala Lys Leu Val Ala Asn Gly Ile Gln Asn
250                 255                 260                 265

aag gag gcg gag gtc cgc atc ttt cac tgc tgc cag tgc acg tca gtg     1109
Lys Glu Ala Glu Val Arg Ile Phe His Cys Cys Gln Cys Thr Ser Val
                270                 275                 280

gag acc gtc acg gag ctc acg gaa ttc gcc aag gcc atc cca ggc ttc     1157
Glu Thr Val Thr Glu Leu Thr Glu Phe Ala Lys Ala Ile Pro Gly Phe
            285                 290                 295

gca aac ttg gac ctg aac gat caa gtg aca ttg cta aaa tac gga gtt     1205
Ala Asn Leu Asp Leu Asn Asp Gln Val Thr Leu Leu Lys Tyr Gly Val
        300                 305                 310

tat gag gcc ata ttc gcc atg ctg tct tct gtg atg aac aaa gac ggg     1253
Tyr Glu Ala Ile Phe Ala Met Leu Ser Ser Val Met Asn Lys Asp Gly
    315                 320                 325
```

```
atg ctg gta gcg tat gga aat ggg ttt ata act cgt gaa ttc cta aaa     1301
Met Leu Val Ala Tyr Gly Asn Gly Phe Ile Thr Arg Glu Phe Leu Lys
330                 335                 340                 345

agc cta agg aaa ccg ttc tgt gat atc atg gaa ccc aag ttt gat ttt     1349
Ser Leu Arg Lys Pro Phe Cys Asp Ile Met Glu Pro Lys Phe Asp Phe
                350                 355                 360

gcc atg aag ttc aat gca ctg gaa ctg gat gac agt gat atc tcc ctt     1397
Ala Met Lys Phe Asn Ala Leu Glu Leu Asp Asp Ser Asp Ile Ser Leu
            365                 370                 375

ttt gtg gct gct atc att tgc tgt gga gat cgt cct ggc ctt cta aac     1445
Phe Val Ala Ala Ile Ile Cys Cys Gly Asp Arg Pro Gly Leu Leu Asn
        380                 385                 390

gta gga cac att gaa aaa atg cag gag ggt att gta cat gtg ctc aga     1493
Val Gly His Ile Glu Lys Met Gln Glu Gly Ile Val His Val Leu Arg
    395                 400                 405

ctc cac ctg cag agc aac cac ccg gac gat atc ttt ctc ttc cca aaa     1541
Leu His Leu Gln Ser Asn His Pro Asp Asp Ile Phe Leu Phe Pro Lys
410                 415                 420                 425

ctt ctt caa aaa atg gca gac ctc cgg cag ctg gtg acg gag cat gcg     1589
Leu Leu Gln Lys Met Ala Asp Leu Arg Gln Leu Val Thr Glu His Ala
                430                 435                 440

cag ctg gtg cag atc atc aag aag acg gag tcg gat gct gcg ctg cac     1637
Gln Leu Val Gln Ile Ile Lys Lys Thr Glu Ser Asp Ala Ala Leu His
            445                 450                 455

ccg cta ctg cag gag atc tac agg gac atg tac tga gttccttcag          1683
Pro Leu Leu Gln Glu Ile Tyr Arg Asp Met Tyr
        460                 465

atcagccaca ccttttccag gagttctgaa gctgacagca ctacaaagga gacgggggag   1743

cagcacgatt ttgcacaaat atccaccact ttaaccttag agcttggaca gtctgagctg   1803

taggtaaccg gcatattatt ccatatcttt gttttaacca gtacttctaa gagcatagaa   1863

ctcaaatgct gggggtaggt ggctaatctc aggactggga agattacggc gaattatgct   1923

caatggtctg attttaactc acccgatgtt aatcaatgca cattgcttta gatcacattc   1983

gtgatttacc atttaattaa ctggtaacct caaaattcgt ggcctgtctt cccattcacc   2043

ccgcttttga ctattgtgct cctttataat tctgaaaact aatcagcact ttttaacaat   2103

gtttataatc ctataagtct agatgtatcc aaaggtgaag tatgtaaaaa gcagcaaaat   2163

atttatttca aagacttcac ttctgtttcc tgaatctaaa gaaagacaac atgctgcttt   2223

ttaatcatag gatggagaat tttaaagaac tgtttgggcc aggcacagtc gctcatactt   2283

gtaatcccag cactttggga ggccgaggcg ggtggatcac aaggtcagca gatcgagacc   2343

atcctggcca acatggtgaa accctgtctc tactaaaaat acaaaaatta gccgggtgtg   2403

gtggcacatg cctgtaatcc cagctactcg ggaagctgag gcaggagaat tgcttgaacc   2463

agggagttgg aggttgcagt gagctaagac tgcaccactg cactccagcc tggtgacaga   2523

acgagactct gtcttaaaaa caaacaaaca aaaaaaaaat ctgttagata agctatcaaa   2583

atgcagctgt tgttttgttt ttggctcact gttttcgtgg ttgtaactaa tatgtggaaa   2643

ggcccatttc caggtttgcg tagaagagcc cagaaaacag agtctcaaga cccccgctct   2703

ggactgtcat aagctagcac ccgtggtaag cgggacgaga caagctcccg aagcccgcca   2763

gcttcctgct ccactcagct ccgtccagtc aacctgaacc cacccagtcc agctgtctgt   2823

gggaatggtg gtgttcttag ggacagactg acaccttact tgtcagtgtt cctccgggcc   2883

ccatttggca gctcccgtat cttttgttat gttgctttta aagatatgat gttttattgt   2943
```

-continued

```
tttaactctt ggtgacagta gatgctctct ggagcgcaga cgaggcacat gtgtcttcat   3003
agcctgggct gggtgggagc cagtcaccct gcggatcgag agagggggta gagtcttctt   3063
caaatggcag ttttacttca aatggcagat ttcacaagag ttggttattt tttacaatgg   3123
tttaggttgt taagtctcct ttgtatgtaa ggtagttttt tcaacatcta aatttttgt    3183
tttagccttc aaaaccaact taccaacctc agtccagctg ggaaggcagc gttgattatg   3243
gtagtttgtc aagaatatat ggacctggaa acactttctc tctctgtcca cctggtagat   3303
aaattgtcct gttgagaatt tttagatctg gactggaact gccaggacca ccgcctccag   3363
ggagtcgctg ggcacctgga ggtatcgtcg atgcctctcc cccatcttta gaaaatttgg   3423
ctcttctgag gtcattatta ttttaagaat gattaggatt gataagggtc ccatgaccag   3483
cattatgaaa atgcgagagt gggaaggaca cagtgtgaga cttccactag aaaaaagtga   3543
aagttagggt taggacatcc ttttttaaaa attacaaatt tagtccgttt tggtttttgt   3603
aatcaggcta ggcacagtgg ctcacacatg gaatcccagc actttgggag gccgaggtgg   3663
gaggatcact tgagcccagg agttcgagac cagcctaggc aacatagcaa gaccctgtct   3723
gtacacaaaa tttaaaaatt agttcatcgg ggtggcacac atcagtagtc ccagctactc   3783
tgcaggctga ggtgggagga ttgcttgaac ccaggaggtc gaggctgcag tgagctgtga   3843
tctcaccact gcattccagc ctgggtgaca gagttagatt ccaccctctc ccaccccggc   3903
aaaaaaaaaa aaaaaagatg caatcaaagg ggctgttggc cagcaatggc agcagcagcg   3963
gcgggcagtc tgcccaagtg tcttaggaac caaaagcaaa taaaagtgtt tccatatatg   4023
ccaccagcca agtggccatc ctaattcaga aagaagctag cctttgagtg tctgtcatgg   4083
tgcatccgtt tcagtattat ttcctaaaat gagaagcccc tgtgtcaaca agatccaggg   4143
gctggagccc aatgccaagc ctgtgttgtc cccagcgacc ctgcagctgc tcgctctgat   4203
gtaccctgtg ccattcaagg agatgtggtc caggaaagtg agcctcatgg ttttcagaga   4263
agtcattgtt ctgtttacat tttcataaaa cctgtttaaa atagctcccc gtctcaggct   4323
ttcagcagta acagtgagct gactggcaag ttcgatgtta gctcccggga cactcagcag   4383
cgatggtgag cattttggtt tccttaaggc ccagcaagac ttccagggac atctctggtg   4443
aagccagaat ggagacaccc gtgacctcag gctgaaagtc actcgacatt ggtctcttgt   4503
gttgataggg aaggaaatca ggcattccta tttctttaaa taacaaaacc actaattgcc   4563
actcaatgct ggaatatttt gggtcaccta atcatagatt tctcagggca tcaatactca   4623
aatataggct gattatgccc cagttcaaat gggaactatt aacagagtgc atttcttgct   4683
tgctgggttt caacagacat cagccaaaag aacaaaagag atgtcaggac agattccagg   4743
agtgtcggag cacatgtgtg gcacccgctc cctctggcag cgaatgtagg aagtcgccaa   4803
atttacccac tcttcaacaa gtcattgttt aaacacggtt tttcattttc tcaactttta   4863
atagcaaaaa gtgccaaagt cctcagagac ctaacagcct tggtctaccg tgctgaccag   4923
ggtgaaggca cggcgaggga ctcctcccag acgtgcctct tgtgtgccag ctggctgtgg   4983
ctcgggagca gacgcaggcc tctccattgt ccaggggagc ctggcggcgc atccctcctc   5043
tcccacctcc tggcacttcc agctgggtgt cccacatgtt ggattccgtc cccaccacac   5103
ttccagagac cggagaactg tgcagggcct aaggccgttt ggatgaattg tcaaaacaag   5163
atgcttccag ttacagcggc aggagcggga ctgggagcac gggctgacgg ctgctggtgc   5223
ctttcttccc acctcgcttg cctgtttccg cttgaccctt cctccagctc cgatgagaag   5283
agtataaagc atcttcctaa cgggtgtgtt tgctatacga acataatgga cgtgaagtgg   5343
```

```
ggcagaaacc cagaactcag cattcaagga tgcccaggag agctgtccct gttttaaaga   5403
gctgtgtttt gttttgtttc gcatttagag agcagacaag gcacccttct gctgcgctga   5463
tacgtttctt acactgggcc attttagacc cccagggaaa cagccttcct ggagcgttgt   5523
ctggaggttc cagggacagg gcagcctccc agagccgagc aagagctcaa ggtacaaatg   5583
agagatttgc tataccgtga gaagtcaaca acttagccac cacttccccg caatggacca   5643
tgtaacaaat acctcagcag gccctgcaaa aggccatgct agagctgagg cgcacagcct   5703
gtggcctctg tagttagggc aggtgggatg gagactcctt gagtgcacac acctgagcct   5763
gcccacacac aggggagcag catctcgtat gacgtctgga aggaacttcg gttgtgtaaa   5823
gggagccttg aagatacgtg caaaaggtgc taccccaatt tggtgaaact gacattgggc   5883
acgtcttggg cttaggagaa gcggccgatg gtcccggcct gcagtgacaa acccccctcc   5943
ccgcaccgcc cccagcaccc cctctcctct tcacctcttc ctgctggcca cgaggaagcc   6003
acttcctcag agagacccta ccagatgcgg atggaaacag atgcaccaaa gcaagccctg   6063
atgaaaccgc gacttcctaa ggtctgtctc ctctgaactt gcacctgggc ctctctgtgt   6123
ttggttccaa gcacttccca cctcaaactc ccattttcaa accactgtat ctctgcgcac   6183
atctgctact taccagccgc atacatgatg gagggttttt tggtcctgat ccagtggcca   6243
cacctgtctt tgaaatgtct cactgaactc cagttttaaa atagattcat tgcttcaaca   6303
cagcaagccc aatgcaccca gctaagactg gcttgaccga cagcctggcc tttggtgggg   6363
ggcttcctgg ggcctgggga aagctggcca ccttcaacag ctggtacctc ttcaacagtg   6423
tggcctttca aaatgcagat gccaccagga gaacatgccc acagctcacc acctatggat   6483
gccatggctc tgggcagctt tcaaagcagg ttcctgtggt ctcctcagct gtttgagggg   6543
gtaacagcaa atcagcctcc attttaaaat gaaaacacca gcctccagat gtagggcctg   6603
ctgggtgttg ctagccgctg gtccccaggc acggtgcact ttctccacct cctgcagcct   6663
ccctgttgtt tctagactct tgcacctggt gagtgcaagg ataggtgacc caggggcctg   6723
cagccttgtc ctcagctccc atctcctgga ctgccagcct caccctctgc agttagcatg   6783
gttggcctga tgcagggatc ccgagggatt actttttaga ccttctttca cattcagaaa   6843
agtagtatag attcaggaga ggcaagaaaa ttatgctgtc catagaagtc acccatgaag   6903
actgatgcca ccacctgaag gctcatgatt gttaaaaatg tccacgggaa cctctcgtcc   6963
acaggaggtt tgtctcaaca cttcccattt ttacggcatt ggcattgcca agcatgggga   7023
agtatctgct cttctcatgt taaaagtggc ccagcttttc ttaactcagt ccaagctgac   7083
ttgtttagct gcactggaat ttcttaccaa ccaaatattt gcatcgagca aagggggctg   7143
tgtgcacctc cctaatggca gcgatgatgg ctgctgtcat tcaagcccat cttcagacgt   7203
cacagtctgg aagtgaaatg tccacaaaca tctgtggcag aaaaggctat acggaccacc   7263
cagttgtgct gcagctttac agagcaagga agggttgtgg caaataaatg attaacctgc   7323
ctcgactgtg ctgagggcaa caaaggccat ctcaccaaag gattattcga tgccattaaa   7383
tcatcccgtg accttcctgc ttccgagtcc atggcctttg cccagggcat gtactcccct   7443
gagaggcctt ctgcctagaa agatctatga ctgggttcca aagttgaggc ctaggttttt   7503
gctgggattt agatattttc aggcaccatt ttgacagcat tcaggaaaac ggttattgac   7563
cccatagact agggtaagaa taaaggcaat aaatttggtc tgactcagaa tataggagat   7623
ccatatattt ctctggaaac cacagtgtac actaaaatgt gaaattgaag gttttgttaa   7683
```

```
aaagaaaaag ataatgagct tcatgctttg tttaattaca taatgatttc cattacgcta   7743

tttctgtgaa atgcagcagg ttcttaaacg ttatttcagt ggcatgggct ggaagcttat   7803

cacaaaaagc catgtgtgtg gccttatcag aacagaaaga gacaggctgg tgcccaaggc   7863

tgctgcctgc tccacctttt gccagctctg gacatctgag gacgtcccgg cagatctgga   7923

atggggccct caactgacca tttgcttctc agaatttcag tttgagacat gagaggtata   7983

atcagttact tttctccccc cagagaaacc cttttgtgag gggagaggag ctatggtatg   8043

tggttcagct gaaacacata caactgcatc cttttggagt cctttgccaa caaaaacaga   8103

ccaacagacc agatggtgtc catgttcaat atcatgtctt gatggacgca gctgatgacc   8163

tcaaatactt gagtggtctc atggctgtta gatggattat ttgaaaaaaa aaaaaaaaaa   8223

agagagaaaa aataattgat ttttacatca gagatagcaa actaagacct ggggaggggg   8283

gtcagctttt attttatttt attttttttta agtttgctag ttgggtcaaa tgtgaggagg   8343

agggagtcta cctgccacct cttctcttgc cctcttctg cccacacatc cagcatccaa   8403

aatccattca tttaatgaat tgataaagtg ccgtgcaaac tggtgcacaa acaggccccc   8463

agtccacgca gcctggctcc taggaaaagt ggtgaccggg cgtgggggg catgccgcag   8523

ccctgggaca cagtcgggca ccttccccgg acccccaggc cttggctgtg cctcaagtca   8583

gagagggtca gccttcaggc cccggagacg agtgactggc cgatcatttc acaataaaat   8643

cactcacttt tggcaacttc actttttta aggcacagtc agttcctttt ctcatgtacc   8703

tcacaaaaga tgaagaccat gtagtactct ttttggtaaa gttacagtgt tcatgttaaa   8763

tatcactttt ttctacattg tgtggtaaaa agaactacgt taatagctat atcttaaata   8823

ctgtgatttg actttttgaa aaatatccta atacaaatat tttactaact tacaatcact   8883

catttaataa gaaacatttg gattcttttg aaatcagtgt taattgactc atattcttaa   8943

aagcctggct cttgacccta ttggaaacac aaaggaagct gaaatcaaac atctaaaata   9003

cactgcgtac acgtgtgcgt gcacacacac acacacacac acacacacac agctcttcat   9063

ttctcctgag ccatgcagaa tttactttca atgtggaaat ctgttccctt taccacactg   9123

tatatgcaca gagcacaaga gaggctatct ctagtcactt ccaccagcga ggccttagac   9183

tccgtattag aggccaccga tttcatacaa cagtgtttcg ctaaagaccc ttcactattc   9243

ttgtttagta aatagctgtc tgctcttcag ggaactgtta cctatgggtt attaccaaag   9303

aacgctggca attggaaatg tcctgatgga aattctttgc acgtgccggt tctctggcat   9363

cctccaggtg gcccaaccca aagcagaaag cagaaaccac agaccccgtg agtctcccca   9423

taccttgttt ccaataactt ggcaaaactt cttggtgcat attggttaca ccctctggga   9483

ttcataatgc cattaggcta aaaccctaag agagagggtt gacagaaaca cacgcgagaa   9543

tgaggcagat cccagagcaa ggactgggcc cagactctcc acatgtgctc tactagtgag   9603

tgccttatac tctcagtatt ttggggctta cagcttctta tttgtgctaa aaaggtgcag   9663

ttccaaagta ggaactgcca cacaggcccc agcatcctct ctccaacttc atacctctct   9723

cctggtgggg ggagcgggca tccaggacct ccggaatcaa ggatgtgcag agaagagcga   9783

aagtaatttt tctagtcaca tgaactgatt ggttccaggc aattagaaaa tggctataaa   9843

ataaccttaa ttttaaaaaa aaatcttggg tcttcgtttt cctattagga gactgaactg   9903

accacatgta ttgatttata tcctgaatat atgggaactt ctgtgtttgg gatgtcctac   9963

tgtaagactg atgaatgtac agagttaatt tcagggtaca gttttgcctt aatggtttta  10023

aaaaataaac tattttttaa aatttt                                      10049
```

<210> SEQ ID NO 26
<211> LENGTH: 468
<212> TYPE: PRT
<213> ORGANISM: homo sapiens

<400> SEQUENCE: 26

```
Met Val Asp Thr Glu Ser Pro Leu Cys Pro Leu Ser Pro Leu Glu Ala
1               5                   10                  15

Gly Asp Leu Glu Ser Pro Leu Ser Glu Glu Phe Leu Gln Glu Met Gly
            20                  25                  30

Asn Ile Gln Glu Ile Ser Gln Ser Ile Gly Glu Asp Ser Ser Gly Ser
        35                  40                  45

Phe Gly Phe Thr Glu Tyr Gln Tyr Leu Gly Ser Cys Pro Gly Ser Asp
    50                  55                  60

Gly Ser Val Ile Thr Asp Thr Leu Ser Pro Ala Ser Ser Pro Ser Ser
65                  70                  75                  80

Val Thr Tyr Pro Val Val Pro Gly Ser Val Asp Glu Ser Pro Ser Gly
                85                  90                  95

Ala Leu Asn Ile Glu Cys Arg Ile Cys Gly Asp Lys Ala Ser Gly Tyr
            100                 105                 110

His Tyr Gly Val His Ala Cys Glu Gly Cys Lys Gly Phe Phe Arg Arg
        115                 120                 125

Thr Ile Arg Leu Lys Leu Val Tyr Asp Lys Cys Asp Arg Ser Cys Lys
    130                 135                 140

Ile Gln Lys Lys Asn Arg Asn Lys Cys Gln Tyr Cys Arg Phe His Lys
145                 150                 155                 160

Cys Leu Ser Val Gly Met Ser His Asn Ala Ile Arg Phe Gly Arg Met
                165                 170                 175

Pro Arg Ser Glu Lys Ala Lys Leu Lys Ala Glu Ile Leu Thr Cys Glu
            180                 185                 190

His Asp Ile Glu Asp Ser Glu Thr Ala Asp Leu Lys Ser Leu Ala Lys
        195                 200                 205

Arg Ile Tyr Glu Ala Tyr Leu Lys Asn Phe Asn Met Asn Lys Val Lys
    210                 215                 220

Ala Arg Val Ile Leu Ser Gly Lys Ala Ser Asn Asn Pro Pro Phe Val
225                 230                 235                 240

Ile His Asp Met Glu Thr Leu Cys Met Ala Glu Lys Thr Leu Val Ala
                245                 250                 255

Lys Leu Val Ala Asn Gly Ile Gln Asn Lys Glu Ala Glu Val Arg Ile
            260                 265                 270

Phe His Cys Cys Gln Cys Thr Ser Val Glu Thr Val Thr Glu Leu Thr
        275                 280                 285

Glu Phe Ala Lys Ala Ile Pro Gly Phe Ala Asn Leu Asp Leu Asn Asp
    290                 295                 300

Gln Val Thr Leu Leu Lys Tyr Gly Val Tyr Glu Ala Ile Phe Ala Met
305                 310                 315                 320

Leu Ser Ser Val Met Asn Lys Asp Gly Met Leu Val Ala Tyr Gly Asn
                325                 330                 335

Gly Phe Ile Thr Arg Glu Phe Leu Lys Ser Leu Arg Lys Pro Phe Cys
            340                 345                 350

Asp Ile Met Glu Pro Lys Phe Asp Phe Ala Met Lys Phe Asn Ala Leu
        355                 360                 365

Glu Leu Asp Asp Ser Asp Ile Ser Leu Phe Val Ala Ala Ile Ile Cys
```

```
    370                 375                 380

Cys Gly Asp Arg Pro Gly Leu Leu Asn Val Gly His Ile Glu Lys Met
385                 390                 395                 400

Gln Glu Gly Ile Val His Val Leu Arg Leu His Leu Gln Ser Asn His
                405                 410                 415

Pro Asp Asp Ile Phe Leu Phe Pro Lys Leu Leu Gln Lys Met Ala Asp
            420                 425                 430

Leu Arg Gln Leu Val Thr Glu His Ala Gln Leu Val Gln Ile Ile Lys
        435                 440                 445

Lys Thr Glu Ser Asp Ala Ala Leu His Pro Leu Leu Gln Glu Ile Tyr
    450                 455                 460

Arg Asp Met Tyr
465


<210> SEQ ID NO 27
<211> LENGTH: 2749
<212> TYPE: DNA
<213> ORGANISM: homo sapiens
<220> FEATURE:
<221> NAME/KEY: CDS
<222> LOCATION: (190)..(1854)

<400> SEQUENCE: 27

gagggctggc cagtgaggct cggcccgggg aaagtgaaag tttgcctggg tcctctcggc      60

gccagagccg ctctccgcat cccaggacag cggtgcggcc ctcggccggg gcgcccactc     120

cgcagcagcc agcgagcgag cgagcgagcg agggcggccg acgcgcccgg ccgggaccca     180

gctgcccgt atg acc gcg ccg ggc gcc gcc ggg cgc tgc cct ccc acg aca     231
          Met Thr Ala Pro Gly Ala Ala Gly Arg Cys Pro Pro Thr Thr
          1               5                   10

tgg ctg ggc tcc ctg ctg ttg ttg gtc tgt ctc ctg gcg agc agg agt      279
Trp Leu Gly Ser Leu Leu Leu Leu Val Cys Leu Leu Ala Ser Arg Ser
15                  20                  25                  30

atc acc gag gag gtg tcg gag tac tgt agc cac atg att ggg agt gga      327
Ile Thr Glu Glu Val Ser Glu Tyr Cys Ser His Met Ile Gly Ser Gly
                35                  40                  45

cac ctg cag tct ctg cag cgg ctg att gac agt cag atg gag acc tcg      375
His Leu Gln Ser Leu Gln Arg Leu Ile Asp Ser Gln Met Glu Thr Ser
            50                  55                  60

tgc caa att aca ttt gag ttt gta gac cag gaa cag ttg aaa gat cca      423
Cys Gln Ile Thr Phe Glu Phe Val Asp Gln Glu Gln Leu Lys Asp Pro
        65                  70                  75

gtg tgc tac ctt aag aag gca ttt ctc ctg gta caa gac ata atg gag      471
Val Cys Tyr Leu Lys Lys Ala Phe Leu Leu Val Gln Asp Ile Met Glu
    80                  85                  90

gac acc atg cgc ttc aga gat aac acc ccc aat gcc atc gcc att gtg      519
Asp Thr Met Arg Phe Arg Asp Asn Thr Pro Asn Ala Ile Ala Ile Val
95                  100                 105                 110

cag ctg cag gaa ctc tct ttg agg ctg aag agc tgc ttc acc aag gat      567
Gln Leu Gln Glu Leu Ser Leu Arg Leu Lys Ser Cys Phe Thr Lys Asp
                115                 120                 125

tat gaa gag cat gac aag gcc tgc gtc cga act ttc tat gag aca cct      615
Tyr Glu Glu His Asp Lys Ala Cys Val Arg Thr Phe Tyr Glu Thr Pro
            130                 135                 140

ctc cag ttg ctg gag aag gtc aag aat gtc ttt aat gaa aca aag aat      663
Leu Gln Leu Leu Glu Lys Val Lys Asn Val Phe Asn Glu Thr Lys Asn
        145                 150                 155

ctc ctt gac aag gac tgg aat att ttc agc aag aac tgc aac aac agc      711
Leu Leu Asp Lys Asp Trp Asn Ile Phe Ser Lys Asn Cys Asn Asn Ser
```

```
    160                 165                 170

ttt gct gaa tgc tcc agc caa gat gtg gtg acc aag cct gat tgc aac       759
Phe Ala Glu Cys Ser Ser Gln Asp Val Val Thr Lys Pro Asp Cys Asn
175                 180                 185                 190

tgc ctg tac ccc aaa gcc atc cct agc agt gac ccg gcc tct gtc tcc       807
Cys Leu Tyr Pro Lys Ala Ile Pro Ser Ser Asp Pro Ala Ser Val Ser
                195                 200                 205

cct cat cag ccc ctc gcc ccc tcc atg gcc cct gtg gct ggc ttg acc       855
Pro His Gln Pro Leu Ala Pro Ser Met Ala Pro Val Ala Gly Leu Thr
            210                 215                 220

tgg gag gac tct gag gga act gag ggc agc tcc ctc ttg cct ggt gag       903
Trp Glu Asp Ser Glu Gly Thr Glu Gly Ser Ser Leu Leu Pro Gly Glu
        225                 230                 235

cag ccc ctg cac aca gtg gat cca ggc agt gcc aag cag cgg cca ccc       951
Gln Pro Leu His Thr Val Asp Pro Gly Ser Ala Lys Gln Arg Pro Pro
    240                 245                 250

agg agc acc tgc cag agc ttt gag ccg cca gag acc cca gtt gtc aag       999
Arg Ser Thr Cys Gln Ser Phe Glu Pro Pro Glu Thr Pro Val Val Lys
255                 260                 265                 270

gac agc acc atc ggt ggc tca cca cag cct cgc ccc tct gtc ggg gcc      1047
Asp Ser Thr Ile Gly Gly Ser Pro Gln Pro Arg Pro Ser Val Gly Ala
                275                 280                 285

ttc aac ccc ggg atg gag gat att ctt gac tct gca atg ggc act aat      1095
Phe Asn Pro Gly Met Glu Asp Ile Leu Asp Ser Ala Met Gly Thr Asn
            290                 295                 300

tgg gtc cca gaa gaa gcc tct gga gag gcc agt gag att ccc gta ccc      1143
Trp Val Pro Glu Glu Ala Ser Gly Glu Ala Ser Glu Ile Pro Val Pro
        305                 310                 315

caa ggg aca gag ctt tcc ccc tcc agg cca gga ggg ggc agc atg cag      1191
Gln Gly Thr Glu Leu Ser Pro Ser Arg Pro Gly Gly Gly Ser Met Gln
    320                 325                 330

aca gag ccc gcc aga ccc agc aac ttc ctc tca gca tct tct cca ctc      1239
Thr Glu Pro Ala Arg Pro Ser Asn Phe Leu Ser Ala Ser Ser Pro Leu
335                 340                 345                 350

cct gca tca gca aag ggc caa cag ccg gca gat gta act ggt aca gcc      1287
Pro Ala Ser Ala Lys Gly Gln Gln Pro Ala Asp Val Thr Gly Thr Ala
                355                 360                 365

ttg ccc agg gtg ggc ccc gtg agg ccc act ggc cag gac tgg aat cac      1335
Leu Pro Arg Val Gly Pro Val Arg Pro Thr Gly Gln Asp Trp Asn His
            370                 375                 380

acc ccc cag aag aca gac cat cca tct gcc ctg ctc aga gac ccc ccg      1383
Thr Pro Gln Lys Thr Asp His Pro Ser Ala Leu Leu Arg Asp Pro Pro
        385                 390                 395

gag cca ggc tct ccc agg atc tca tca ctg cgc ccc cag ggc ctc agc      1431
Glu Pro Gly Ser Pro Arg Ile Ser Ser Leu Arg Pro Gln Gly Leu Ser
    400                 405                 410

aac ccc tcc acc ctc tct gct cag cca cag ctt tcc aga agc cac tcc      1479
Asn Pro Ser Thr Leu Ser Ala Gln Pro Gln Leu Ser Arg Ser His Ser
415                 420                 425                 430

tcg ggc agc gtg ctg ccc ctt ggg gag ctg gag ggc agg agg agc acc      1527
Ser Gly Ser Val Leu Pro Leu Gly Glu Leu Glu Gly Arg Arg Ser Thr
                435                 440                 445

agg gat cgg agg agc ccc gca gag cca gaa gga gga cca gca agt gaa      1575
Arg Asp Arg Arg Ser Pro Ala Glu Pro Glu Gly Gly Pro Ala Ser Glu
            450                 455                 460

ggg gca gcc agg ccc ctg ccc cgt ttt aac tcc gtt cct ttg act gac      1623
Gly Ala Ala Arg Pro Leu Pro Arg Phe Asn Ser Val Pro Leu Thr Asp
        465                 470                 475

aca ggc cat gag agg cag tcc gag gga tcc tcc agc ccg cag ctc cag      1671
```

```
Thr Gly His Glu Arg Gln Ser Glu Gly Ser Ser Ser Pro Gln Leu Gln
    480                 485                 490

gag tct gtc ttc cac ctg ctg gtg ccc agt gtc atc ctg gtc ttg ctg     1719
Glu Ser Val Phe His Leu Leu Val Pro Ser Val Ile Leu Val Leu Leu
495                 500                 505                 510

gcc gtc gga ggc ctc ttg ttc tac agg tgg agg cgg cgg agc cat caa     1767
Ala Val Gly Gly Leu Leu Phe Tyr Arg Trp Arg Arg Arg Ser His Gln
                515                 520                 525

gag cct cag aga gcg gat tct ccc ttg gag caa cca gag ggc agc ccc     1815
Glu Pro Gln Arg Ala Asp Ser Pro Leu Glu Gln Pro Glu Gly Ser Pro
            530                 535                 540

ctg act cag gat gac aga cag gtg gaa ctg cca gtg tag agggaattct      1864
Leu Thr Gln Asp Asp Arg Gln Val Glu Leu Pro Val
        545                 550

aagctggacg cacagaacag tctctccgtg ggaggagaca ttatggggcg tccaccacca   1924

cccctccctg gccatcctcc tggaatgtgg tctgccctcc accagagctc ctgcctgcca   1984

ggactggacc agagcagcca ggctggggcc cctctgtctc aacccgcaga cccttgactg   2044

aatgagagag gccagaggat gctccccatg ctgccactat ttattgtgag ccctggaggc   2104

tcccatgtgc ttgaggaagg ctggtgagcc cggctcagga ccctcttccc tcaggggctg   2164

caccctcctc tcactccctt ccatgccgga acccaggcca gggacccacc ggcctgtggt   2224

ttgtgggaaa gcagggtgga cgctgaggag tgaaagaacc ctgcacccag agggcctgcc   2284

tggtgccaag gtatcccagc ctggacaggc atggacctgt ctccagagag aggagcctga   2344

agttcgtggg gcgggacagc gtcggcctga tttcccgtaa aggtgtgcag cctgagagac   2404

gggaagagga ggcctctgga cctgctggtc tgcactgaca gcctgaaggg tctacaccct   2464

cggctcacct aagtgccctg tgctggttgc caggcgcaga ggggaggcca gccctgccct   2524

caggacctgc ctgacctgcc agtgatgcca agagggggat caagcactgg cctctgcccc   2584

tcctccttcc agcacctgcc agagcttctc caggaggcca agcagaggct cccctcatga   2644

aggaagccat tgcactgtga acactgtacc tgcctgctga acagcctgcc cccgtccatc   2704

catgagccag catccgtccg tcctccactc tccagcctct cccca                   2749


<210> SEQ ID NO 28
<211> LENGTH: 554
<212> TYPE: PRT
<213> ORGANISM: homo sapiens

<400> SEQUENCE: 28

Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
```

```
        115                 120                 125

Glu His Asp Lys Ala Cys Val Arg Thr Phe Tyr Glu Thr Pro Leu Gln
    130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
            180                 185                 190

Tyr Pro Lys Ala Ile Pro Ser Ser Asp Pro Ala Ser Val Ser Pro His
        195                 200                 205

Gln Pro Leu Ala Pro Ser Met Ala Pro Val Ala Gly Leu Thr Trp Glu
    210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255

Thr Cys Gln Ser Phe Glu Pro Pro Glu Thr Pro Val Val Lys Asp Ser
            260                 265                 270

Thr Ile Gly Gly Ser Pro Gln Pro Arg Pro Ser Val Gly Ala Phe Asn
        275                 280                 285

Pro Gly Met Glu Asp Ile Leu Asp Ser Ala Met Gly Thr Asn Trp Val
    290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
                325                 330                 335

Pro Ala Arg Pro Ser Asn Phe Leu Ser Ala Ser Ser Pro Leu Pro Ala
            340                 345                 350

Ser Ala Lys Gly Gln Gln Pro Ala Asp Val Thr Gly Thr Ala Leu Pro
        355                 360                 365

Arg Val Gly Pro Val Arg Pro Thr Gly Gln Asp Trp Asn His Thr Pro
    370                 375                 380

Gln Lys Thr Asp His Pro Ser Ala Leu Leu Arg Asp Pro Pro Glu Pro
385                 390                 395                 400

Gly Ser Pro Arg Ile Ser Ser Leu Arg Pro Gln Gly Leu Ser Asn Pro
                405                 410                 415

Ser Thr Leu Ser Ala Gln Pro Gln Leu Ser Arg Ser His Ser Ser Gly
            420                 425                 430

Ser Val Leu Pro Leu Gly Glu Leu Glu Gly Arg Arg Ser Thr Arg Asp
        435                 440                 445

Arg Arg Ser Pro Ala Glu Pro Glu Gly Gly Pro Ala Ser Glu Gly Ala
    450                 455                 460

Ala Arg Pro Leu Pro Arg Phe Asn Ser Val Pro Leu Thr Asp Thr Gly
465                 470                 475                 480

His Glu Arg Gln Ser Glu Gly Ser Ser Ser Pro Gln Leu Gln Glu Ser
                485                 490                 495

Val Phe His Leu Leu Val Pro Ser Val Ile Leu Val Leu Leu Ala Val
            500                 505                 510

Gly Gly Leu Leu Phe Tyr Arg Trp Arg Arg Arg Ser His Gln Glu Pro
        515                 520                 525

Gln Arg Ala Asp Ser Pro Leu Glu Gln Pro Glu Gly Ser Pro Leu Thr
    530                 535                 540
```

```
Gln Asp Asp Arg Gln Val Glu Leu Pro Val
545                 550


<210> SEQ ID NO 29
<211> LENGTH: 1325
<212> TYPE: DNA
<213> ORGANISM: homo sapiens
<220> FEATURE:
<221> NAME/KEY: CDS
<222> LOCATION: (145)..(1032)

<400> SEQUENCE: 29

gcagtagcag cgagcagcag agtccgcacg ctccggcgag gggcagaaga gcgcgaggga      60

gcgcggggca gcagaagcga gagccgagcg cggacccagc caggacccac agccctcccc     120

agctgcccag gaagagcccc agcc atg gaa cac cag ctc ctg tgc tgc gaa        171
                           Met Glu His Gln Leu Leu Cys Cys Glu
                           1               5

gtg gaa acc atc cgc cgc gcg tac ccc gat gcc aac ctc ctc aac gac       219
Val Glu Thr Ile Arg Arg Ala Tyr Pro Asp Ala Asn Leu Leu Asn Asp
10                  15                  20                  25

cgg gtg ctg cgg gcc atg ctg aag gcg gag gag acc tgc gcg ccc tcg       267
Arg Val Leu Arg Ala Met Leu Lys Ala Glu Glu Thr Cys Ala Pro Ser
                30                  35                  40

gtg tcc tac ttc aaa tgt gtg cag aag gag gtc ctg ccg tcc atg cgg       315
Val Ser Tyr Phe Lys Cys Val Gln Lys Glu Val Leu Pro Ser Met Arg
            45                  50                  55

aag atc gtc gcc acc tgg atg ctg gag gtc tgc gag gaa cag aag tgc       363
Lys Ile Val Ala Thr Trp Met Leu Glu Val Cys Glu Glu Gln Lys Cys
        60                  65                  70

gag gag gag gtc ttc ccg ctg gcc atg aac tac ctg gac cgc ttc ctg       411
Glu Glu Glu Val Phe Pro Leu Ala Met Asn Tyr Leu Asp Arg Phe Leu
    75                  80                  85

tcg ctg gag ccc gtg aaa aag agc cgc ctg cag ctg ctg ggg gcc act       459
Ser Leu Glu Pro Val Lys Lys Ser Arg Leu Gln Leu Leu Gly Ala Thr
90                  95                  100                 105

tgc atg ttc gtg gcc tct aag atg aag gag acc atc ccc ctg acg gcc       507
Cys Met Phe Val Ala Ser Lys Met Lys Glu Thr Ile Pro Leu Thr Ala
                110                 115                 120

gag aag ctg tgc atc tac acc gac ggc tcc atc cgg ccc gag gag ctg       555
Glu Lys Leu Cys Ile Tyr Thr Asp Gly Ser Ile Arg Pro Glu Glu Leu
            125                 130                 135

ctg caa atg gag ctg ctc ctg gtg aac aag ctc aag tgg aac ctg gcc       603
Leu Gln Met Glu Leu Leu Leu Val Asn Lys Leu Lys Trp Asn Leu Ala
        140                 145                 150

gca atg acc ccg cac gat ttc att gaa cac ttc ctc tcc aaa atg cca       651
Ala Met Thr Pro His Asp Phe Ile Glu His Phe Leu Ser Lys Met Pro
    155                 160                 165

gag gcg gag gag aac aaa cag atc atc cgc aaa cac gcg cag acc ttc       699
Glu Ala Glu Glu Asn Lys Gln Ile Ile Arg Lys His Ala Gln Thr Phe
170                 175                 180                 185

gtt gcc tct tgt gcc aca gat gtg aag ttc att tcc aat ccg ccc tcc       747
Val Ala Ser Cys Ala Thr Asp Val Lys Phe Ile Ser Asn Pro Pro Ser
                190                 195                 200

atg gtg gca gcg ggg agc gtg gtg gcc gca gtg caa ggc ctg aac ctg       795
Met Val Ala Ala Gly Ser Val Val Ala Ala Val Gln Gly Leu Asn Leu
            205                 210                 215

agg agc ccc aac aac ttc ctg tcc tac tac cgc ctc aca cgc ttc ctc       843
Arg Ser Pro Asn Asn Phe Leu Ser Tyr Tyr Arg Leu Thr Arg Phe Leu
        220                 225                 230
```

```
tcc aga gtg atc aag tgt gac cca gac tgc ctc cgg gcc tgc cag gag      891
Ser Arg Val Ile Lys Cys Asp Pro Asp Cys Leu Arg Ala Cys Gln Glu
    235                 240                 245

cag atc gaa gcc ctg ctg gag tca agc ctg cgc cag gcc cag cag aac      939
Gln Ile Glu Ala Leu Leu Glu Ser Ser Leu Arg Gln Ala Gln Gln Asn
250                 255                 260                 265

atg gac ccc aag gcc gcc gag gag gag gaa gag gag gag gag gag gtg      987
Met Asp Pro Lys Ala Ala Glu Glu Glu Glu Glu Glu Glu Glu Glu Val
                270                 275                 280

gac ctg gct tgc aca ccc acc gac gtg cgg gac gtg gac atc tga         1032
Asp Leu Ala Cys Thr Pro Thr Asp Val Arg Asp Val Asp Ile
            285                 290                 295

ggggcccagg caggcgggcg ccaccgccac ccgcagcgag ggcggagccg gccccaggtg   1092

ctccacatga cagtccctcc tctccggagc attttgatac cagaagggaa agcttcattc   1152

tccttgttgt tggttgtttt ttcctttgct ctttccccct tccatctctg acttaagcaa   1212

aagaaaaaga ttacccaaaa actgtcttta aaagagagag agagaaaaaa aaaaaaaaaa   1272

aaaaaaaaaa aaaaaaaaaa aaaaaaaaaa aaaaaaaaaa aaaaaaaaaa aaa          1325


<210> SEQ ID NO 30
<211> LENGTH: 295
<212> TYPE: PRT
<213> ORGANISM: homo sapiens

<400> SEQUENCE: 30

Met Glu His Gln Leu Leu Cys Cys Glu Val Glu Thr Ile Arg Arg Ala
1               5                   10                  15

Tyr Pro Asp Ala Asn Leu Leu Asn Asp Arg Val Leu Arg Ala Met Leu
            20                  25                  30

Lys Ala Glu Glu Thr Cys Ala Pro Ser Val Ser Tyr Phe Lys Cys Val
        35                  40                  45

Gln Lys Glu Val Leu Pro Ser Met Arg Lys Ile Val Ala Thr Trp Met
    50                  55                  60

Leu Glu Val Cys Glu Glu Gln Lys Cys Glu Glu Glu Val Phe Pro Leu
65                  70                  75                  80

Ala Met Asn Tyr Leu Asp Arg Phe Leu Ser Leu Glu Pro Val Lys Lys
                85                  90                  95

Ser Arg Leu Gln Leu Leu Gly Ala Thr Cys Met Phe Val Ala Ser Lys
            100                 105                 110

Met Lys Glu Thr Ile Pro Leu Thr Ala Glu Lys Leu Cys Ile Tyr Thr
        115                 120                 125

Asp Gly Ser Ile Arg Pro Glu Glu Leu Leu Gln Met Glu Leu Leu Leu
    130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Glu Asn Lys Gln
                165                 170                 175

Ile Ile Arg Lys His Ala Gln Thr Phe Val Ala Ser Cys Ala Thr Asp
            180                 185                 190

Val Lys Phe Ile Ser Asn Pro Pro Ser Met Val Ala Ala Gly Ser Val
        195                 200                 205

Val Ala Ala Val Gln Gly Leu Asn Leu Arg Ser Pro Asn Asn Phe Leu
    210                 215                 220

Ser Tyr Tyr Arg Leu Thr Arg Phe Leu Ser Arg Val Ile Lys Cys Asp
225                 230                 235                 240
```

```
Pro Asp Cys Leu Arg Ala Cys Gln Glu Gln Ile Glu Ala Leu Leu Glu
                245                 250                 255

Ser Ser Leu Arg Gln Ala Gln Gln Asn Met Asp Pro Lys Ala Ala Glu
            260                 265                 270

Glu Glu Glu Glu Glu Glu Glu Glu Val Asp Leu Ala Cys Thr Pro Thr
        275                 280                 285

Asp Val Arg Asp Val Asp Ile
    290                 295


<210> SEQ ID NO 31
<211> LENGTH: 716
<212> TYPE: DNA
<213> ORGANISM: homo sapiens
<220> FEATURE:
<221> NAME/KEY: CDS
<222> LOCATION: (224)..(592)

<400> SEQUENCE: 31

aggctcagta taaatagcag ccaccgctcc ctggcaggca gggacccgca gctcagctac      60

agcacagatc aggtgaggag cacaccaagg agtgattttt aaaacttact ctgttttctc     120

tttcccaaca agattatcat ttcctttaaa aaaaatagtt atcctggggc atacagccat     180

accattctga aggtgtctta tctcctctga tctagagagc acc atg aag ctt ctc       235
                                                Met Lys Leu Leu
                                                1

acg ggc ctg gtt ttc tgc tcc ttg gtc ctg ggt gtc agc agc cga agc       283
Thr Gly Leu Val Phe Cys Ser Leu Val Leu Gly Val Ser Ser Arg Ser
5                   10                  15                  20

ttc ttt tcg ttc ctt ggc gag gct ttt gat ggg gct cgg gac atg tgg       331
Phe Phe Ser Phe Leu Gly Glu Ala Phe Asp Gly Ala Arg Asp Met Trp
                25                  30                  35

aga gcc tac tct gac atg aga gaa gcc aat tac atc ggc tca gac aaa       379
Arg Ala Tyr Ser Asp Met Arg Glu Ala Asn Tyr Ile Gly Ser Asp Lys
            40                  45                  50

tac ttc cat gct cgg ggg aac tat gat gct gcc aaa agg gga cct ggg       427
Tyr Phe His Ala Arg Gly Asn Tyr Asp Ala Ala Lys Arg Gly Pro Gly
        55                  60                  65

ggt gcc tgg gct gca gaa gtg atc agc gat gcc aga gag aat atc cag       475
Gly Ala Trp Ala Ala Glu Val Ile Ser Asp Ala Arg Glu Asn Ile Gln
    70                  75                  80

aga ttc ttt ggc cat ggt gcg gag gac tcg ctg gct gat cag gct gcc       523
Arg Phe Phe Gly His Gly Ala Glu Asp Ser Leu Ala Asp Gln Ala Ala
85                  90                  95                  100

aat gaa tgg ggc agg agt ggc aaa gac ccc aat cac ttc cga cct gct       571
Asn Glu Trp Gly Arg Ser Gly Lys Asp Pro Asn His Phe Arg Pro Ala
                105                 110                 115

ggc ctg cct gag aaa tac tga gcttcctctt cactctgctc tcaggagatc          622
Gly Leu Pro Glu Lys Tyr
            120

tggctgtgag gccctcaggg cagggataca aagcggggag agggtacaca atgggtatct     682

aataaatact taagaggtgg aatttgtgga aact                                 716


<210> SEQ ID NO 32
<211> LENGTH: 122
<212> TYPE: PRT
<213> ORGANISM: homo sapiens

<400> SEQUENCE: 32

Met Lys Leu Leu Thr Gly Leu Val Phe Cys Ser Leu Val Leu Gly Val
1               5                   10                  15
```

```
Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Ala Trp Ala Ala Glu Val Ile Ser Asp Ala Arg
65                  70                  75                  80

Glu Asn Ile Gln Arg Phe Phe Gly His Gly Ala Glu Asp Ser Leu Ala
                85                  90                  95

Asp Gln Ala Ala Asn Glu Trp Gly Arg Ser Gly Lys Asp Pro Asn His
            100                 105                 110

Phe Arg Pro Ala Gly Leu Pro Glu Lys Tyr
        115                 120


<210> SEQ ID NO 33
<211> LENGTH: 1887
<212> TYPE: DNA
<213> ORGANISM: homo sapiens
<220> FEATURE:
<221> NAME/KEY: CDS
<222> LOCATION: (250)..(540)

<400> SEQUENCE: 33

ctttttaagc tcccctgagc cggtgctgcg ctcctctaat tgggactccg agccggggct      60

atttctggcg ctggcgcggc tccaagaagg catccgcatt tgctaccagc ggcggccgcg     120

gcggagccag gccggtcctc agcgcccagc accgccgctc ccggcaaccc ggagcgcgca     180

ccgcaggccg gcggccgagc tcgcgcatcc cagccatcac tcttccacct gctccttaga     240

gaagggaag atg agt gag tcg agc tcg aag tcc agc cag ccc ttg gcc tcc     291
          Met Ser Glu Ser Ser Ser Lys Ser Ser Gln Pro Leu Ala Ser
          1               5                   10

aag cag gaa aag gac ggc act gag aag cgg ggc cgg ggc agg ccg cgc      339
Lys Gln Glu Lys Asp Gly Thr Glu Lys Arg Gly Arg Gly Arg Pro Arg
15                  20                  25                  30

aag cag cct ccg aag gag ccc agc gaa gtg cca aca cct aag aga cct      387
Lys Gln Pro Pro Lys Glu Pro Ser Glu Val Pro Thr Pro Lys Arg Pro
                35                  40                  45

cgg ggc cga cca aag gga agc aaa aac aag ggt gct gcc aag acc cgg      435
Arg Gly Arg Pro Lys Gly Ser Lys Asn Lys Gly Ala Ala Lys Thr Arg
            50                  55                  60

aaa acc acc aca act cca gga agg aaa cca agg ggc aga ccc aaa aaa      483
Lys Thr Thr Thr Thr Pro Gly Arg Lys Pro Arg Gly Arg Pro Lys Lys
        65                  70                  75

ctg gag aag gag gaa gag gag ggc atc tcg cag gag tcc tcg gag gag      531
Leu Glu Lys Glu Glu Glu Glu Gly Ile Ser Gln Glu Ser Ser Glu Glu
    80                  85                  90

gag cag tga cccatgcgtg ccgcctgctc ctcactggag gagcagcttc              580
Glu Gln
95

cttctgggac tggacagctt tgctccgctc ccaccgcccc cgccccttcc ccaggcccac     640

catcaccacc gcctctggcc gccacccccca tcttccacct gtgccctcac caccacacta    700

cacagcacac cagccgctgc agggctccca tgggctgagt ggggagcagt tttcccctgg     760

cctcagttcc cagctccccc cgcccaccca cgcatacaca catgccctcc tggacaaggc     820

taacatccca cttagccgca ccctgcacct gctgcgtccc cactcccttg gtggtgggga     880
```

```
cattgctctc tgggcttttg gtttgggggc gccctctctg ctccttcact gttccctctg    940

gcttcccata gtggggcctg ggagggttcc cctggcctta aaaggggccc aagccccatc   1000

tcatcctggc acgccctact ccactgccct ggcagcagca ggtgtggcca atggaggggg   1060

gtgctggccc ccaggattcc cccagccaaa ctgtctttgt caccacgtgg ggctcacttt   1120

tcatccttcc ccaacttccc tagtccccgt actaggttgg acagccccct tcggctacag   1180

gaaggcagga ggggtgagtc ccctactccc tcttcactgt ggccacagcc cccttgccct   1240

ccgcctggga tctgagtaca tattgtggtg atggagatgc agtcacttat tgtccaggtg   1300

aggcccaaga gccctgtggc cgccacctga ggtgggctgg ggctgctccc ctaaccctac   1360

tttgcttccg ccactcagcc atttccccct cctcagatgg ggcaccaata acaaggagct   1420

caccctgccc gctcccaacc cccctcctgc tcctccctgc cccccaaggt tctggttcca   1480

tttttcctct gttcacaaac tacctctgga cagttgtgtt gttttttgtt caatgttcca   1540

ttcttcgaca tccgtcattg ctgctgctac cagcgccaaa tgttcatcct cattgcctcc   1600

tgttctgccc acgatcccct cccccaagat actctttgtg ggaagagggg gctggggcat   1660

ggcaggctgg gtgaccgact accccagtcc cagggaaggt ggggccctgc ccctaggatg   1720

ctgcagcaga gtgagcaagg gggcccgaat cgaccataaa gggtgtaggg gccacctcct   1780

ccccctgttc tgttggggag gggtagccat gatttgtccc agcctggggc tccctctctg   1840

gtttcctatt tgcagttact tgaataaaaa aaatatcctt ttctgga                 1887


<210> SEQ ID NO 34
<211> LENGTH: 96
<212> TYPE: PRT
<213> ORGANISM: homo sapiens

<400> SEQUENCE: 34

Met Ser Glu Ser Ser Ser Lys Ser Ser Gln Pro Leu Ala Ser Lys Gln
1               5                   10                  15

Glu Lys Asp Gly Thr Glu Lys Arg Gly Arg Gly Arg Pro Arg Lys Gln
            20                  25                  30

Pro Pro Lys Glu Pro Ser Glu Val Pro Thr Pro Lys Arg Pro Arg Gly
        35                  40                  45

Arg Pro Lys Gly Ser Lys Asn Lys Gly Ala Ala Lys Thr Arg Lys Thr
    50                  55                  60

Thr Thr Thr Pro Gly Arg Lys Pro Arg Gly Arg Pro Lys Lys Leu Glu
65                  70                  75                  80

Lys Glu Glu Glu Glu Gly Ile Ser Gln Glu Ser Ser Glu Glu Glu Gln
                85                  90                  95


<210> SEQ ID NO 35
<211> LENGTH: 627
<212> TYPE: DNA
<213> ORGANISM: homo sapiens
<220> FEATURE:
<221> NAME/KEY: CDS
<222> LOCATION: (96)..(335)

<400> SEQUENCE: 35

agtctccggc gagttgttgc ctgggctgga cgtggttttg tctgctgcgc ccgctcttcg     60

cgctctcgtt tcattttctg cagcgcgcca cgagg atg gcc cac aag cag atc       113
                                       Met Ala His Lys Gln Ile
                                       1               5

tac tac tcg gac aag tac ttc gac gaa cac tac gag tac cgg cat gtt      161
Tyr Tyr Ser Asp Lys Tyr Phe Asp Glu His Tyr Glu Tyr Arg His Val
```

```
            10                  15                  20

atg tta ccc aga gaa ctt tcc aaa caa gta cct aaa act cat ctg atg      209
Met Leu Pro Arg Glu Leu Ser Lys Gln Val Pro Lys Thr His Leu Met
        25                  30                  35

tct gaa gag gag tgg agg aga ctt ggt gtc caa cag agt cta ggc tgg      257
Ser Glu Glu Glu Trp Arg Arg Leu Gly Val Gln Gln Ser Leu Gly Trp
    40                  45                  50

gtt cat tac atg att cat gag cca gaa cca cat att ctt ctc ttt aga      305
Val His Tyr Met Ile His Glu Pro Glu Pro His Ile Leu Leu Phe Arg
55                  60                  65                  70

cga cct ctt cca aaa gat caa caa aaa tga agtttatctg gggatcgtca        355
Arg Pro Leu Pro Lys Asp Gln Gln Lys
                75

aatcttttc aaatttaatg tatatgtgta tataaggtag tattcagtga atacttgaga    415

aatgtacaaa tctttcatcc atacctgtgc atgagctgta ttcttcacag caacagagct    475

cagttaaatg caactgcaag taggttactg taagatgttt aagataaaag ttcttccagt    535

cagtttttct cttaagtgcc tgtttgagtt tactgaaaca gtttactttt gttcaataaa    595

gtttgtatgt tgcatttaaa aaaaaaaaaa aa                                  627


<210> SEQ ID NO 36
<211> LENGTH: 79
<212> TYPE: PRT
<213> ORGANISM: homo sapiens

<400> SEQUENCE: 36

Met Ala His Lys Gln Ile Tyr Tyr Ser Asp Lys Tyr Phe Asp Glu His
1               5                   10                  15

Tyr Glu Tyr Arg His Val Met Leu Pro Arg Glu Leu Ser Lys Gln Val
            20                  25                  30

Pro Lys Thr His Leu Met Ser Glu Glu Glu Trp Arg Arg Leu Gly Val
        35                  40                  45

Gln Gln Ser Leu Gly Trp Val His Tyr Met Ile His Glu Pro Glu Pro
    50                  55                  60

His Ile Leu Leu Phe Arg Arg Pro Leu Pro Lys Asp Gln Gln Lys
65                  70                  75


<210> SEQ ID NO 37
<211> LENGTH: 3480
<212> TYPE: DNA
<213> ORGANISM: homo sapiens
<220> FEATURE:
<221> NAME/KEY: CDS
<222> LOCATION: (268)..(2925)

<400> SEQUENCE: 37

ggcggagatc gcgtctcttt cgctccgtgt ccgctgctgc tcctgtgagc gcccggcgag     60

tccgtcccgt ccaccgtccg cagctggtag ccagcctgcc cctcgcctcg actccctttc    120

accaacaccg acacccacat tgacacctcc agtccggcca gccgctccac tcgttgcctt    180

tgcatctcca cacatggcgt cctcgcgcag agcggcggct cctccggggg acccgcggtc    240

cccaccgtgc agcggggcat catcaag atg gtc ctc tca ggg tgc gcc atc att    294
                              Met Val Leu Ser Gly Cys Ala Ile Ile
                              1               5

gtc cga ggt cag cct cgt ggt ggg cct cct cct gag cgg cag atc aac      342
Val Arg Gly Gln Pro Arg Gly Gly Pro Pro Pro Glu Arg Gln Ile Asn
10                  15                  20                  25

ctc agc aac att cgt gct gga aat ctt gct cgc cgg gca gcc gcc aca      390
```

```
Leu Ser Asn Ile Arg Ala Gly Asn Leu Ala Arg Arg Ala Ala Ala Thr
                30                  35                  40

caa cct gat gca aag gat acc cct gat gag ccc tgg gca ttt cca gct      438
Gln Pro Asp Ala Lys Asp Thr Pro Asp Glu Pro Trp Ala Phe Pro Ala
            45                  50                  55

cga gag ttc ctt cga aag aag ctg att ggg aag gaa gtc tgt ttc acg      486
Arg Glu Phe Leu Arg Lys Lys Leu Ile Gly Lys Glu Val Cys Phe Thr
        60                  65                  70

ata gaa aac aag act ccc cag ggg cga gag tat ggc atg atc tac ctt      534
Ile Glu Asn Lys Thr Pro Gln Gly Arg Glu Tyr Gly Met Ile Tyr Leu
    75                  80                  85

gga aaa gat acc aat ggg gaa aac att gca gaa tca ctg gtt gca gag      582
Gly Lys Asp Thr Asn Gly Glu Asn Ile Ala Glu Ser Leu Val Ala Glu
90                  95                  100                 105

ggc tta gcc acc cgg aga gaa ggc atg aga gct aat aat cct gag cag      630
Gly Leu Ala Thr Arg Arg Glu Gly Met Arg Ala Asn Asn Pro Glu Gln
                110                 115                 120

aac cgg ctt tca gaa tgt gaa gaa caa gca aag gca gcc aag aaa ggg      678
Asn Arg Leu Ser Glu Cys Glu Glu Gln Ala Lys Ala Ala Lys Lys Gly
            125                 130                 135

atg tgg agt gag ggg aac ggt tca cat act atc cgg gat ctc aag tat      726
Met Trp Ser Glu Gly Asn Gly Ser His Thr Ile Arg Asp Leu Lys Tyr
        140                 145                 150

acc att gaa aac cca agg cac ttt gtg gac tca cac cac cag aag cct      774
Thr Ile Glu Asn Pro Arg His Phe Val Asp Ser His His Gln Lys Pro
    155                 160                 165

gtt aat gct atc atc gag cat gtg cgg gac ggc agt gtg gtc agg gcc      822
Val Asn Ala Ile Ile Glu His Val Arg Asp Gly Ser Val Val Arg Ala
170                 175                 180                 185

ctg ctc ctc cca gat tac tac ctg gtt aca gtc atg ctg tca ggc atc      870
Leu Leu Leu Pro Asp Tyr Tyr Leu Val Thr Val Met Leu Ser Gly Ile
                190                 195                 200

aag tgc cca act ttt cga cgg gaa gca gat ggc agt gaa act cca gag      918
Lys Cys Pro Thr Phe Arg Arg Glu Ala Asp Gly Ser Glu Thr Pro Glu
            205                 210                 215

cct ttt gct gca gaa gcc aaa ttt ttc act gag tcg cga ctg ctt cag      966
Pro Phe Ala Ala Glu Ala Lys Phe Phe Thr Glu Ser Arg Leu Leu Gln
        220                 225                 230

aga gat gtt cag atc att ctg gag agc tgc cac aac cag aac att gtg     1014
Arg Asp Val Gln Ile Ile Leu Glu Ser Cys His Asn Gln Asn Ile Val
    235                 240                 245

ggt acc atc ctt cat cca aat ggc aac atc aca gag ctc ctc ctg aag     1062
Gly Thr Ile Leu His Pro Asn Gly Asn Ile Thr Glu Leu Leu Leu Lys
250                 255                 260                 265

gaa ggt ttc gca cgc tgt gtg gac tgg tcg att gca gtt tac acc cgg     1110
Glu Gly Phe Ala Arg Cys Val Asp Trp Ser Ile Ala Val Tyr Thr Arg
                270                 275                 280

ggc gca gaa aag ctg agg gcg gca gag agg ttt gcc aaa gag cgc agg     1158
Gly Ala Glu Lys Leu Arg Ala Ala Glu Arg Phe Ala Lys Glu Arg Arg
            285                 290                 295

ctg aga ata tgg aga gac tat gtg gct ccc aca gct aat ttg gac caa     1206
Leu Arg Ile Trp Arg Asp Tyr Val Ala Pro Thr Ala Asn Leu Asp Gln
        300                 305                 310

aag gac aag cag ttt gtt gcc aag gtg atg cag gtt ctg aat gct gat     1254
Lys Asp Lys Gln Phe Val Ala Lys Val Met Gln Val Leu Asn Ala Asp
    315                 320                 325

gcc att gtt gtg aag ctg aac tca ggc gat tac aag acg att cac ctg     1302
Ala Ile Val Val Lys Leu Asn Ser Gly Asp Tyr Lys Thr Ile His Leu
330                 335                 340                 345
```

```
tcc agc atc cga cca ccg agg ctg gag ggg gag aac acc cag gat aag      1350
Ser Ser Ile Arg Pro Pro Arg Leu Glu Gly Glu Asn Thr Gln Asp Lys
                350                 355                 360

aac aag aaa ctg cgt ccc ctg tat gac att cct tac atg ttt gag gcc      1398
Asn Lys Lys Leu Arg Pro Leu Tyr Asp Ile Pro Tyr Met Phe Glu Ala
            365                 370                 375

cgg gaa ttt ctt cga aaa aag ctt att ggg aag aag gtc aat gtg acg      1446
Arg Glu Phe Leu Arg Lys Lys Leu Ile Gly Lys Lys Val Asn Val Thr
        380                 385                 390

gtg gac tac att aga cca gcc agc cca gcc aca gag aca gtg cct gcc      1494
Val Asp Tyr Ile Arg Pro Ala Ser Pro Ala Thr Glu Thr Val Pro Ala
    395                 400                 405

ttt tca gag cgt acc tgt gcc act gtc acc att gga gga ata aac att      1542
Phe Ser Glu Arg Thr Cys Ala Thr Val Thr Ile Gly Gly Ile Asn Ile
410                 415                 420                 425

gct gag gct ctt gtc agc aaa ggt cta gcc aca gtg atc aga tac cgg      1590
Ala Glu Ala Leu Val Ser Lys Gly Leu Ala Thr Val Ile Arg Tyr Arg
                430                 435                 440

cag gat gat gac cag aga tca tca cac tac gat gaa ctg ctt gct gca      1638
Gln Asp Asp Asp Gln Arg Ser Ser His Tyr Asp Glu Leu Leu Ala Ala
            445                 450                 455

gag gcc aga gct att aag aat ggc aaa gga ttg cat agc aag aag gaa      1686
Glu Ala Arg Ala Ile Lys Asn Gly Lys Gly Leu His Ser Lys Lys Glu
        460                 465                 470

gtg cct atc cac cgt gtt gca gat ata tct ggg gat acc caa aaa gca      1734
Val Pro Ile His Arg Val Ala Asp Ile Ser Gly Asp Thr Gln Lys Ala
    475                 480                 485

aag cag ttc ctg cct ttt ctt cag cgg gca ggt cgt tct gaa gct gtg      1782
Lys Gln Phe Leu Pro Phe Leu Gln Arg Ala Gly Arg Ser Glu Ala Val
490                 495                 500                 505

gtg gaa tac gtc ttc agt ggt tct cgt ctc aaa ctc tat ttg cca aag      1830
Val Glu Tyr Val Phe Ser Gly Ser Arg Leu Lys Leu Tyr Leu Pro Lys
                510                 515                 520

gaa act tgc ctt atc acc ttc ttg ctt gca ggc att gaa tgc ccc aga      1878
Glu Thr Cys Leu Ile Thr Phe Leu Leu Ala Gly Ile Glu Cys Pro Arg
            525                 530                 535

gga gcc cga aac ctc cca ggc ttg gtg cag gaa gga gag ccc ttc agc      1926
Gly Ala Arg Asn Leu Pro Gly Leu Val Gln Glu Gly Glu Pro Phe Ser
        540                 545                 550

gag gaa gct aca ctt ttc acc aag gaa ctg gtg ctg cag cga gag gtg      1974
Glu Glu Ala Thr Leu Phe Thr Lys Glu Leu Val Leu Gln Arg Glu Val
    555                 560                 565

gag gtg gag gtg gag agc atg gac aag gcc ggc aac ttt atc ggc tgg      2022
Glu Val Glu Val Glu Ser Met Asp Lys Ala Gly Asn Phe Ile Gly Trp
570                 575                 580                 585

ctg cac atc gac ggt gcc aac ctg tcc gtc ctg ctg gtg gag cac gcg      2070
Leu His Ile Asp Gly Ala Asn Leu Ser Val Leu Leu Val Glu His Ala
                590                 595                 600

ctc tcc aag gtc cac ttc acc gcc gaa cgc agc tcc tac tac aag tcc      2118
Leu Ser Lys Val His Phe Thr Ala Glu Arg Ser Ser Tyr Tyr Lys Ser
            605                 610                 615

ctg ctg tct gcc gag gag gcc gca aag cag aag aaa gag aag gtc tgg      2166
Leu Leu Ser Ala Glu Glu Ala Ala Lys Gln Lys Lys Glu Lys Val Trp
        620                 625                 630

gcc cac tat gag gag cag ccc gtg gag gag gtg atg cca gtg ctg gag      2214
Ala His Tyr Glu Glu Gln Pro Val Glu Glu Val Met Pro Val Leu Glu
    635                 640                 645

gag aag gag cga tct gct agc tac aag ccc gtg ttt gtg acc gag atc      2262
Glu Lys Glu Arg Ser Ala Ser Tyr Lys Pro Val Phe Val Thr Glu Ile
650                 655                 660                 665
```

```
act gat gac ctg cac ttc tac gtg cag gat gtg gag acc ggc acc cag     2310
Thr Asp Asp Leu His Phe Tyr Val Gln Asp Val Glu Thr Gly Thr Gln
                670                 675                 680

ttc cag aag ctg atg gag aac atg cgc aat gac att gcc agt cac ccc     2358
Phe Gln Lys Leu Met Glu Asn Met Arg Asn Asp Ile Ala Ser His Pro
            685                 690                 695

cct gta gag ggc tcc tat gcc ccc cgc agg gga gag ttc tgc att gcc     2406
Pro Val Glu Gly Ser Tyr Ala Pro Arg Arg Gly Glu Phe Cys Ile Ala
        700                 705                 710

aaa ttt gta gat gga gaa tgg tac cgt gcc cga gta gag aaa gtc gag     2454
Lys Phe Val Asp Gly Glu Trp Tyr Arg Ala Arg Val Glu Lys Val Glu
    715                 720                 725

tct cct gcc aaa ata cat gtc ttc tac att gac tac ggc aac aga gag     2502
Ser Pro Ala Lys Ile His Val Phe Tyr Ile Asp Tyr Gly Asn Arg Glu
730                 735                 740                 745

gtc ctg cca tcc acc cgc ctg ggt acc cta tca cct gcc ttc agc act     2550
Val Leu Pro Ser Thr Arg Leu Gly Thr Leu Ser Pro Ala Phe Ser Thr
                750                 755                 760

cgg gtg ctg cca gct caa gcc acg gag tat gcc ttc gcc ttc atc cag     2598
Arg Val Leu Pro Ala Gln Ala Thr Glu Tyr Ala Phe Ala Phe Ile Gln
            765                 770                 775

gtg ccc caa gat gat gat gcc cgc acg gac gcc gtg gac agc gta gtt     2646
Val Pro Gln Asp Asp Asp Ala Arg Thr Asp Ala Val Asp Ser Val Val
        780                 785                 790

cgg gat atc cag aac act cag tgc ctg ctc aac gtg gaa cac ctg agt     2694
Arg Asp Ile Gln Asn Thr Gln Cys Leu Leu Asn Val Glu His Leu Ser
    795                 800                 805

gcc ggc tgc ccc cat gtc acc ctg cag ttt gca gat tcc aag ggc gat     2742
Ala Gly Cys Pro His Val Thr Leu Gln Phe Ala Asp Ser Lys Gly Asp
810                 815                 820                 825

gtg ggg ctg ggc ttg gtg aag gaa ggg ctg gtc atg gtg gag gtg cgc     2790
Val Gly Leu Gly Leu Val Lys Glu Gly Leu Val Met Val Glu Val Arg
                830                 835                 840

aag gag aaa cag ttc cag aaa gtg atc aca gaa tac ctg aat gcc caa     2838
Lys Glu Lys Gln Phe Gln Lys Val Ile Thr Glu Tyr Leu Asn Ala Gln
            845                 850                 855

gag tca gcc aag agc gcc agg ctg aac ctg tgg cgc tat gga gac ttt     2886
Glu Ser Ala Lys Ser Ala Arg Leu Asn Leu Trp Arg Tyr Gly Asp Phe
        860                 865                 870

cga gct gat gat gca gac gaa ttt ggc tac agc cgc taa ggaggggatc      2935
Arg Ala Asp Asp Ala Asp Glu Phe Gly Tyr Ser Arg
    875                 880                 885

gggtttggcc cccagccccc gtcacgccag tccctcttcc tctgccggga gggtgttttc   2995

aactccaaac cccagagagg ggttgtacat tgggtccagc tttgcttcag tgtgtggaaa   3055

tgtctcgtgg ggtggcatcg gggctgcggg gtggggaccc caaggctttc tggggcagac   3115

ccttgtcctc tgggatgatg ggcactgcta tccacagtct ctgccagttg gttttatttg   3175

gaggtttgtg ggcttttttta aaaaaaaaaa agtcctcaaa tcaggaagaa acatcaaaga  3235

ctatgtccta gtggagggag taatcctaac acccaggctg gccgccagct ggcacctgcc   3295

tctatcccag actgccctcg tcccagctct ctgtccaact gttgattatg tgatttttct   3355

gatacgtcca ttctcaaatg ccagtgtgtt cacatcttcg ctctggccag cccattctgt   3415

atttaaagct ttttgaggcc caataaaata gtacgtgctg ctgcagccct tattgatcaa   3475

aaaaa                                                               3480
```

<210> SEQ ID NO 38

```
<211> LENGTH: 885
<212> TYPE: PRT
<213> ORGANISM: homo sapiens

<400> SEQUENCE: 38

Met Val Leu Ser Gly Cys Ala Ile Ile Val Arg Gly Gln Pro Arg Gly
1               5                   10                  15

Gly Pro Pro Pro Glu Arg Gln Ile Asn Leu Ser Asn Ile Arg Ala Gly
            20                  25                  30

Asn Leu Ala Arg Arg Ala Ala Ala Thr Gln Pro Asp Ala Lys Asp Thr
        35                  40                  45

Pro Asp Glu Pro Trp Ala Phe Pro Ala Arg Glu Phe Leu Arg Lys Lys
    50                  55                  60

Leu Ile Gly Lys Glu Val Cys Phe Thr Ile Glu Asn Lys Thr Pro Gln
65                  70                  75                  80

Gly Arg Glu Tyr Gly Met Ile Tyr Leu Gly Lys Asp Thr Asn Gly Glu
                85                  90                  95

Asn Ile Ala Glu Ser Leu Val Ala Glu Gly Leu Ala Thr Arg Arg Glu
            100                 105                 110

Gly Met Arg Ala Asn Asn Pro Glu Gln Asn Arg Leu Ser Glu Cys Glu
        115                 120                 125

Glu Gln Ala Lys Ala Ala Lys Lys Gly Met Trp Ser Glu Gly Asn Gly
    130                 135                 140

Ser His Thr Ile Arg Asp Leu Lys Tyr Thr Ile Glu Asn Pro Arg His
145                 150                 155                 160

Phe Val Asp Ser His His Gln Lys Pro Val Asn Ala Ile Ile Glu His
                165                 170                 175

Val Arg Asp Gly Ser Val Val Arg Ala Leu Leu Leu Pro Asp Tyr Tyr
            180                 185                 190

Leu Val Thr Val Met Leu Ser Gly Ile Lys Cys Pro Thr Phe Arg Arg
        195                 200                 205

Glu Ala Asp Gly Ser Glu Thr Pro Glu Pro Phe Ala Ala Glu Ala Lys
    210                 215                 220

Phe Phe Thr Glu Ser Arg Leu Leu Gln Arg Asp Val Gln Ile Ile Leu
225                 230                 235                 240

Glu Ser Cys His Asn Gln Asn Ile Val Gly Thr Ile Leu His Pro Asn
                245                 250                 255

Gly Asn Ile Thr Glu Leu Leu Leu Lys Glu Gly Phe Ala Arg Cys Val
            260                 265                 270

Asp Trp Ser Ile Ala Val Tyr Thr Arg Gly Ala Glu Lys Leu Arg Ala
        275                 280                 285

Ala Glu Arg Phe Ala Lys Glu Arg Arg Leu Arg Ile Trp Arg Asp Tyr
    290                 295                 300

Val Ala Pro Thr Ala Asn Leu Asp Gln Lys Asp Lys Gln Phe Val Ala
305                 310                 315                 320

Lys Val Met Gln Val Leu Asn Ala Asp Ala Ile Val Val Lys Leu Asn
                325                 330                 335

Ser Gly Asp Tyr Lys Thr Ile His Leu Ser Ser Ile Arg Pro Pro Arg
            340                 345                 350

Leu Glu Gly Glu Asn Thr Gln Asp Lys Asn Lys Lys Leu Arg Pro Leu
        355                 360                 365

Tyr Asp Ile Pro Tyr Met Phe Glu Ala Arg Glu Phe Leu Arg Lys Lys
    370                 375                 380

Leu Ile Gly Lys Lys Val Asn Val Thr Val Asp Tyr Ile Arg Pro Ala
```

```
385                 390                 395                 400

Ser Pro Ala Thr Glu Thr Val Pro Ala Phe Ser Glu Arg Thr Cys Ala
                405                 410                 415

Thr Val Thr Ile Gly Gly Ile Asn Ile Ala Glu Ala Leu Val Ser Lys
            420                 425                 430

Gly Leu Ala Thr Val Ile Arg Tyr Arg Gln Asp Asp Asp Gln Arg Ser
        435                 440                 445

Ser His Tyr Asp Glu Leu Leu Ala Ala Glu Ala Arg Ala Ile Lys Asn
    450                 455                 460

Gly Lys Gly Leu His Ser Lys Lys Glu Val Pro Ile His Arg Val Ala
465                 470                 475                 480

Asp Ile Ser Gly Asp Thr Gln Lys Ala Lys Gln Phe Leu Pro Phe Leu
                485                 490                 495

Gln Arg Ala Gly Arg Ser Glu Ala Val Val Glu Tyr Val Phe Ser Gly
            500                 505                 510

Ser Arg Leu Lys Leu Tyr Leu Pro Lys Glu Thr Cys Leu Ile Thr Phe
        515                 520                 525

Leu Leu Ala Gly Ile Glu Cys Pro Arg Gly Ala Arg Asn Leu Pro Gly
    530                 535                 540

Leu Val Gln Glu Gly Glu Pro Phe Ser Glu Glu Ala Thr Leu Phe Thr
545                 550                 555                 560

Lys Glu Leu Val Leu Gln Arg Glu Val Glu Val Glu Val Glu Ser Met
                565                 570                 575

Asp Lys Ala Gly Asn Phe Ile Gly Trp Leu His Ile Asp Gly Ala Asn
            580                 585                 590

Leu Ser Val Leu Leu Val Glu His Ala Leu Ser Lys Val His Phe Thr
        595                 600                 605

Ala Glu Arg Ser Ser Tyr Tyr Lys Ser Leu Leu Ser Ala Glu Glu Ala
    610                 615                 620

Ala Lys Gln Lys Lys Glu Lys Val Trp Ala His Tyr Glu Glu Gln Pro
625                 630                 635                 640

Val Glu Glu Val Met Pro Val Leu Glu Glu Lys Glu Arg Ser Ala Ser
                645                 650                 655

Tyr Lys Pro Val Phe Val Thr Glu Ile Thr Asp Asp Leu His Phe Tyr
            660                 665                 670

Val Gln Asp Val Glu Thr Gly Thr Gln Phe Gln Lys Leu Met Glu Asn
        675                 680                 685

Met Arg Asn Asp Ile Ala Ser His Pro Pro Val Glu Gly Ser Tyr Ala
    690                 695                 700

Pro Arg Arg Gly Glu Phe Cys Ile Ala Lys Phe Val Asp Gly Glu Trp
705                 710                 715                 720

Tyr Arg Ala Arg Val Glu Lys Val Glu Ser Pro Ala Lys Ile His Val
                725                 730                 735

Phe Tyr Ile Asp Tyr Gly Asn Arg Glu Val Leu Pro Ser Thr Arg Leu
            740                 745                 750

Gly Thr Leu Ser Pro Ala Phe Ser Thr Arg Val Leu Pro Ala Gln Ala
        755                 760                 765

Thr Glu Tyr Ala Phe Ala Phe Ile Gln Val Pro Gln Asp Asp Asp Ala
    770                 775                 780

Arg Thr Asp Ala Val Asp Ser Val Val Arg Asp Ile Gln Asn Thr Gln
785                 790                 795                 800

Cys Leu Leu Asn Val Glu His Leu Ser Ala Gly Cys Pro His Val Thr
                805                 810                 815
```

```
Leu Gln Phe Ala Asp Ser Lys Gly Asp Val Gly Leu Gly Leu Val Lys
            820                 825                 830

Glu Gly Leu Val Met Val Glu Val Arg Lys Glu Lys Gln Phe Gln Lys
        835                 840                 845

Val Ile Thr Glu Tyr Leu Asn Ala Gln Glu Ser Ala Lys Ser Ala Arg
    850                 855                 860

Leu Asn Leu Trp Arg Tyr Gly Asp Phe Arg Ala Asp Asp Ala Asp Glu
865                 870                 875                 880

Phe Gly Tyr Ser Arg
                885


<210> SEQ ID NO 39
<211> LENGTH: 2331
<212> TYPE: DNA
<213> ORGANISM: homo sapiens
<220> FEATURE:
<221> NAME/KEY: CDS
<222> LOCATION: (49)..(1743)

<400> SEQUENCE: 39

cgcctccagc ctctcacact ctcctaagcc ctctcatctc ctggaacc atg gcc agc      57
                                                     Met Ala Ser
                                                     1

aca tcc acc acc atc agg agc cac agc agc agc cgc cgg ggt ttc agt      105
Thr Ser Thr Thr Ile Arg Ser His Ser Ser Ser Arg Arg Gly Phe Ser
    5                   10                  15

gcc aac tca gcc agg ctc cct ggg gtc agc cgc tct ggc ttc agc agc      153
Ala Asn Ser Ala Arg Leu Pro Gly Val Ser Arg Ser Gly Phe Ser Ser
20                  25                  30                  35

atc tcc gtg tcc cgc tcc agg ggc agt ggt ggc ctg ggt ggc gca tgt      201
Ile Ser Val Ser Arg Ser Arg Gly Ser Gly Gly Leu Gly Gly Ala Cys
                40                  45                  50

gga gga gct ggc ttt ggc agc cgc agt ctg tat ggc ctg ggg ggc tcc      249
Gly Gly Ala Gly Phe Gly Ser Arg Ser Leu Tyr Gly Leu Gly Gly Ser
            55                  60                  65

aag agg atc tcc att gga ggg ggc agc tgt gcc atc agt ggc ggc tat      297
Lys Arg Ile Ser Ile Gly Gly Gly Ser Cys Ala Ile Ser Gly Gly Tyr
        70                  75                  80

ggc agc aga gcc gga ggc agc tat ggc ttt ggt ggc gcc ggg agt gga      345
Gly Ser Arg Ala Gly Gly Ser Tyr Gly Phe Gly Gly Ala Gly Ser Gly
    85                  90                  95

ttt ggt ttc ggt ggt gga gcc ggc att ggc ttt ggt ctg ggt ggt gga      393
Phe Gly Phe Gly Gly Gly Ala Gly Ile Gly Phe Gly Leu Gly Gly Gly
100                 105                 110                 115

gcc ggc ctt gct ggt ggc ttt ggg ggc cct ggc ttc cct gtg tgc ccc      441
Ala Gly Leu Ala Gly Gly Phe Gly Gly Pro Gly Phe Pro Val Cys Pro
                120                 125                 130

cct gga ggc atc caa gag gtc act gtc aac cag agt ctc ctg act ccc      489
Pro Gly Gly Ile Gln Glu Val Thr Val Asn Gln Ser Leu Leu Thr Pro
            135                 140                 145

ctc aac ctg caa att gac ccc gcc atc cag cgg gtg cgg gcc gag gag      537
Leu Asn Leu Gln Ile Asp Pro Ala Ile Gln Arg Val Arg Ala Glu Glu
        150                 155                 160

cgt gag cag atc aag acc ctc aac aac aag ttt gcc tcc ttc atc gac      585
Arg Glu Gln Ile Lys Thr Leu Asn Asn Lys Phe Ala Ser Phe Ile Asp
    165                 170                 175

aag gtg cgg ttc cta gag cag cag aac aag gtt ctg gac acc aag tgg      633
Lys Val Arg Phe Leu Glu Gln Gln Asn Lys Val Leu Asp Thr Lys Trp
180                 185                 190                 195
```

-continued

```
acc ctg ctg cag gag cag ggc acc aag act gtg agg cag aac ctg gag      681
Thr Leu Leu Gln Glu Gln Gly Thr Lys Thr Val Arg Gln Asn Leu Glu
                200                 205                 210

ccg ttg ttc gag cag tac atc aac aac ctc agg agg cag ctg gac aac      729
Pro Leu Phe Glu Gln Tyr Ile Asn Asn Leu Arg Arg Gln Leu Asp Asn
            215                 220                 225

atc gtg ggg gaa cgg ggt cgt ctg gac tcg gag ctg aga aac atg cag      777
Ile Val Gly Glu Arg Gly Arg Leu Asp Ser Glu Leu Arg Asn Met Gln
        230                 235                 240

gac ctg gtg gag gac ctc aag aac aaa tat gag gat gaa atc aac aag      825
Asp Leu Val Glu Asp Leu Lys Asn Lys Tyr Glu Asp Glu Ile Asn Lys
    245                 250                 255

cgc aca gca gca gag aat gaa ttt gtg act ctg aag aag gat gtg gat      873
Arg Thr Ala Ala Glu Asn Glu Phe Val Thr Leu Lys Lys Asp Val Asp
260                 265                 270                 275

gct gcc tac atg aac aag gtt gaa ctg caa gcc aag gca gac act ctt      921
Ala Ala Tyr Met Asn Lys Val Glu Leu Gln Ala Lys Ala Asp Thr Leu
                280                 285                 290

aca gat gag atc aac ttc ctg aga gcc ttg tat gat gca gag ctg tcc      969
Thr Asp Glu Ile Asn Phe Leu Arg Ala Leu Tyr Asp Ala Glu Leu Ser
            295                 300                 305

cag atg cag acc cac atc tca gac aca tcc gtg gtg cta tcc atg gac     1017
Gln Met Gln Thr His Ile Ser Asp Thr Ser Val Val Leu Ser Met Asp
        310                 315                 320

aac aac cgc aac ctg gac ctg gac agc atc atc gct gag gtc aag gcc     1065
Asn Asn Arg Asn Leu Asp Leu Asp Ser Ile Ile Ala Glu Val Lys Ala
    325                 330                 335

caa tat gag gag att gct cag agg agc agg gct gag gct gag tcc tgg     1113
Gln Tyr Glu Glu Ile Ala Gln Arg Ser Arg Ala Glu Ala Glu Ser Trp
340                 345                 350                 355

tac cag aca aag tac gag gag ctg cag atc aca gca ggc aga cat ggg     1161
Tyr Gln Thr Lys Tyr Glu Glu Leu Gln Ile Thr Ala Gly Arg His Gly
                360                 365                 370

gac gac ctg cgc aac acc aag cag gag att gct gag atc aac cgc atg     1209
Asp Asp Leu Arg Asn Thr Lys Gln Glu Ile Ala Glu Ile Asn Arg Met
            375                 380                 385

atc cag agg ctg aga tct gag atc gac cac gtc aag aag cag tgt gcc     1257
Ile Gln Arg Leu Arg Ser Glu Ile Asp His Val Lys Lys Gln Cys Ala
        390                 395                 400

aac cta cag gcc gcc att gct gat gct gag cag cgt ggg gag atg gcc     1305
Asn Leu Gln Ala Ala Ile Ala Asp Ala Glu Gln Arg Gly Glu Met Ala
    405                 410                 415

ctc aag gat gct aag aac aag ctg gaa ggg ctg gag gat gcc ctg cag     1353
Leu Lys Asp Ala Lys Asn Lys Leu Glu Gly Leu Glu Asp Ala Leu Gln
420                 425                 430                 435

aag gcc aag cag gac ctg gcc cgg ctg ctg aag gag tac cag gag ctg     1401
Lys Ala Lys Gln Asp Leu Ala Arg Leu Leu Lys Glu Tyr Gln Glu Leu
                440                 445                 450

atg aac gtc aag ctg gcc ctg gat gtg gag atc gcc acc tac cgc aag     1449
Met Asn Val Lys Leu Ala Leu Asp Val Glu Ile Ala Thr Tyr Arg Lys
            455                 460                 465

ctg ctg gag ggc gag gag tgc agg ctg aat ggc gaa ggc gtt gga caa     1497
Leu Leu Glu Gly Glu Glu Cys Arg Leu Asn Gly Glu Gly Val Gly Gln
        470                 475                 480

gtc aac atc tct gta gtg cag tcc acc gtc tcc agt ggc tat ggc ggt     1545
Val Asn Ile Ser Val Val Gln Ser Thr Val Ser Ser Gly Tyr Gly Gly
    485                 490                 495

gcc agc ggt gtc ggc agt ggc tta ggc ctg ggt gga gga agc agc tac     1593
Ala Ser Gly Val Gly Ser Gly Leu Gly Leu Gly Gly Gly Ser Ser Tyr
500                 505                 510                 515
```

```
tcc tat ggc agt ggt ctt ggc gtt gga ggc ggc ttt agt tcc agc agc     1641
Ser Tyr Gly Ser Gly Leu Gly Val Gly Gly Gly Phe Ser Ser Ser Ser
                520                 525                 530

ggc aga gcc act ggg ggt ggc ctc agc tct gtt gga ggc ggc agt tcc     1689
Gly Arg Ala Thr Gly Gly Gly Leu Ser Ser Val Gly Gly Gly Ser Ser
            535                 540                 545

acc atc aag tac acc acc acc tcc tcc tcc agc agg aag agc tac aag     1737
Thr Ile Lys Tyr Thr Thr Thr Ser Ser Ser Ser Arg Lys Ser Tyr Lys
        550                 555                 560

cac tga agtgctgccg ccagctctca gtcccacagc tctcaggccc ctctctggca      1793
His

gcagagccct ctcctcaggt tgcttgtcct cccctggcct ccagtctccc ctgccctccc   1853

gggtagagct gggatgccct cacttttctt ctcatcaata cctgttccac tgagctcctg   1913

ttgcttacca tcaagtcaac agttatcagc actcagacat gcgaatgtcc tttttagttc   1973

ccgtattatt acaggtatct gagtctgcca taattctgag aagaaaatga cctatatccc   2033

cataagaact gaaactcagt ctaggtccag ctgcagatga ggagtcctct ctttaattgc   2093

taaccatcct gcccattata gctacactca ggagttctca tctgacaagt cagttgtcct   2153

gatcttctct tgcagtgtcc ctgaatggca agtgatgtac cttctgatgc agtctgcatt   2213

cctgcactgc tttctctgct ctctttgcct tcttttgttc tgttgaataa agcatattga   2273

gaatgtgaaa aaaaaaaaaa aaaaaaaaaa aaaaaaaaaa aaaaaaaaaa aaaaaaa      2331


<210> SEQ ID NO 40
<211> LENGTH: 564
<212> TYPE: PRT
<213> ORGANISM: homo sapiens

<400> SEQUENCE: 40

Met Ala Ser Thr Ser Thr Thr Ile Arg Ser His Ser Ser Ser Arg Arg
1               5                   10                  15

Gly Phe Ser Ala Asn Ser Ala Arg Leu Pro Gly Val Ser Arg Ser Gly
            20                  25                  30

Phe Ser Ser Ile Ser Val Ser Arg Ser Arg Gly Ser Gly Gly Leu Gly
        35                  40                  45

Gly Ala Cys Gly Gly Ala Gly Phe Gly Ser Arg Ser Leu Tyr Gly Leu
    50                  55                  60

Gly Gly Ser Lys Arg Ile Ser Ile Gly Gly Gly Ser Cys Ala Ile Ser
65                  70                  75                  80

Gly Gly Tyr Gly Ser Arg Ala Gly Gly Ser Tyr Gly Phe Gly Gly Ala
                85                  90                  95

Gly Ser Gly Phe Gly Phe Gly Gly Gly Ala Gly Ile Gly Phe Gly Leu
            100                 105                 110

Gly Gly Gly Ala Gly Leu Ala Gly Gly Phe Gly Gly Pro Gly Phe Pro
        115                 120                 125

Val Cys Pro Pro Gly Gly Ile Gln Glu Val Thr Val Asn Gln Ser Leu
    130                 135                 140

Leu Thr Pro Leu Asn Leu Gln Ile Asp Pro Ala Ile Gln Arg Val Arg
145                 150                 155                 160

Ala Glu Glu Arg Glu Gln Ile Lys Thr Leu Asn Asn Lys Phe Ala Ser
                165                 170                 175

Phe Ile Asp Lys Val Arg Phe Leu Glu Gln Gln Asn Lys Val Leu Asp
            180                 185                 190

Thr Lys Trp Thr Leu Leu Gln Glu Gln Gly Thr Lys Thr Val Arg Gln
```

```
        195                 200                 205

Asn Leu Glu Pro Leu Phe Glu Gln Tyr Ile Asn Asn Leu Arg Arg Gln
    210                 215                 220

Leu Asp Asn Ile Val Gly Glu Arg Gly Arg Leu Asp Ser Glu Leu Arg
225                 230                 235                 240

Asn Met Gln Asp Leu Val Glu Asp Leu Lys Asn Lys Tyr Glu Asp Glu
                245                 250                 255

Ile Asn Lys Arg Thr Ala Ala Glu Asn Glu Phe Val Thr Leu Lys Lys
            260                 265                 270

Asp Val Asp Ala Ala Tyr Met Asn Lys Val Glu Leu Gln Ala Lys Ala
        275                 280                 285

Asp Thr Leu Thr Asp Glu Ile Asn Phe Leu Arg Ala Leu Tyr Asp Ala
    290                 295                 300

Glu Leu Ser Gln Met Gln Thr His Ile Ser Asp Thr Ser Val Val Leu
305                 310                 315                 320

Ser Met Asp Asn Asn Arg Asn Leu Asp Leu Asp Ser Ile Ile Ala Glu
                325                 330                 335

Val Lys Ala Gln Tyr Glu Glu Ile Ala Gln Arg Ser Arg Ala Glu Ala
            340                 345                 350

Glu Ser Trp Tyr Gln Thr Lys Tyr Glu Glu Leu Gln Ile Thr Ala Gly
        355                 360                 365

Arg His Gly Asp Asp Leu Arg Asn Thr Lys Gln Glu Ile Ala Glu Ile
    370                 375                 380

Asn Arg Met Ile Gln Arg Leu Arg Ser Glu Ile Asp His Val Lys Lys
385                 390                 395                 400

Gln Cys Ala Asn Leu Gln Ala Ala Ile Ala Asp Ala Glu Gln Arg Gly
                405                 410                 415

Glu Met Ala Leu Lys Asp Ala Lys Asn Lys Leu Glu Gly Leu Glu Asp
            420                 425                 430

Ala Leu Gln Lys Ala Lys Gln Asp Leu Ala Arg Leu Leu Lys Glu Tyr
        435                 440                 445

Gln Glu Leu Met Asn Val Lys Leu Ala Leu Asp Val Glu Ile Ala Thr
    450                 455                 460

Tyr Arg Lys Leu Leu Glu Gly Glu Glu Cys Arg Leu Asn Gly Glu Gly
465                 470                 475                 480

Val Gly Gln Val Asn Ile Ser Val Val Gln Ser Thr Val Ser Ser Gly
                485                 490                 495

Tyr Gly Gly Ala Ser Gly Val Gly Ser Gly Leu Gly Leu Gly Gly Gly
            500                 505                 510

Ser Ser Tyr Ser Tyr Gly Ser Gly Leu Gly Val Gly Gly Gly Phe Ser
        515                 520                 525

Ser Ser Ser Gly Arg Ala Thr Gly Gly Gly Leu Ser Ser Val Gly Gly
    530                 535                 540

Gly Ser Ser Thr Ile Lys Tyr Thr Thr Thr Ser Ser Ser Ser Arg Lys
545                 550                 555                 560

Ser Tyr Lys His
```

<210> SEQ ID NO 41
<211> LENGTH: 818
<212> TYPE: DNA
<213> ORGANISM: homo sapiens
<220> FEATURE:
<221> NAME/KEY: CDS
<222> LOCATION: (247)..(564)

```
<400> SEQUENCE: 41

caaagggcgg cgcagcggct gccgagctcg gccctggagg cggcgagaac atggtgcgca      60

ggttcttggt gaccctccgg attcggcgcg cgtgcggccc gccgcgagtg agggttttcg     120

tggttcacat ctcgtggttc acgggggagt gggcagcgcc aggggcgccc gccgctgtgg     180

ccctcgtgct gatgctactg aggagccagc gtctagggca gcagccgctt cctagaagac     240

caggtc atg atg atg ggc agc gcc cga gtg gcg gag ctg ctg ctg ctc        288
       Met Met Met Gly Ser Ala Arg Val Ala Glu Leu Leu Leu Leu
       1               5                   10

cac ggc gcg gag ccc aac tgc gcc gac ccc gcc act ctc acc cga ccc       336
His Gly Ala Glu Pro Asn Cys Ala Asp Pro Ala Thr Leu Thr Arg Pro
15                  20                  25                  30

gtg cac gac gct gcc cgg gag ggc ttc ctg gac acg ctg gtg gtg ctg       384
Val His Asp Ala Ala Arg Glu Gly Phe Leu Asp Thr Leu Val Val Leu
                35                  40                  45

cac cgg gcc ggg gcg cgg ctg gac gtg cgc gat gcc tgg ggc cgt ctg       432
His Arg Ala Gly Ala Arg Leu Asp Val Arg Asp Ala Trp Gly Arg Leu
            50                  55                  60

ccc gtg gac ctg gct gag gag ctg ggc cat cgc gat gtc gca cgg tac       480
Pro Val Asp Leu Ala Glu Glu Leu Gly His Arg Asp Val Ala Arg Tyr
        65                  70                  75

ctg cgc gcg gct gcg ggg ggc acc aga ggc agt aac cat gcc cgc ata       528
Leu Arg Ala Ala Ala Gly Gly Thr Arg Gly Ser Asn His Ala Arg Ile
    80                  85                  90

gat gcc gcg gaa ggt ccc tca gac atc ccc gat tga aagaaccaga            574
Asp Ala Ala Glu Gly Pro Ser Asp Ile Pro Asp
95                  100                 105

gaggctctga gaaacctccg gaaacttaga tcatcagtca ccgaaggtcc tacagggcca     634

caactgcccc cgccacaacc caccccgctt tcgtagtttt catttagaaa atagagcttt     694

taaaaatgtc ctgcctttta acgtagatat atgccttccc ccactaccgt aaatgtccat     754

ttatatcatt ttttatatat tcttataaaa atgtaaaaaa gaaaaaaaaa aaaaaaaaaa     814

aaaa                                                                  818


<210> SEQ ID NO 42
<211> LENGTH: 105
<212> TYPE: PRT
<213> ORGANISM: homo sapiens

<400> SEQUENCE: 42

Met Met Met Gly Ser Ala Arg Val Ala Glu Leu Leu Leu Leu His Gly
1               5                   10                  15

Ala Glu Pro Asn Cys Ala Asp Pro Ala Thr Leu Thr Arg Pro Val His
            20                  25                  30

Asp Ala Ala Arg Glu Gly Phe Leu Asp Thr Leu Val Val Leu His Arg
        35                  40                  45

Ala Gly Ala Arg Leu Asp Val Arg Asp Ala Trp Gly Arg Leu Pro Val
    50                  55                  60

Asp Leu Ala Glu Glu Leu Gly His Arg Asp Val Ala Arg Tyr Leu Arg
65                  70                  75                  80

Ala Ala Ala Gly Gly Thr Arg Gly Ser Asn His Ala Arg Ile Asp Ala
                85                  90                  95

Ala Glu Gly Pro Ser Asp Ile Pro Asp
            100                 105


<210> SEQ ID NO 43
```

```
<211> LENGTH: 1154
<212> TYPE: DNA
<213> ORGANISM: homo sapiens
<220> FEATURE:
<221> NAME/KEY: CDS
<222> LOCATION: (38)..(559)

<400> SEQUENCE: 43

cgctcaggga aggcgggtgc gcgcctgcgg ggcggag atg ggc agg ggg cgg tgc      55
                                        Met Gly Arg Gly Arg Cys
                                        1               5

gtg ggt ccc agt ctg cag tta agg ggg cag gag tgg cgc tgc tca cct      103
Val Gly Pro Ser Leu Gln Leu Arg Gly Gln Glu Trp Arg Cys Ser Pro
            10                  15                  20

ctg gtg cca aag ggc ggc gca gcg gct gcc gag ctc ggc cct gga ggc      151
Leu Val Pro Lys Gly Gly Ala Ala Ala Ala Glu Leu Gly Pro Gly Gly
        25                  30                  35

ggc gag aac atg gtg cgc agg ttc ttg gtg acc ctc cgg att cgg cgc      199
Gly Glu Asn Met Val Arg Arg Phe Leu Val Thr Leu Arg Ile Arg Arg
    40                  45                  50

gcg tgc ggc ccg ccg cga gtg agg gtt ttc gtg gtt cac atc ccg cgg      247
Ala Cys Gly Pro Pro Arg Val Arg Val Phe Val Val His Ile Pro Arg
55                  60                  65                  70

ctc acg ggg gag tgg gca gcg cca ggg gcg ccc gcc gct gtg gcc ctc      295
Leu Thr Gly Glu Trp Ala Ala Pro Gly Ala Pro Ala Ala Val Ala Leu
                75                  80                  85

gtg ctg atg cta ctg agg agc cag cgt cta ggg cag cag ccg ctt cct      343
Val Leu Met Leu Leu Arg Ser Gln Arg Leu Gly Gln Gln Pro Leu Pro
            90                  95                  100

aga aga cca ggt cat gat gat ggg cag cgc ccg agt ggc gga gct gct      391
Arg Arg Pro Gly His Asp Asp Gly Gln Arg Pro Ser Gly Gly Ala Ala
        105                 110                 115

gct gct cca cgg cgc gga gcc caa ctg cgc cga ccc cgc cac tct cac      439
Ala Ala Pro Arg Arg Gly Ala Gln Leu Arg Arg Pro Arg His Ser His
    120                 125                 130

ccg acc cgt gca cga cgc tgc ccg gga ggg ctt cct gga cac gct ggt      487
Pro Thr Arg Ala Arg Arg Cys Pro Gly Gly Leu Pro Gly His Ala Gly
135                 140                 145                 150

ggt gct gca ccg ggc cgg ggc gcg gct gga cgt gcg cga tgc ctg ggg      535
Gly Ala Ala Pro Gly Arg Gly Ala Ala Gly Arg Ala Arg Cys Leu Gly
                155                 160                 165

ccg tct gcc cgt gga cct ggc tga ggagctgggc catcgcgatg tcgcacggta     589
Pro Ser Ala Arg Gly Pro Gly
            170

cctgcgcgcg gctgcggggg gcaccagagg cagtaaccat gcccgcatag atgccgcgga    649

aggtccctca gacatccccg attgaaagaa ccagagaggc tctgagaaac ctcgggaaac    709

ttagatcatc agtcaccgaa ggtcctacag ggccacaact gccccccgcca caacccaccc   769

cgctttcgta gttttcattt agaaaataga gcttttaaaa atgtcctgcc ttttaacgta    829

gatatatgcc ttcccccact accgtaaatg tccatttata tcattttttta tatattctta   889

taaaaatgta aaaaagaaaa acaccgcttc tgccttttca ctgtgttgga gttttctgga    949

gtgagcactc acgccctaag cgcacattca tgtgggcatt tcttgcgagc ctcgcagcct   1009

ccggaagctg tcgacttcat gacaagcatt ttgtgaacta gggaagctca ggggggttac   1069

tggcttctct tgagtcacac tgctagcaaa tggcagaacc aaagctcaaa taaaaataaa   1129

ataattttca ttcattcact caaaa                                          1154

<210> SEQ ID NO 44
```

<211> LENGTH: 173
<212> TYPE: PRT
<213> ORGANISM: homo sapiens

<400> SEQUENCE: 44

```
Met Gly Arg Gly Arg Cys Val Gly Pro Ser Leu Gln Leu Arg Gly Gln
1               5                   10                  15

Glu Trp Arg Cys Ser Pro Leu Val Pro Lys Gly Gly Ala Ala Ala Ala
            20                  25                  30

Glu Leu Gly Pro Gly Gly Gly Glu Asn Met Val Arg Arg Phe Leu Val
        35                  40                  45

Thr Leu Arg Ile Arg Arg Ala Cys Gly Pro Pro Arg Val Arg Val Phe
    50                  55                  60

Val Val His Ile Pro Arg Leu Thr Gly Glu Trp Ala Ala Pro Gly Ala
65                  70                  75                  80

Pro Ala Ala Val Ala Leu Val Leu Met Leu Leu Arg Ser Gln Arg Leu
                85                  90                  95

Gly Gln Gln Pro Leu Pro Arg Arg Pro Gly His Asp Asp Gly Gln Arg
            100                 105                 110

Pro Ser Gly Gly Ala Ala Ala Ala Pro Arg Arg Gly Ala Gln Leu Arg
        115                 120                 125

Arg Pro Arg His Ser His Pro Thr Arg Ala Arg Arg Cys Pro Gly Gly
    130                 135                 140

Leu Pro Gly His Ala Gly Gly Ala Ala Pro Gly Arg Gly Ala Ala Gly
145                 150                 155                 160

Arg Ala Arg Cys Leu Gly Pro Ser Ala Arg Gly Pro Gly
                165                 170
```

<210> SEQ ID NO 45
<211> LENGTH: 26
<212> TYPE: DNA
<213> ORGANISM: Artificial
<220> FEATURE:
<223> OTHER INFORMATION: synthetic IL8 forward primer

<400> SEQUENCE: 45
agatattgca cgggagaata tacaaa 26

<210> SEQ ID NO 46
<211> LENGTH: 27
<212> TYPE: DNA
<213> ORGANISM: Artificial
<220> FEATURE:
<223> OTHER INFORMATION: synthetic IL8 reverse primer

<400> SEQUENCE: 46
tcaattcctg aaattaaagt tcggata 27

<210> SEQ ID NO 47
<211> LENGTH: 23
<212> TYPE: DNA
<213> ORGANISM: Artificial
<220> FEATURE:
<223> OTHER INFORMATION: synthetic PTGS2 forward primer

<400> SEQUENCE: 47
tctgcagagt tggaagcact cta 23

<210> SEQ ID NO 48
<211> LENGTH: 21
<212> TYPE: DNA

```
<213> ORGANISM: Artificial
<220> FEATURE:
<223> OTHER INFORMATION: synthetic PTGS2 reverse primer

<400> SEQUENCE: 48

gccgaggctt ttctaccaga a                                              21


<210> SEQ ID NO 49
<211> LENGTH: 20
<212> TYPE: DNA
<213> ORGANISM: Artificial
<220> FEATURE:
<223> OTHER INFORMATION: synthetic ILR8RB forward primer

<400> SEQUENCE: 49

catggcttga tcagcaagga                                                20


<210> SEQ ID NO 50
<211> LENGTH: 21
<212> TYPE: DNA
<213> ORGANISM: Artificial
<220> FEATURE:
<223> OTHER INFORMATION: synthetic ILR8RB reverse primer

<400> SEQUENCE: 50

tggaagtgtg ccctgaagaa g                                              21


<210> SEQ ID NO 51
<211> LENGTH: 23
<212> TYPE: DNA
<213> ORGANISM: Artificial
<220> FEATURE:
<223> OTHER INFORMATION: synthetic LCN2 forward primer

<400> SEQUENCE: 51

caaggagctg acttcggaac taa                                            23


<210> SEQ ID NO 52
<211> LENGTH: 22
<212> TYPE: DNA
<213> ORGANISM: Artificial
<220> FEATURE:
<223> OTHER INFORMATION: synthetic LCN2 reverse primer

<400> SEQUENCE: 52

agggaagacg atgtggtttt ca                                             22


<210> SEQ ID NO 53
<211> LENGTH: 22
<212> TYPE: DNA
<213> ORGANISM: Artificial
<220> FEATURE:
<223> OTHER INFORMATION: synthetic SAA1 forward primer

<400> SEQUENCE: 53

gggacatgtg gagagcctac tc                                             22


<210> SEQ ID NO 54
<211> LENGTH: 21
<212> TYPE: DNA
<213> ORGANISM: Artificial
<220> FEATURE:
<223> OTHER INFORMATION: synthetic SAA1 reverse primer

<400> SEQUENCE: 54

catcatagtt cccccgagca t                                              21
```

<210> SEQ ID NO 55
<211> LENGTH: 21
<212> TYPE: DNA
<213> ORGANISM: Artificial
<220> FEATURE:
<223> OTHER INFORMATION: synthetic CSF1 (MCSF1) forward primer

<400> SEQUENCE: 55
aagcagcacc agcaagtgaa g 21

<210> SEQ ID NO 56
<211> LENGTH: 21
<212> TYPE: DNA
<213> ORGANISM: Artificial
<220> FEATURE:
<223> OTHER INFORMATION: synthetic CSF1 (MCSF1) reverse primer

<400> SEQUENCE: 56
tcatggcctg tgtcagtcaa a 21

<210> SEQ ID NO 57
<211> LENGTH: 22
<212> TYPE: DNA
<213> ORGANISM: Artificial
<220> FEATURE:
<223> OTHER INFORMATION: synthetic MGSA forward primer

<400> SEQUENCE: 57
acatgccagc cactgtgata ga 22

<210> SEQ ID NO 58
<211> LENGTH: 21
<212> TYPE: DNA
<213> ORGANISM: Artificial
<220> FEATURE:
<223> OTHER INFORMATION: synthetic MGSA reverse primer

<400> SEQUENCE: 58
ccctgccttc acaatgatct c 21

<210> SEQ ID NO 59
<211> LENGTH: 23
<212> TYPE: DNA
<213> ORGANISM: Artificial
<220> FEATURE:
<223> OTHER INFORMATION: synthetic CXCL3 forward primer

<400> SEQUENCE: 59
ggaattcacc tcaagaacat cca 23

<210> SEQ ID NO 60
<211> LENGTH: 23
<212> TYPE: DNA
<213> ORGANISM: Artificial
<220> FEATURE:
<223> OTHER INFORMATION: synthetic CXCL3 reverse primer

<400> SEQUENCE: 60
agtgtggcta tgacttcggt ttg 23

<210> SEQ ID NO 61
<211> LENGTH: 22
<212> TYPE: DNA
<213> ORGANISM: Artificial
<220> FEATURE:

<223> OTHER INFORMATION: synthetic SPP1 (OPN) forward primer

<400> SEQUENCE: 61
cagccacaag cagtccagat ta 22

<210> SEQ ID NO 62
<211> LENGTH: 24
<212> TYPE: DNA
<213> ORGANISM: Artificial
<220> FEATURE:
<223> OTHER INFORMATION: synthetic SPP1 (OPN) reverse primer

<400> SEQUENCE: 62
cctgactatc aatcacatcg gaat 24

<210> SEQ ID NO 63
<211> LENGTH: 21
<212> TYPE: DNA
<213> ORGANISM: Artificial
<220> FEATURE:
<223> OTHER INFORMATION: synthetic CCND1 forward primer

<400> SEQUENCE: 63
ccaggtgctc cacatgacag t 21

<210> SEQ ID NO 64
<211> LENGTH: 24
<212> TYPE: DNA
<213> ORGANISM: Artificial
<220> FEATURE:
<223> OTHER INFORMATION: synthetic CCND1 reverse primer

<400> SEQUENCE: 64
aaacaaccaa caacaaggag aatg 24

<210> SEQ ID NO 65
<211> LENGTH: 21
<212> TYPE: DNA
<213> ORGANISM: Artificial
<220> FEATURE:
<223> OTHER INFORMATION: synthetic c-Myc forward primer

<400> SEQUENCE: 65
cgtctccaca catcagcaca a 21

<210> SEQ ID NO 66
<211> LENGTH: 22
<212> TYPE: DNA
<213> ORGANISM: Artificial
<220> FEATURE:
<223> OTHER INFORMATION: synthetic c-Myc reverse primer

<400> SEQUENCE: 66
tcttggcagc aggatagtcc tt 22

<210> SEQ ID NO 67
<211> LENGTH: 22
<212> TYPE: DNA
<213> ORGANISM: Artificial
<220> FEATURE:
<223> OTHER INFORMATION: synthetic HUMCDK1 forward primer

<400> SEQUENCE: 67
gcagaccagc atgacagatt tc 22

<210> SEQ ID NO 68
<211> LENGTH: 20
<212> TYPE: DNA
<213> ORGANISM: Artificial
<220> FEATURE:
<223> OTHER INFORMATION: synthetic HUMCDK1 reverse primer

<400> SEQUENCE: 68
gcggattagg gcttcctctt 20

<210> SEQ ID NO 69
<211> LENGTH: 21
<212> TYPE: DNA
<213> ORGANISM: Artificial
<220> FEATURE:
<223> OTHER INFORMATION: synthetic CDKN2A (p16) forward primer

<400> SEQUENCE: 69
ggcaccagag gcagtaacca t 21

<210> SEQ ID NO 70
<211> LENGTH: 23
<212> TYPE: DNA
<213> ORGANISM: Artificial
<220> FEATURE:
<223> OTHER INFORMATION: synthetic CDKN2A (p16) reverse primer

<400> SEQUENCE: 70
agcctctctg gttctttcaa tcg 23

<210> SEQ ID NO 71
<211> LENGTH: 19
<212> TYPE: DNA
<213> ORGANISM: Artificial
<220> FEATURE:
<223> OTHER INFORMATION: synthetic CDKN2A (p14ARF) forward primer

<400> SEQUENCE: 71
tggttcacat cccgcggct 19

<210> SEQ ID NO 72
<211> LENGTH: 20
<212> TYPE: DNA
<213> ORGANISM: Artificial
<220> FEATURE:
<223> OTHER INFORMATION: synthetic CDKN2A (p14ARF) reverse primer

<400> SEQUENCE: 72
tggctcctca gtagcatcag 20

<210> SEQ ID NO 73
<211> LENGTH: 23
<212> TYPE: DNA
<213> ORGANISM: Artificial
<220> FEATURE:
<223> OTHER INFORMATION: synthetic PPARA forward primer

<400> SEQUENCE: 73
tgaagttcaa tgcactggaa ctg 23

<210> SEQ ID NO 74
<211> LENGTH: 20
<212> TYPE: DNA
<213> ORGANISM: Artificial
<220> FEATURE:
<223> OTHER INFORMATION: synthetic PPARA reverse primer

<400> SEQUENCE: 74
caggacgatc tccacagcaa 20

<210> SEQ ID NO 75
<211> LENGTH: 23
<212> TYPE: DNA
<213> ORGANISM: Artificial
<220> FEATURE:
<223> OTHER INFORMATION: synthetic PPARG forward primer

<400> SEQUENCE: 75
tggagtccac gagatcattt aca 23

<210> SEQ ID NO 76
<211> LENGTH: 19
<212> TYPE: DNA
<213> ORGANISM: Artificial
<220> FEATURE:
<223> OTHER INFORMATION: synthetic PPARG reverse primer

<400> SEQUENCE: 76
agccttggcc ctcggatat 19

<210> SEQ ID NO 77
<211> LENGTH: 21
<212> TYPE: DNA
<213> ORGANISM: Artificial
<220> FEATURE:
<223> OTHER INFORMATION: synthetic PPARD forward primer

<400> SEQUENCE: 77
cactgagttc gccaagagca t 21

<210> SEQ ID NO 78
<211> LENGTH: 23
<212> TYPE: DNA
<213> ORGANISM: Artificial
<220> FEATURE:
<223> OTHER INFORMATION: synthetic PPARD reverse primer

<400> SEQUENCE: 78
cacgccatac ttgagaaggg taa 23

<210> SEQ ID NO 79
<211> LENGTH: 23
<212> TYPE: DNA
<213> ORGANISM: Artificial
<220> FEATURE:
<223> OTHER INFORMATION: synthetic CD44 forward primer

<400> SEQUENCE: 79
gctagtgatc aacagtggca atg 23

<210> SEQ ID NO 80
<211> LENGTH: 18
<212> TYPE: DNA
<213> ORGANISM: Artificial
<220> FEATURE:
<223> OTHER INFORMATION: synthetic CD44 reverse primer

<400> SEQUENCE: 80
gctggcctct ccgttgag 18

<210> SEQ ID NO 81
<211> LENGTH: 22

```
<212> TYPE: DNA
<213> ORGANISM: Artificial
<220> FEATURE:
<223> OTHER INFORMATION: synthetic PTGS1 forward primer

<400> SEQUENCE: 81

tgttcggtgt ccagttccaa ta                                              22


<210> SEQ ID NO 82
<211> LENGTH: 22
<212> TYPE: DNA
<213> ORGANISM: Artificial
<220> FEATURE:
<223> OTHER INFORMATION: synthetic PTGS1 reverse primer

<400> SEQUENCE: 82

tgccagtggt agagatggtt ga                                              22


<210> SEQ ID NO 83
<211> LENGTH: 22
<212> TYPE: DNA
<213> ORGANISM: Artificial
<220> FEATURE:
<223> OTHER INFORMATION: synthetic HMGA1 forward primer

<400> SEQUENCE: 83

acaactccag gaaggaaacc aa                                              22


<210> SEQ ID NO 84
<211> LENGTH: 19
<212> TYPE: DNA
<213> ORGANISM: Artificial
<220> FEATURE:
<223> OTHER INFORMATION: synthetic HMGA1 reverse primer

<400> SEQUENCE: 84

cgaggactcc tgcgagatg                                                  19


<210> SEQ ID NO 85
<211> LENGTH: 23
<212> TYPE: DNA
<213> ORGANISM: Artificial
<220> FEATURE:
<223> OTHER INFORMATION: synthetic CKSAS2 forward primer

<400> SEQUENCE: 85

tgaagaggag tggaggagac ttg                                             23


<210> SEQ ID NO 86
<211> LENGTH: 24
<212> TYPE: DNA
<213> ORGANISM: Artificial
<220> FEATURE:
<223> OTHER INFORMATION: synthetic CKSHS2 reverse primer

<400> SEQUENCE: 86

gaatatgtgg ttctggctca tgaa                                            24


<210> SEQ ID NO 87
<211> LENGTH: 22
<212> TYPE: DNA
<213> ORGANISM: Artificial
<220> FEATURE:
<223> OTHER INFORMATION: synthetic p100 coactivator forward primer

<400> SEQUENCE: 87
```

```
gagaaggagc gatctgctag ct                                            22


<210> SEQ ID NO 88
<211> LENGTH: 23
<212> TYPE: DNA
<213> ORGANISM: Artificial
<220> FEATURE:
<223> OTHER INFORMATION: synthetic p100 coactivator reverse primer

<400> SEQUENCE: 88

cacgtagaag tgcaggtcat cag                                           23
```

METHOD TO PREDICT OR DIAGNOSE A GASTOINTESTINAL DISORDER OR DISEASE

CROSS REFERENCE TO RELATED APPLICATIONS

The application is a continuation of patent application Ser. No. 12/670,854, filed Jun. 21, 2010, now U.S. Pat. No. 8,883,400, which is a U.S. National Stage Application filed under 35 U.S.C. 371 and claims priority to International Application No. PCT/US08/71090, filed Jul. 25, 2008, which application claims priority under 35 U.S.C. §119 to U.S. Provisional Application Ser. No. 60/952,194, filed Jul. 26, 2007, the disclosures of which are incorporated herein by reference.

TECHNICAL FIELD

The invention relates to predicting the probability that a subject has a predisposition to or has a gastrointestinal tract disease or disorder.

BACKGROUND

Presently, there are no biological tests in clinical use to predict a subject's clinical development of a gastrointestinal disorder or cancer based upon gene expression profiling.

SUMMARY

The disclosure provides a method for determining if a subject has or is at risk of having a gastrointestinal disease or disorder comprising: measuring an FHSH biomarker panel, a polyp biomarker panel, a rectal bleeding biomarker panel, a cancer biomarker panel or any combination thereof, wherein a change in one or more of the biomarker panels relative to a control is indicative of a subject that has or is at risk of having a gastrointestinal disease or disorder. In one aspect, the method comprises measuring an FHSH biomarker panel and comparing the measurements to a control wherein a change relative to the control is indicative that the subject has a predisposition or risk of developing a cancerous lesion. In another aspect, if a subject is identified as having a predisposition or risk of developing a polyp or cancerous lesion, the subject is further monitored for a polyp biomarker panel. In another aspect, the subject is further monitored for a cancer biomarker panel. In yet another aspect, a polyp or cancer biomarker panel is monitored and comparing the measurements to a control wherein a change relative to the control is indicative that the subject has or is at risk of developing a polyp or cancerous lesion.

The disclosure also provides a method of determining whether a subject has rectal bleeding comprising measuring a rectal bleeding biomarker panel, wherein a subject that is positive for the panel has rectal bleeding.

The disclosure also provides kits and compositions for carrying out the methods described herein. In one aspect, the kit comprises a FHSH biomarker panel, a polyp biomarker panel, a cancer biomarker panel, a rectal bleeding biomarker panel or any combination thereof.

The details of one or more embodiments are set forth in the accompanying drawings and the description below. Other features, objects, and advantages will be apparent from the description and drawings, and from the claims.

DETAILED DESCRIPTION

Figure 1A:
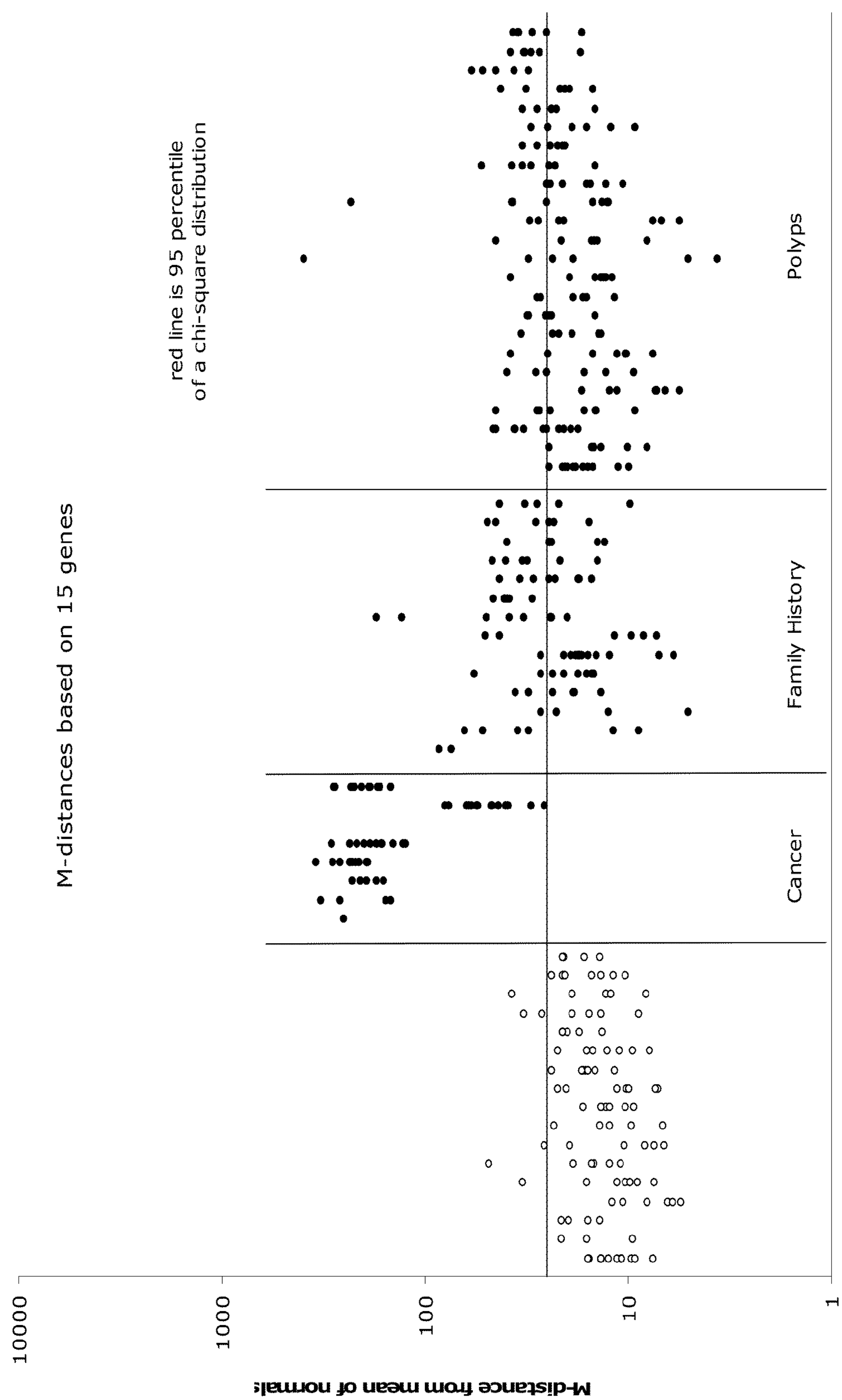
FIG. 1A-C shows the Mahalanobis distance for biopsy samples, taken from (left to right), controls, resected colon cancer, individuals with family history, and individuals with polyps (67 subject and 15 genes), (B) shows the same analysis carried out on a second patient pool, one including individuals with no polyps or family/self history (Control), individuals with family history, individuals with polyps, and (C) shows the same analysis carried out on rectal smear samples taken from the same individuals.

As used herein and in the appended claims, the singular forms "a," "and," and "the" include plural referents unless the context clearly dictates otherwise. Thus, for example, reference to "a polynucleotide" includes a plurality of such polynucleotides and reference to "the variant" includes reference to one or more variants known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

The disclosure provides a number of biomarkers useful for predicting a subject's predisposition or the existence of a gastrointestinal disease or disorder. The biomarkers identified herein can be used in combination with additional predictive tests including, but not limited to, additional SNPs, mutations, and clinical tests (including a plurality of biomarker panels disclosed herein).

The methods and compositions of the disclosure can be used in an outpatient clinic or inpatient environment. Outpatient clinical diagnostics are useful to reduce costs of unnecessary, often invasive or painful, procedures. As a screening tool, colonoscopy is considered too expensive, both to the patients and to the insurance carriers, and carries with it a small percentage of risks and complications. Barium enema and CT colonography (or virtual colonoscopy), like colonoscopy, will provide for a complete colon examination, but small polyps or even small cancers can be missed. The cost is high, and higher still if a polyp or cancer or even a suggestion of a polyp or cancer will be interpreted by the radiologists, requiring the additional procedure of colonoscopy for confirmation. The barium enema, the CT colonography and the colonoscopy procedures all require the patients to have a thorough mechanical bowel preparation the day before. The diagnostic tests and compositions described herein are useful to identify, diagnose, and prognose subjects that should be followed or treated for gastrointestinal diseases and disorders including the development of polyps, cancerous lesions or other non-cancerous inflammatory diseases.

An adenoma, colon adenoma, and polyp are used herein to describe any precancerous neoplasia of the colon. Precancerous colon neoplasias are referred to as adenomas or adenomatous polyps. Adenomas are typically small mushroom-like or wart-like growths on the lining of the colon and do not invade into the wall of the colon. Adenomas may be visualized through a device such as a colonoscope or flexible sigmoidoscope. Several studies have shown that patients who undergo screening for and removal of adenomas have a decreased rate of mortality from colon cancer. For this and other reasons, it is generally accepted that adenomas are an obligate precursor for the vast majority of colon cancers. When a colon neoplasia invades into the basement membrane of the colon, it is considered a colon cancer. The most widely used staging systems generally use at least one of the following characteristics for staging: the extent of tumor penetration into the colon wall, with greater penetration generally correlating with a more dangerous tumor; the extent of invasion of the tumor through the colon wall and into other neighboring tissues, with greater invasion generally correlating with a more dangerous tumor; the extent of invasion of the tumor into the regional lymph nodes, with greater invasion generally correlating with a more dangerous tumor; and the extent of metastatic invasion into more distant tissues, such as the liver, with greater metastatic invasion generally correlating with a more dangerous disease state.

An allele refers to a particular form of a genetic locus, distinguished from other forms by its particular nucleotide sequence, or one of the alternative polymorphisms found at a polymorphic site.

A biological sample refers to a sample obtained from a subject wherein the sample comprises cells, or can be cell free. The biological sample can be blood, sputum, saliva, tissue, stool, urine, serum cerebrospinal, cells, secretions or the like. Where the sample is a tissue, the tissue sample can be obtained by biopsy. Biopsy samples can be obtained from the gastrointestinal tract (e.g., from a segment of colon between the cecum and the hepatic flexure were classified as ascending colon samples; those from the segment of colon between the hepatic flexure and the splenic flexure as transverse colon samples; those from the segment of colon below the splenic flexure as descending colon; those from the winding segment of colon below the descending colon were classified as rectosigmoid colon samples (approximately 5-25 cm from rectum, typically about 5-10 cm)). The biological sample can be obtained non-invasively (e.g., by swab). The swab, for example, can be obtained from the mouth or rectum. In one embodiment, the swab is obtained from the distal portion of the gastrointestinal tract (e.g., the last 5-25 cm is obtained from the rectum). In yet another embodiment, the swab is collected from the buccal area (e.g., the mouth, cheek, sublingual area, gums and the like). A minimally invasive method, such as a swab, or a non-invasive sampling method, such as a stool sample can be obtained and used in the methods of the disclosure. A biopsy will tend to have a more heterogenous mixture of cell-types (e.g., epithelial, stromal and endothelial cells) compared to a swab sample, which has a higher percentage of cell types on the colorectal surface (e.g., epithelial and inflammatory cells).

A biomarker refers to a detectable biological entity associated with a particular phenotype or risk of developing a particular phenotype. The biological entity can be a polypeptide or polynucleotide. A biomarker to be detected is referred to as a target. For example, a target polynucleotide refers to a biomarker comprising a polynucleotide (e.g., an mRNA or cDNA) that is to be detected. In another example, a target polypeptide refers to a protein expressed (i.e., transcribed and translated) that is to be detected. A biomarker, as defined by the National Institutes of Health (NIH), refers to a molecular indicator of a specific biological property; a biochemical feature or facet that can be used to measure the progress of disease or the effects of treatment. A panel of biomarkers is a selection of at least two biomarkers. Biomarkers may be from a variety of classes of molecules. In principle, the larger the number of biomarkers used the more sensitive the analysis will be. The panel can comprise from 2 to sixteen or more biomarkers. In one aspect, the panel comprises 2, 3, 4, 5, 6, 7, 8, 9, 10, 11, 12, 13, 14, 15, 16 or more biomarkers. The disclosure demonstrates that for individuals with cancer, three or four genes, such as COX-2, IL-8 and CD44, can suffice. However, for individuals with polyps or with history of cancer fine-tuning the analysis by adding to or otherwise modifying the biomarker panel increases specificity.

The term "colon" as used herein is intended to encompass the right colon (including the cecum), the transverse colon, the left colon, and the rectum.

A colorectal cancer and colon cancer are used interchangeably herein to refer to any cancerous neoplasia of the colon (including the rectum). The concept of polyp to cancer sequence is well established, and it is widely accepted that removal of pre-malignant colorectal polyps will lead to a significant decrease of the incidence of colorectal cancer. Furthermore, clinical data has shown that early detection and curative surgical resection of colorectal cancer will significantly improve survival rates.

Subjects with either a family history of any cancer or personal history of any cancer and with no polyps during a current colonoscopy are referred to as FHSH subjects. Subjects with polyps and with or without family or self history of any cancer are referred to as polyps subjects and comprise a FHSH subject's biomarker panel. Subjects with colon cancer are referred to as cancer subjects and comprise a cancer subject's biomarker panel.

A fecal occult blood test (FOBT) is a test used to check for hidden blood in the stool. Sometimes cancers or polyps can bleed, and FOBT is used to detect small amounts of bleeding. In addition, screening tests (such as a rectal examination, proctoscopy, and colonoscopy) may be done regularly in patients who are at high risk of colon cancer or who have a positive FOBT and/or biomarker results. The proctoscopy examination finds about half of all colon and rectal cancers. After treatment, a blood test and x-rays may be done to screen for recurrence.

Colorectal cancer, also referred to as colon cancer or large bowel cancer, includes cancerous growths in the colon, rectum and appendix. Many colorectal cancers arise from adenomatous polyps in the colon. These growths are usually benign, but some may develop into cancer over time. The majority of the time, the diagnosis of localized colon cancer is through colonoscopy. Therapy is usually through surgery, which in many cases is followed by chemotherapy. Polyps of the colon, particularly adenomatous polyps, are a risk factor for colon cancer. The removal of colon polyps at the time of colonoscopy reduces the subsequent risk of colon cancer. Individuals who have previously been diagnosed and treated for colon cancer are at risk for developing colon cancer in the future. Women who have had cancer of the ovary, uterus, or breast are at higher risk of developing colorectal cancer. Family history of colon cancer, especially in a close relative before the age of 55 or multiple relatives, increases the risk of cancer in a subject.

Gastrointestinal inflammation refers to inflammation of a mucosal layer of the gastrointestinal tract, and encompasses acute and chronic inflammatory conditions. Acute inflammation is generally characterized by a short time of onset and infiltration or influx of neutrophils. Chronic inflammation is generally characterized by a relatively longer period of onset and infiltration or influx of mononuclear cells. Chronic inflammation can also be characterized by periods of spontaneous remission and spontaneous occurrence. The mucosal layer of the gastrointestinal tract includes mucosa of the bowel (including the small intestine and large intestine), rectum, stomach (gastric) lining, oral cavity, and the like.

Chronic gastrointestinal inflammation refers to inflammation of the mucosa of the gastrointestinal tract that is characterized by a relatively longer period of onset, is long-lasting (e.g., from several days, weeks, months, or years and up to the life of the subject), and is associated with infiltration or influx of mononuclear cells and can be further associated with periods of spontaneous remission and spontaneous occurrence. Examples of chronic gastrointestinal inflammation include inflammatory bowel disease (IBD), colitis induced by environmental insults (e.g., gastrointestinal inflammation (e.g., colitis) caused by or associated with (e.g., as a side effect) a therapeutic regimen, such as administration of chemotherapy, radiation therapy, and the like), colitis in conditions such as chronic granulomatous disease (Schappi et al. Arch Dis Child. 2001 February; 84(2):147-151), celiac disease, celiac sprue (a heritable disease in which the intestinal lining is inflamed in response to the ingestion of a protein known as gluten), food allergies, gastritis, infectious gastritis or enterocolitis (e.g., *Helicobacter pylori*-infected chronic active gastritis) and other forms of gastrointestinal inflammation caused by an infectious agent, and other like conditions.

As used herein, “inflammatory bowel disease” or “IBD” refers to any of a variety of diseases characterized by inflammation of all or part of the intestines. Examples of inflammatory bowel disease include, but are not limited to, Crohn’s disease, Barrett’s disease and ulcerative colitis. Reference to IBD throughout the specification is often referred to in the specification as exemplary of gastrointestinal inflammatory conditions, and is not meant to be limiting. The term IBD includes pseudomembranous colitis, hemorrhagic colitis, hemolytic-uremic syndrome colitis, collagenous colitis, ischemic colitis, radiation colitis, drug and chemically induced colitis, diversion colitis, ulcerative colitis, irritable bowel syndrome, irritable colon syndrome, Barrett’s disease and Crohn’s disease; and within Crohn’s disease all the subtypes including active, refractory, and fistulizing and Crohn’s disease.

A non-colorectal cancer inflammatory disease or disorder of the gastrointestinal tract refers to an inflammation of the gastrointestinal tract in the absence of a cancerous lesion, tumor or lesion. A non-colorectal cancer inflammatory disease or disorder of the gastrointestinal tract includes inflammatory bowel disease.

A gene refers to a segment of genomic DNA that contains the coding sequence for a protein, wherein the segment may include promoters, exons, introns, and other untranslated regions that control expression.

A genotype is an unphased 5' to 3' sequence of nucleotide pair(s) found at a set of one or more polymorphic sites in a locus on a pair of homologous chromosomes in an individual. As used herein, genotype includes a full-genotype and/or a sub-genotype.

Genotyping is a process for determining a genotype of an individual.

A haplotype is a 5' to 3' sequence of nucleotides found at a set of one or more polymorphic sites in a locus on a single chromosome from a single individual.

Haplotype pair is two haplotypes found for a locus in a single individual.

Haplotyping is the process for determining one or more haplotypes in an individual and includes use of family pedigrees, molecular techniques and/or statistical inference.

A genetic locus refers to a location on a chromosome or DNA molecule corresponding to a gene or a physical or phenotypic feature, where physical features include polymorphic sites.

Polymorphic site (PS) is a position on a chromosome or DNA molecule at which at least two alternative sequences are found in a population.

A polymorphism refers to the sequence variation observed in an individual at a polymorphic site. Polymorphisms include nucleotide substitutions, insertions, deletions and microsatellites and may, but need not, result in detectable differences in gene expression or protein function. A single nucleotide polymorphism (SNP) is a single change in the nucleotide variation at a polymorphic site.

An oligonucleotide probe or a primer refers to a nucleic acid molecule of between 8 and 2000 nucleotides in length, or is about 6 and 1000 nucleotides in length. More particularly, the length of these oligonucleotides can range from about 8, 10, 15, 20, or 30 to 100 nucleotides, but will typically be about 10 to 50 (e.g., 15 to 30 nucleotides). The appropriate length for oligonucleotides in assays of the disclosure under a particular set of conditions may be empirically determined by one of skill in the art.

Oligonucleotide primers and probes can be prepared by any suitable method, including, for example, cloning and restriction of appropriate sequences and direct chemical synthesis. The oligonucleotide primers and probes can contain conventional nucleotides, as well as any of a variety of analogs. For example, the term “nucleotide”, as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —$NR_2$ or halogen groups, where each R is independently H, $C_1$-$C_6$ alkyl or $C_5$-$C_{14}$ aryl. Exemplary riboses include, but are not limited to, 2'-($C_1$-$C_6$)alkoxyribose, 2'-($C_5$-$C_{14}$)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-($C_1$-$C_6$)alkylribose, 2'-deoxy-3'-($C_1$-$C_6$)alkoxyribose and 2'-deoxy-3'-($C_5$-$C_{14}$)aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-α-anomeric nucleotides, 1'-α-anomeric nucleotides, 2'-4'- and 3'-4'-linked and other “locked” or “LNA”, bicyclic sugar modifications (see, e.g., PCT published application nos. WO 98/22489, WO 98/39352; and WO 99/14226). Exemplary LNA sugar analogs within a polynucleotide include, but are not limited to, the structures: where B is any nucleotide base.

Modifications at the 2'- or 3'-position of ribose include, but are not limited to, hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo. Nucleotides include, but are not limited to, the natural D optical isomer, as well as the L optical isomer forms (see, e.g., Garbesi (1993) Nucl. Acids Res. 21:4159-65; Fujimori (1990) J. Amer. Chem. Soc. 112:7435; Urata, (1993) Nucleic Acids Symposium Ser. No. 29:69-70). When the nucleotide base is purine, e.g. A or G, the ribose sugar is attached to the $N_9$-position of the nucleotide base. When the nucleotide base is pyrimidine, e.g. C, T or U, the pentose sugar is attached to the $N_1$-position of the nucleotide base, except for pseudouridines, in which the pentose sugar is attached to the $C_5$ position of the uracil nucleotide base (see, e.g., Kornberg and Baker, (1992) DNA Replication, 2nd Ed., Freeman, San Francisco, Calif.). The 3' end of the probe can be functionalized with a capture or detectable label to assist in detection of a target polynucleotide or of a polymorphism.

Any of the oligonucleotides or nucleic acids of the disclosure can be labeled by incorporating a detectable label measurable by spectroscopic, photochemical, biochemical, immunochemical, or chemical means. For example, such labels can comprise radioactive substances (e.g., $^{32}P$, $^{35}S$, $^{3}H$, $^{125}I$), fluorescent dyes (e.g., 5-bromodesoxyuridin, fluorescein, acetylaminofluorene, digoxigenin), biotin, nanoparticles, and the like. Such oligonucleotides are typically labeled at their 3' and 5' ends.

A probe refers to a molecule which can detectably distinguish changes in gene expression or can distinguish between target molecules differing in structure. Detection can be accomplished in a variety of different ways depending on the type of probe used and the type of target molecule. Thus, for example, detection may be based on discrimination of activity levels of the target molecule, but typically is based on detection of specific binding. Examples of such specific binding include antibody binding and nucleic acid probe hybridization. Thus, for example, probes can include enzyme substrates, antibodies and antibody fragments, and nucleic acid hybridization probes (including primers useful for polynucleotide amplification and/or detection). Thus, in one embodiment, the detection of the presence or absence of the at least one target polynucleotide involves contacting a biological sample with a probe or primer pair, typically an oligonucleotide probe or primer pair, where the probe/primers hybridizes with a form of a target polynucleotide in the biological sample containing a complementary sequence, where the hybridization is carried out under selective hybridization conditions. Such an oligonucleotide probe can include one or more nucleic acid analogs, labels or other substituents or moieties so long as the base-pairing function is retained.

A reference or control population refers to a group of subjects or individuals who are predicted to be representative of the genetic variation found in the general population having a particular genotype or expression profile. Typically, the reference population represents the genetic variation in the population at a certainty level of at least 85%, typically at least 90%, least 95% and but commonly at least 99%. The reference or control population can include subjects who individually have not demonstrated any gastrointestinal disease or disorder and can include individuals whose family line does not or has not demonstrated any gastrointestinal diseases or disorders.

A subject comprises an individual (e.g., a mammalian subject or human) whose gene expression profile, genotypes or haplotypes or response to treatment or disease state are to be determined. A control subject refers to individuals with no polyps and no family or self history of cancer or known upper GI problem. Subjects with either a family history of any cancer or personal history of any cancer, and with no polyps during a current colonoscopy are referred to as FHSH subjects. Subjects with polyps and with or without family or self history of any cancer are referred to as polyps subjects and comprise a FHSH subject's biomarker panel.

In some instances a subject may not have access or know their familial history. In such instances, the diagnostics of the disclosure can be used to determine if they have a predisposition to a gastrointestinal disease or disorder based upon a FHSH biomarker panel. In other aspects, where a subject is identified as having a FHSH GI disease or disorder, the subject may be monitored for changes in biomarker expression indicative of cancer lesions or polyps based upon a cancer biomarker panel. Where a biomarker panel associated with colorectal cancer is present the subject may be monitored by, for example, by colonoscopy for early detection and removal of polyps or cancerous lesions. One advantage of the biomarker panels provided herein is that the panel may be detected by swab collection (e.g., swab of the rectal 5-10 cm) or a buccal swab. Such procedures may be performed in an outpatient setting. As indicated above, statistics indicate that early detection and removal of cancerous lesion and polyps reduce morbidity and mortality of subjects.

One embodiment of what is disclosed is the measurement of at least one or a panel of biomarkers with the selectivity and sensitivity required for managing and diagnosing subjects that have or may have a predisposition to a gastrointestinal disease or disorder. Table 1 provides a list of polynucleotide biomarkers useful in the methods and compositions of the disclosure (each of the sequences associated with the Enterez Accession Nos. set forth in Table 1 are incorporated herein by reference).

TABLE 1

| SEQ ID NO: polynucleotide and polypeptide | NCBI Entrez Database | Name | Abbreviation |
|---|---|---|---|
| 1 and 2 | XM_031289 | Interleukin-8 | IL8 |
| 3 and 4 | NM_000389 | cyclin-dependent kinase inhibitor 1A (p21, Cip1) | P21 |
| 5 and 6 | XM_030326 | CD44 antigen | CD44 |
| 7 and 8 | M94582 | Interleukin 8 receptor B | CXCR2 |
| 9 and 10 | X54489 | Melanoma growth stimulatory activity | Gro-alpha |
| 11 and 12 | NM_002090 | Chemokine (C-X-C motif) ligand3 | Gro-gamma |
| 13 and 14 | XM_003059 | Peroxisome proliferative activated receptor, gamma | PPAR-gamma |
| 15 and 16 | NM_006238 | Peroxisome proliferative activated receptor, delta | PPAR-delta |
| 17 and 18 | AX057136 | c-Myc | c-Myc |
| 19 and 20 | XM_032429 | Secreted phosphoprotein 1 | SPP1 (OPN) |
| 21 and 22 | XM_044882 | Prostaglandin-endoperoxide synthase 1 | COX-1 |
| 23 and 24 | XM_051900 | Prostaglandin-endoperoxide synthase 2 | COX-2 |
| 25 and 26 | NM_005036 | Peroxisome proliferative activated receptor, alpha | PPAR-alpha |
| 27 and 28 | NM_000757 | Macrophage colony stimulating factor 1 | MCSF-1 |

TABLE 1-continued

| SEQ ID NO: polynucleotide and polypeptide | NCBI Entrez Database | Name | Abbreviation |
|---|---|---|---|
| 29 and 30 | M64349 | Cyclin-D | Cyc-D |
| 31 and 32 | NM_000331 | Serum amyloid A1 | SAA1 |
| 33 and 34 | NM_002131 | *Homo sapiens* high mobility group AT-hook 1 (HMGA1) | HMGA1 |
| 35 and 36 | X54942 X55506 | CKSHS2 | CKSHS2 |
| 37 and 38 | U22055 | Human 100 kDa coactivator | p100 activator |
| 39 and 40 | NM_005555 | *Homo sapiens* keratin 6B | LCN2 |
| 41 and 42 | BC021998 | *Homo sapiens* cyclin-dependent kinase inhibitor 2A | hCDK2a |
| 43 and 44 | NM_058195 | *Homo sapiens* cyclin-dependent kinase inhibitor 2A | hCDK2a alt. |

Naturally occurring variants (e.g., polymorphisms) of any of the foregoing polynucleotides identified in Table 1 are encompassed by the disclosure. Identification of such naturally occurring polymorphisms are routinely identified or are known in the art. For example, polymorphisms of IL-8 and CXCR2 include SNP −251, −353/+1530, −353/+3331, and +1530/+3331 of IL-8 and +785/+1208 of CXCR2. Others include IL1B −31 SNP (C to T), IL10 −819 T/T. RS numbers include rs1143627 (IL1B), rs2243250 and rs1143634 (IL4), rs1801282 (PPAR-gamma), rs4073 (IL8), rs1800629 (TNF), and rs20417, rs5277, rs20432 and rs5275 (COX2).

In one aspect of the disclosure, expression levels of polynucleotides comprising biomarkers, or fragments thereof, indicated in SEQ ID NOs: 1, 3, 5, 7, 9, 11, 13, 15, 17 19, 21, 23, 25, 27, 29, 31, 33, 35, 37, 39, 41 or 43 are used in the determination of a gastrointestinal disease or disorder or a predisposition to a gastrointestinal disease or disorder. Such analysis of polynucleotide expression levels is frequently referred to in the art as gene expression profiling. In gene expression profiling, levels of mRNA in a sample are measured as a leading indicator of a biological state, in this case, as an indicator of a gastrointestinal disease or disorder or a predisposition thereto. One of the most common methods for analyzing gene expression profiling is to create multiple copies from mRNA in a biological sample using a process known as reverse transcription. In the process of reverse transcription, the mRNA from the sample is used to create DNA copies of the corresponding mRNA. The copies made from mRNA are referred to as copy DNA, or cDNA. mRNA is somewhat unstable and subject degradation by RNAses. In one aspect, the RNA can be protected by using RNAse inhibitors and cocktails known in the art. Table 2 provides probes and primers useful to detecting a polynucleotide biomarker of the disclosure.

TABLE 2

| Sequence ID No./ID | Sequence | Name |
|---|---|---|
| 45. Forward Primer | agatattgca cgggagaata tacaaa | Interleukin 8 |
| 46. Reverse Primer | tcaattcctg aaattaaagt tcggata | |
| 47. Forward Primer | tctgcagagt tggaagcact cta | Prostaglandin-endoperoxide synthase 2 |
| 48. Reverse Primer | gccgaggctt ttctaccaga a | |
| 49. Forward Primer | catggcttga tcagcaagga | Interleukin 8 receptor B (CXCR2) |
| 50. Reverse Primer | tggaagtgtg ccctgaagaa g | |
| 51. Forward Primer | caaggagctg acttcggaac taa | Lipocalin 2 |
| 52. Reverse Primer | agggaagacg atgtggtttt ca | |
| 53. Forward Primer | gggacatgtg gagagcctac tc | Serum amyloid A1 |
| 54. Reverse Primer | catcatagtt cccccgagca t | |
| 55. Forward Primer | aagcagcacc agcaagtgaa g | Macrophage colony stimulating factor 1 |
| 56. Reverse Primer | tcatggcctg tgtcagtcaa a | |
| 57. Forward Primer | acatgccagc cactgtgata g | Melanoma growth stimulatory activity |
| 58. Reverse Primer | ccctgccttc acaatgatct c | |
| 59. Forward Primer | ggaattcacc tcaagaacat cca | Chemokine (C-X-C motif) ligand 3 |
| 60. Reverse Primer | agtgtggcta tgacttcggt ttg | |
| 61. Forward Primer | cagccacaag cagtccagat ta | (OPN) Secreted phosphoprotein 1 |

TABLE 2 -continued

| Sequence ID No./ID | Sequence | Name |
|---|---|---|
| 62. Reverse Primer | cctgactatc aatcacatcg gaat | |
| 63. Forward Primer | ccaggtgctc cacatgacag t | Cyclin D |
| 64. Reverse Primer | aaacaaccaa caacaaggag aatg | |
| 65. Forward Primer | cgtctccaca catcagcaca a | c-Myc |
| 66. Reverse Primer | tcttggcagc aggatagtcc tt | |
| 67. Forward Primer | gcagaccagc atgacagatt tc | Cyclin-dependent kinase inhibitor (p21) |
| 68. Reverse Primer | gcggattagg gcttcctctt | |
| 69. Forward Primer | ggcaccagag gcagtaacca t | Cyclin-dependent kinase inhibitor 2A |
| 70. Reverse Primer | agcctctctg gttctttcaa tcg | |
| 71. Forward Primer | tggttcacat cccgcggct | Alternative reading frame p14 |
| 72. Reverse Primer | tggctcctca gtagcatcag | |
| 73. Forward Primer | tgaagttcaa tgcactggaa ctg | Peroxisome proliferation activated receptor, alpha |
| 74. Reverse Primer | caggacgatc tccacagcaa | |
| 75. Forward Primer | tggagtccac gagatcattt aca | Peroxisome proliferation activated receptor, gamma |
| 76. Reverse Primer | agccttggcc ctcggatat | |
| 77. Forward Primer | cactgagttc gccaagagca t | Peroxisome proliferation activated receptor, delta |
| 78. Reverse Primer | cacgccatac ttgagaaggg taa | |
| 79. Forward Primer | gctagtgatc aacagtggca atg | CD44 antigen |
| 80. Reverse Primer | gctggcctct ccgttgag | |
| 81. Forward Primer | tgttcggtgt ccagttccaa ta | Prostaglandin-endoperoxide synthase 1 |
| 82. Reverse Primer | tgccagtggt agagatggtt ga | |
| 83. Forward Primer | acaactccag gaaggaaacc aa | High-mobility group AT-hook1 isoform B |
| 84. Reverse Primer | cgaggactcc tgcgagatg | |
| 85. Forward Primer | tgaagaggag tggaggagac ttg | CKS1 protein homolog |
| 86. Reverse Primer | gaatatgtgg ttctggctca tgaa | |
| 87. Forward Primer | gagaaggagc gatctgctag ct | 100 kDa coactivator |
| 88. Reverse Primer | cacgtagaag tgcaggtcat cag | |

Methods known in the art can be used to quantitatively measure the amount of mRNA transcribed by cells present in a sample. Examples of such methods include quantitative polymerase chain reaction (PCR), digital PCR, northern and southern blots. PCR allows for the detection and measurement of very low quantities of mRNA using an amplification process. Genes may either be up regulated or down regulated in any particular biological state, and hence mRNA levels shift accordingly.

The following tables identify various biomarker panels and statistics useful in performing the diagnostics of the disclosure.

A polyp biomarker panel based upon a swab comprises one or more of the biomarkers CD44, PPARγ, and COX1. In one aspect, a polyp biomarker panel using a swab comprises the genes listed in Table 3. The percentage shown in Tables 3-10 comprises the percentage of subject in the population showing a change (e.g., an increase or decrease in expression) in the listed biomarkers compared to a control population.

TABLE 3

| Swabs Polyps | % having a change relative to control |
|---|---|
| CD44 | 45.5% ± 2.5% |
| PPARγ | 40.5% ± 2.5% |
| COX 1 | 45.5% ± 2.5% |
| PPARα | 37.0% ± 1.0% |
| SAA1 | 38.0% ± 1.0% |
| OPN = COX2 = IL8 = cMyc = mCSF1 = cycD | 31.0% ± 2.0% |
| Groα | 29.0% ± 1.0% |
| PPARδ | 18.0% ± 5.0% |
| P21 = Groγ | 19.0% ± 1.0% |

A polyp biomarker panel based upon a rectal biopsy comprises one or more of the biomarkers Groα, CXCR2, and PPARδ. The biomarker panel can further comprise P21. In one aspect, a rectal polyp biomarker panel using a biopsy comprises the genes listed in Table 4.

TABLE 4

| Rectal Biopsy Polyps | % having a change relative to control |
|---|---|
| Groα | 60.0% ± 1.0% |
| CXCR2 | 55.0% ± 1.0% |
| PPARδ | 45.0% ± 1.0% |
| P21 | 30.0% ± 1.0% |
| OPN = PPARα = CD44 | 25.0% ± 1.0% |
| PPARγ = SAA1 = COX1 | 20.0% ± 1.0% |
| Groγ = cMyc = mCSF1 | 15.0% ± 1.0% |
| cycD | 5.0% ± 1.0% |
| COX2 | 0% |

A polyp biomarker panel based upon an ascending colon biopsy comprises one or more of the biomarkers P21, mCSF-1, cycD, and SAA1. In one aspect, an ascending colon polyp biomarker panel using a biopsy comprises the genes listed in Table 5.

TABLE 5

| AS Biopsy Polyps | % having a change relative to control |
|---|---|
| P21 = mCSF1 | 45.0% ± 1.0% |
| cycD | 41.0% ± 1.0% |
| SAA1 | 32.0% ± 1.0% |
| Groα = OPN = CXCR2 = PPARα = CD44 | 27.0% ± 1.0% |
| COX 1 = Groγ = IL-8 | 23.0% ± 1.0% |
| PPARδ | 18.0% ± 1.0% |
| COX2 | 14.0% ± 1.0% |
| cMyc = PPARγ | 5.0% ± 1.0% |

A polyp biomarker panel based upon a descending colon biopsy comprises one or more of the biomarkers COX-1, CXCR2, cycD, PPARδ and SAA1. In one aspect, a descending colon polyp biomarker panel using a biopsy comprises the genes listed in Table 6.

TABLE 6

| DS Biopsy Polyps | % having a change relative to control |
|---|---|
| CXCR2 = COX1 | 39.0% ± 1.0% |
| cycD = PPARδ | 35.0% ± 1.0% |
| SAA1 | 30.0% ± 1.0% |
| PPARγ = P21 | 26.0% ± 1.0% |
| mCSF-1 = cMyc = Groα | 22.0% ± 1.0% |
| CD44 = PPARα | 17.0% ± 1.0% |
| IL-8 = COX2 | 13.0% ± 1.0% |
| OPN = Groγ | 9.0% ± 1.0% |

A FHSH biomarker panel based upon a rectal swab comprises one or more of the biomarkers Groα, CD44, and COX1. In one aspect, a FHSH biomarker panel using a swab comprises the genes listed in Table 7.

TABLE 7

| SWABS FHSH | % having a change relative to control |
|---|---|
| Groα | 50.0% ± 1.0% |
| CD44 | 46.0% ± 1.0% |
| COX1 = Groγ | 42.0% ± 1.0% |
| OPN = COX2 = cMyc | 38.0% ± 1.0% |
| mCSF-1 | 33.0% ± 2.0% |
| PPARγ = P21 = cycD = PPARδ | 31.0% ± 1.0% |
| SAA1 | 27.0% ± 1.0% |
| IL8 | 23.0% ± 1.0% |
| CXCR2 | 19.0% ± 1.0% |
| PPARα | 15.0% ± 1.0% |

A FHSH biomarker panel based upon a rectal biopsy comprises one or more of the biomarkers GROα, PPARδ, SAA1, COX1 and CXCR2. In one aspect, a rectal biopsy FHSH biomarker panel using a biopsy comprises the genes listed in Table 8.

TABLE 8

| RECTAL BIOPSIES FHSF | % having a change relative to control |
|---|---|
| Groα = PPARδ = SAA1 | 40.0% ± 1.0% |
| COX1 = CXCR2 | 36.0% ± 1.0% |
| cMyc = CD44 | 32.0% ± 1.0% |
| P21 | 28.0% ± 1.0% |
| OPN = PPARα = COX2 | 24.0% ± 1.0% |
| Groγ | 20.0% ± 1.0% |
| IL8 | 16.0% ± 1.0% |
| PPARγ = mCSF1 | 12.0% ± 1.0% |
| cycD | 4.0% ± 1.0% |

A FHSH biomarker panel based upon an ascending colon biopsy comprises one or more of the biomarkers m-CSF1, p21, and cycD. In one aspect, a ascending colon biopsy FHSH biomarker panel using a biopsy comprises the genes listed in Table 9.

TABLE 9

| AS BIOPSIES FHSF | % having a change relative to control |
|---|---|
| mCSF1 | 60.0% ± 1.0% |
| P21 | 46.0% ± 1.0% |
| cycD | 40.0% ± 1.0% |
| SAA1 = cMyc = CXCR2 = Groγ | 26.0% ± 1.0% |
| Groα = IL8 = Cox1 | 23.0% ± 1.0% |
| CD44 | 20.0% ± 1.0% |
| PPARδ | 17.0% ± 1.0% |
| OPN | 14.0% ± 1.0% |
| PPARα = COX-2 = PPARγ | 11.0% ± 1.0% |

A FHSH biomarker panel based upon a descending colon biopsy comprises one or more of the biomarkers CXCR2, cycD and SAA1. In one aspect, a descending colon biopsy FHSH biomarker panel using a biopsy comprises the genes listed in Table 10.

TABLE 10

| DS BIOPSIES FHSF | % having a change relative to control |
|---|---|
| CXCR2 | 42.0% ± 1.0% |
| cycD | 39.0% ± 1.0% |
| SAA1 | 33.0% ± 1.0% |
| mCSF1-PPARδ | 31.0% ± 1.0% |
| Groγ | 28.0% ± 1.0% |
| P21 = COX2 = Groα | 25.0% ± 1.0% |
| PPARγ | 19.0% ± 1.0% |
| cMyc = IL8 | 17.0% ± 1.0% |
| CD44 = OPN | 11.0% ± 1.0% |
| PPARα = COX1 | 8.0% ± 1.0% |

A rectal bleeding biomarker panel based upon a swab comprises one or more of the biomarkers COX2, OPN, PPARγ, COX1 and GROα. In one aspect, a rectal bleeding biomarker panel using a swab comprises the genes listed in Table 11. Rectal bleeding biomarkers can be indicative of a non-cancerous inflammatory disease or disorder.

TABLE 11

| SWABS RECTAL BLEEDING | % having a change relative to control |
|---|---|
| COX2 | 53.0% ± 1.0% |
| OPN = PPARγ | 47.0% ± 1.0% |
| COX1 = Groα | 40.0% ± 1.0% |
| CXCRZ = IL8 = CD44 = cycD | 33.0% ± 1.0% |
| PPARα = Groγ = PPARδ | 27.0% ± 1.0% |
| P21 | 20.0% ± 1.0% |
| cMyc = mCSF1 | 13.0% ± 1.0% |
| SAA1 | 7.0% ± 1.0% |

A rectal bleeding biomarker panel based upon a biopsy comprises one or more of the biomarkers Groα, Groγ, PPARδ and SAA1. In one aspect, a rectal bleeding biomarker panel using a biopsy comprises the genes listed in Table 12.

TABLE 12

| BIOPSIES RECTAL BLEEDING | % having a change relative to control |
|---|---|
| Groα = Groγ = PPARδ | 54.0% ± 1.0% |
| SAA1 | 46.0% ± 1.0% |
| CXCR2 = mCSF1 | 38.0% ± 1.0% |
| OPN = PPARα = CD44 | 31.0% ± 1.0% |
| COX2 = cMyc | 23.0% ± 1.0% |
| IL8 = PPARγ = P21 = cycD | 15.0% ± 1.0% |
| COX1 | 13.0% ± 1.0% |

A cancer biomarker panel based upon a swab in the absence of an RNA protection cocktail comprises the biomarkers PPARα, CXCR2, cMyc and CD44. In one aspect, a cancer biomarker panel using a swab comprises the genes listed in Table 13.

TABLE 13

| SWABS CANCER (PBS) | % having a change relative to control |
|---|---|
| CXCR2 = PPARα = cMyc = CD44 | 100% |
| OPN = COX1 = COX2 = Groα = Groγ = IL8 = PPARγ = P21 = SAA1 | 75.0% ± 1.0% |
| cycD = PPARδ | 50.0% ± 1.0% |
| mCSF1 | 0% |

A cancer biomarker panel based upon a swab in the presence of an RNA protection cocktail comprises the biomarkers COX2 and IL-8. In one aspect, a cancer biomarker panel using a swab comprises the genes listed in Table 14.

TABLE 14

| SWABS CANCER (RNA PROTECTION) | % having a change relative to control |
|---|---|
| COX2 = IL8 | 100% |
| Groγ = COX1 = CD44 | 67.0% ± 1.0% |
| OPN = cMyc = mCSF1 = cycD | 50.0% ± 1.0% |
| CXCRZ = Groα = PPARγ = P21 | 33.0% ± 1.0% |
| PPARα = PPARδ | 17.0% ± 1.0% |
| SAA1 | 0% |

In one embodiment, a method for gene expression profiling comprises measuring mRNA levels for biomarkers selected in a panel. Such a method can include the use of primers, probes, enzymes, and other reagents for the preparation, detection, and quantitation of mRNA (e.g., by PCR, by Northern blot and the like). The primers listed in SEQ ID NOs: 45-88 are particularly suited for use in gene expression profiling using RT-PCR based on a polynucleotide biomarker. Although the disclosure provides particular primers and probes, those of skill in the art will readily recognize that additional probes and primers can be generated based upon the polynucleotide sequences provided by the disclosure. Referring to the primers and probes exemplified herein, a series of primers were designed using Primer Express Software (Applied Biosystems, Foster City, Calif.). The primers listed in SEQ ID NOs: 45-88 were designed, selected, and tested accordingly. In addition to the primers, reagents such as a dinucleotide triphosphate mixture having all four dinucleotide triphosphates (e.g., dATP, dGTP, dCTP, and dTTP), a reverse transcriptase enzyme, and a thermostable DNA polymerase were used for RT-PCR. Additionally buffers, inhibitors and activators can also be used for the RT-PCR process. Once the cDNA has been sufficiently amplified to a specified end point, the cDNA sample can be prepared for detection and quantitation. Though a number of detection schemes are contemplated, as will be discussed in more detail below, one method contemplated for detection of polynucleotides is fluorescence spectroscopy, and therefore labels suited to fluorescence spectroscopy are desirable for labeling polynucleotides. One example of such a fluorescent label is SYBR Green, though numerous related fluorescent molecules are known including, without limitation, DAPI, Cy3, Cy3.5, Cy5, CyS.5, Cy7, umbelliferone, fluorescein, fluorescein isothiocyanate (FITC), rhodamine, dichlorotriazinylamine fluorescein, dansyl chloride or phycoerythrin.

In one embodiment of the disclosure, an oligonucleotide probe comprises a fragment of c-myc, CD44 antigen ("CD44"), cyclooxygenase 1 and 2 ("COX-1" and "COX-2"), cyclin D1, cyclin-dependent kinase inhibitor ("p21$^{cip/waf1}$") interleukin 8 ("IL-8"), interleukin 8 receptor ("CXCR2"), osteopontin ("OPN"), melanoma growth stimulatory activity ("Groα/MGSA"), GRO3 oncogene ("Groγ"), macrophage colony stimulating factor 1 ("MCSF-1"), peroxisome proliferative activated receptor, alpha, delta and gamma ("PPAR-α, Δ and γ") and serum amyloid A1 ("SM 1") as set forth in Table 1.

Oligonucleotide probes and primers useful in the methods of the disclosure comprise at least 8 nucleotides of SEQ ID NOs:1, 3, 5, 7, 9, 11, 13, 15, 17, 19, 21, 23, 25, 27, 29, 31, 33, 35, 37, 39, 41, or 43 (including an oligonucleotide wherein T can be U) wherein the oligonucleotide specifically hybridizes to a polynucleotide sample from a subject comprising SEQ ID NO: 1, 3, 5, 7, 9, 11, 13, 15, 17, 19, 21, 23, 25, 27, 29, 31, 33, 35, 37, 39, 41 and/or 43.

Any of the oligonucleotide primers and probes of the disclosure can be immobilized on a solid support. Solid supports are known to those skilled in the art and include the walls of wells of a reaction tray, test tubes, polystyrene beads, magnetic beads, nitrocellulose strips, membranes, microparticles such as latex particles, glass and the like. The solid support is not critical and can be selected by one skilled in the art. Thus, latex particles, microparticles, magnetic or non-magnetic beads, membranes, plastic tubes, walls of microtiter wells, glass or silicon chips and the like are all suitable examples. Suitable methods for immobilizing oligonucleotides on a solid phase include ionic, hydrophobic, covalent interactions and the like. The solid support can be chosen for its intrinsic ability to attract and immobilize the capture reagent. The oligonucleotide probes or primers of the disclosure can be attached to or immobilized on a solid support individually or in groups of about 2-10,000 distinct oligonucleotides of the disclosure to a single solid support.

A substrate comprising a plurality of oligonucleotide primers or probes of the disclosure may be used either for detecting or amplifying targeted sequences. The oligonucleotide probes and primers of the disclosure can be attached in contiguous regions or at random locations on the solid support. Alternatively the oligonucleotides of the disclosure may be attached in an ordered array wherein each oligonucleotide is attached to a distinct region of the solid support which does not overlap with the attachment site of any other oligonucleotide. Typically, such oligonucleotide arrays are "addressable" such that distinct locations are recorded and can be accessed as part of an assay procedure. The knowledge of the location of oligonucleotides on an array make "addressable" arrays useful in hybridization assays. For example, the oligonucleotide probes can be used in an oligonucleotide chip such as those marketed by Affymetrix and described in U.S. Pat. No. 5,143,854; PCT publications WO 90/15070 and 92/10092, the disclosures of which are incorporated herein by reference. These arrays can be produced using mechanical synthesis methods or light directed synthesis methods which incorporate a combination of photolithographic methods and solid phase oligonucleotide synthesis.

The immobilization of arrays of oligonucleotides on solid supports has been rendered possible by the development of a technology generally referred to as "Very Large Scale Immobilized Polymer Synthesis" in which probes are immobilized in a high density array on a solid surface of a chip (see, e.g., U.S. Pat. Nos. 5,143,854; and 5,412,087 and in PCT Publications WO 90/15070, WO 92/10092 and WO 95/11995, each of which are incorporated herein by reference), which describe methods for forming oligonucleotide arrays through techniques such as light-directed synthesis techniques.

In another aspect, an array of oligonucleotides complementary to subsequences of the target gene is used to determine the identity of the target, measure its amount, and detect differences between the target and a reference wild-type sequence.

Hybridization techniques can also be used to identify the biomarkers and/or polymorphisms of the disclosure and thereby determine or predict a colorectal cancer or gastrointestinal inflammatory disease or disorder. In this aspect, expression profiles or polymorphism(s) are identified based upon the higher thermal stability of a perfectly matched probe compared to the mismatched probe. The hybridization reactions may be carried out in a solid support (e.g., membrane or chip) format, in which, for example, the target nucleic acids are immobilized on nitrocellulose or nylon membranes and probed with oligonucleotide probes of the disclosure. Any of the known hybridization formats may be used, including Southern blots, slot blots, "reverse" dot blots, solution hybridization, solid support based sandwich hybridization, bead-based, silicon chip-based and microtiter well-based hybridization formats.

Hybridization of an oligonucleotide probe to a target polynucleotide may be performed with both entities in solution, or such hybridization may be performed when either the oligonucleotide or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Oligonucleotides may be synthesized directly on the solid support or attached to the solid support subsequent to synthesis. Solid-supports suitable for use in detection methods of the disclosure include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid.

In one aspect, a sandwich hybridization assay comprises separating the variant and/or wild-type target nucleic acid biomarker in a sample using a common capture oligonucleotide immobilized on a solid support and then contact with specific probes useful for detecting the variant and wild-type nucleic acids. The oligonucleotide probes are typically tagged with a detectable label.

Hybridization assays based on oligonucleotide arrays rely on the differences in hybridization stability of short oligonucleotides to perfectly matched and mismatched target variants. Efficient access to expression or polymorphic information is obtained through a basic structure comprising high-density arrays of oligonucleotide probes attached to a solid support (the chip) at selected positions. Each DNA chip can contain thousands to millions of individual synthetic DNA probes arranged in a grid-like pattern and miniaturized to the size of a dime or smaller. Such a chip may comprise oligonucleotides representative of both a wild-type and variant sequences.

Oligonucleotides of the disclosure can be designed to specifically hybridize to a target region of a polynucleotide. As used herein, specific hybridization means the oligonucleotide forms an anti-parallel double-stranded structure with the target region under certain hybridizing conditions, while failing to form such a structure when incubated with a different target polynucleotide or another region in the polynucleotide or with a polynucleotide lacking the desired locus under the same hybridizing conditions. Typically, the oligonucleotide specifically hybridizes to the target region under conventional high stringency conditions.

A nucleic acid molecule such as an oligonucleotide or polynucleotide is said to be a "perfect" or "complete" complement of another nucleic acid molecule if every nucleotide of one of the molecules is complementary to the nucleotide at the corresponding position of the other molecule. A nucleic acid molecule is "substantially complementary" to another molecule if it hybridizes to that molecule with sufficient stability to remain in a duplex form under conventional low-stringency conditions. Conventional hybridization conditions are described, for example, in Sambrook et al., Molecular Cloning, A Laboratory Manual, 2nd ed., Cold Spring Harbor Press, Cold Spring Harbor, N.Y. (1989), and in Haymes et al., Nucleic Acid Hybridization, A Practical Approach, IRL Press, Washington, D.C. (1985). While perfectly complementary oligonucleotides are used in most assays for detecting target polynucleotides or polymorphisms, departures from complete complementarity are contemplated where such departures do not prevent the molecule from specifically hybridizing to the target region. For example, an oligonucleotide primer may have a non-complementary fragment at its 5' or 3' end, with the remainder of the primer being complementary to the target region. Those of skill in the art are familiar with parameters that affect hybridization; such as temperature, probe or primer length and composition, buffer composition and salt concentration and can readily adjust these parameters to achieve specific hybridization of a nucleic acid to a target sequence.

A variety of hybridization conditions may be used in the disclosure, including high, moderate and low stringency conditions; see for example Maniatis et al., Molecular Cloning: A Laboratory Manual, 2d Edition, 1989, and Short Protocols in Molecular Biology, ed. Ausubel, et al., hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target hybridize to the polyadenylated mRNA target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of helix destabilizing agents such as formamide. The hybridization conditions may also vary when a non-ionic backbone, i.e., PNA is used, as is known in the art. In addition, cross-linking agents may be added after target binding to cross-link, i.e., covalently attach, the two strands of the hybridization complex.

A polymorphism in a target region of a gene may be assayed before or after amplification using one of several hybridization-based methods known in the art. Typically, allele-specific oligonucleotides are utilized in performing such methods. The allele-specific oligonucleotides may be used as differently labeled probe pairs, with one member of the pair showing a perfect match to one variant of a target sequence and the other member showing a perfect match to a different variant. In some embodiments, more than one polymorphism may be detected at once using a set of allele-specific oligonucleotides or oligonucleotide pairs. Typically, the members of the set have melting temperatures within 5° C., and more typically within 2° C., of each other when hybridizing to each of the polymorphic sites being detected.

In one aspect of for detection of polymorphisms, termed 4 L tiled array, a set of four probes (A, C, G, T), typically 15-nucleotide oligomers in length is used. In each set of four probes, the perfect complement will hybridize more strongly than mismatched probes. Consequently, hybridization signals of the 15-mer probe set tiled array are perturbed by a single base change in the target sequence resulting in a characteristic loss of signal. Such techniques are particularly useful for detection of polymorphic regions in the biomarkers of the disclosure.

In another aspect, polymorphic regions of a biomarker of the disclosure may be identified. Diagnostic tests useful for detecting polymorphic regions typically belong to two types: genotyping tests and haplotyping tests. A genotyping test simply provides the status of a variance or variances in a subject. For example, suppose nucleotide 150 of hypothetical gene X on an autosomal chromosome is an adenine (A) or a guanine (G) base. The possible genotypes in an individual with the gene are AA, AG or GG at nucleotide 150 of gene X.

In a haplotyping test there is at least one additional variance in gene X, say at nucleotide 810, which varies in the population as cytosine (C) or thymine (T). Thus a particular copy of gene X may have any of the following combinations of nucleotides at positions 150 and 810: 150A-810C, 150A-810T, 150G-810C or 150G-810T. Each of the four possibilities is a unique haplotype. If the two nucleotides interact in either RNA or protein, then knowing the haplotype can be important. The point of a haplotyping test is to determine the haplotypes present in a DNA or cDNA sample (e.g. from a subject).

Methods and compositions of the disclosure are useful for diagnosing or determining the risk of developing a colorectal cancer or gastrointestinal inflammatory disease or disorder. Such tests can be performed using DNA or RNA samples collected from blood, cells, tissue scrapings or other cellular materials, and can be performed by a variety of methods including, but not limited to, hybridization with biomarker-specific probes, enzymatic mutation detection, chemical cleavage of mismatches, mass spectrometry, PCR or DNA sequencing, including minisequencing. Diagnostic tests may involve a panel of from one or more genes, genetic markers (gene expression profiles), often on a solid support, or using PCR techniques, which enables the simultaneous determination of more than one variance in one or more genes or expression of one or more genes.

A target biomarker or region(s) thereof (e.g., containing a polymorphism of interest) may be amplified using any oligonucleotide-directed amplification method including, but not limited to, polymerase chain reaction (PCR) (U.S. Pat. No. 4,965,188), ligase chain reaction (LCR) (Barany et al., Proc. Natl. Acad. Sci. USA 88:189-93 (1991); WO 90/01069), and oligonucleotide ligation assay (OLA) (Landegren et al., Science 241:1077-80 (1988)). Other known nucleic acid amplification procedures may be used to amplify the target region(s) including transcription-based amplification systems (U.S. Pat. No. 5,130,238; European Patent No. EP 329,822; U.S. Pat. No. 5,169,766; WO 89/06700) and isothermal methods (Walker et al., Proc. Natl. Acad. Sci. USA 89:392-6 (1992)).

Ligase Chain Reaction (LCR) techniques can be used and are particularly useful for detection of polymorphic variants. LCR occurs only when the oligonucleotides are correctly base-paired. The Ligase Chain Reaction (LCR), which utilizes the thermostable Taq ligase for ligation amplification, is useful for interrogating loci of a gene (e.g., comprising SEQ ID NO: 1, 3, 5, 7, 9, 11, 13, 15, 17, 19, 21, 23, 25, 27, 29, 31, 33, 35, 37, 39, 41 or 43). A method of DNA amplification similar to PCR, LCR differs from PCR because it amplifies the probe molecule rather than producing amplicon through polymerization of nucleotides. Two probes are used per each DNA strand and are ligated together to form a single probe. LCR uses both a DNA polymerase enzyme and a DNA ligase enzyme to drive the reaction. Like PCR, LCR requires a thermal cycler to drive the reaction and each cycle results in a doubling of the target nucleic acid molecule. LCR can have greater specificity than PCR. The elevated reaction temperatures permit the ligation reaction to be conducted with high stringency. Where a mismatch occurs, ligation cannot be accomplished. For example, a primer based upon a target gene or gene variant is synthesized in two fragments and annealed to the template with possible mutation at the boundary of the two primer fragments (i.e., the underlined nucleotide above would be found at the 5' or 3' end of the oligonucleotide). A ligase ligates the two primers if they match exactly to the template sequence.

In one embodiment, the two hybridization probes are designed each with a target specific portion. The first hybridization probe is designed to be substantially complementary to a first target domain of a target polynucleotide (e.g., a polynucleotide fragment) and the second hybridization probe is substantially complementary to a second target domain of a target polynucleotide (e.g., a polynucleotide fragment). In general, each target specific sequence of a hybridization probe is at least about 5 nucleotides long, with sequences of about 15 to 30 being typical and 20 being especially common. In one embodiment, the first and second target domains are directly adjacent, e.g., they have no intervening nucleotides. In this embodiment, at least a first hybridization probe is hybridized to the first target domain and a second hybridization probe is hybridized to the second target domain. If perfect complementarity exists at the junction, a ligation structure is formed such that the two probes can be ligated together to form a ligated probe. If this complementarity does not exist (due to mismatch based upon a variant), no ligation structure is formed and the probes are not ligated together to an appreciable degree. This may be done using heat cycling, to allow the ligated probe to be denatured off the target polynucleotide such that it may serve as a template for further reactions. The method may also be done using three hybridization probes or hybridization probes that are separated by one or more nucleotides, if dNTPs and a polymerase are added (this is sometimes referred to as "Genetic Bit" analysis).

Analysis of point mutations (e.g., polymorphic variants) in DNA can also be carried out by using the polymerase chain reaction (PCR) and variations thereof. Mismatches can be detected by competitive oligonucleotide priming under hybridization conditions where binding of the perfectly matched primer is favored. In the amplification refractory mutation system technique (ARMS), primers are designed to have perfect matches or mismatches with target sequences either internal or at the 3' residue (Newton et al., Nucl. Acids. Res. 17:2503-2516 (1989)). Under appropriate conditions, only the perfectly annealed oligonucleotide functions as a primer for the PCR reaction, thus providing a method of discrimination between normal and variant sequences.

Single nucleotide primer-guided extension assays can also be used, where the specific incorporation of the correct base is provided by the fidelity of a DNA polymerase. Detecting the nucleotide or nucleotide pair at a polymorphic site of interest may also be determined using a mismatch detection technique including, but not limited to, the RNase protection method using riboprobes (Winter et al., Proc. Natl. Acad. Sci. USA 82:7575 (1985); Meyers et al., Science 230:1242 (1985)) and proteins which recognize nucleotide mismatches, such as the *E. coli* mutS protein (Modrich, Ann. Rev. Genet. 25:229-53 (1991)). Alternatively, variant alleles can be identified by single strand conformation polymorphism (SSCP) analysis (Orita et al., Genomics 5:874-9 (1989); Humphries et al., in MOLECULAR DIAGNOSIS OF GENETIC DISEASES, Elles, ed., pp. 321-340, 1996) or denaturing gradient gel electrophoresis (DGGE) (Wartell et al., Nucl. Acids Res. 18:2699-706 (1990); Sheffield et al., Proc. Natl. Acad. Sci. USA 86:232-6 (1989)).

A polymerase-mediated primer extension method may also be used to identify the polymorphism(s). Several such methods have been described in the patent and scientific literature and include the "Genetic Bit Analysis" method (WO 92/15712) and the ligase/polymerase mediated genetic bit analysis (U.S. Pat. No. 5,679,524. Related methods are disclosed in WO 91/02087, WO 90/09455, WO 95/17676, and U.S. Pat. Nos. 5,302,509 and 5,945,283. Extended primers containing the complement of the polymorphism may be detected by mass spectrometry as described in U.S. Pat. No. 5,605,798. Another primer extension method is allele-specific PCR (Ruano et al., 1989, supra; Ruano et al., 1991, supra; WO 93/22456; Turki et al., J. Clin. Invest. 95:1635-41 (1995)).

Another technique, which may be used to analyze gene expression and polymorphisms, includes multicomponent integrated systems, which miniaturize and compartmentalize processes such as PCR and capillary electrophoresis reactions in a single functional device. An example of such technique is disclosed in U.S. Pat. No. 5,589,136, the disclosure of which is incorporated herein by reference in its entirety, which describes the integration of PCR amplification and capillary electrophoresis in chips.

Quantitative PCR and digital PCR can be used to measure the level of a polynucleotide in a sample. Digital Polymerase Chain Reaction (digital PCR, dPCR or dePCR) can be used to directly quantify and clonally amplify nucleic acids including DNA, cDNA or RNA. Digital PCR amplifies nucleic acids by temperature cycling of a nucleic acid molecule with a DNA polymerase. The reaction is typically carried out in the dispersed phase of an emulsion capturing each individual nucleic acid molecule present in a sample within many separate chambers or regions prior to PCR amplification. A count of chambers containing detectable levels of PCR end-product is a direct measure of the absolute nucleic acids quantity.

Quantitative polymerase chain reaction (qPCR) is a modification of the polymerase chain reaction and real-time quantitative PCR are useful for measuring the amount of DNA after each cycle of PCR by use of fluorescent markers or other detectable labels. Quantitative PCR methods use the addition of a competitor RNA (for reverse-transcriptase PCR) or DNA in serial dilutions or co-amplification of an internal control to ensure that the amplification is stopped while in the exponential growth phase.

Modifications of PCR and PCR techniques are routine in the art and there are commercially available kits useful for PCR amplification.

The detectable label may be a radioactive label or may be a luminescent, fluorescent of enzyme label. Indirect detection processes typically comprise probes covalently labeled with a hapten or ligand such as digoxigenin (DIG) or biotin. In one aspect, following the hybridization step, the target-probe duplex is detected by an antibody- or streptavidin-enzyme complex. Enzymes commonly used in DNA diagnostics are horseradish peroxidase and alkaline phosphatase. Direct detection methods include the use of fluorophor-labeled oligonucleotides, lanthanide chelate-labeled oligonucleotides or oligonucleotide-enzyme conjugates. Examples of fluorophor labels are fluorescein, rhodamine and phthalocyanine dyes.

Examples of detection modes contemplated for the disclosed methods include, but are not limited to, spectroscopic techniques, such as fluorescence and UV-Vis spectroscopy, scintillation counting, and mass spectroscopy. Complementary to these modes of detection, examples of labels for the purpose of detection and quantitation used in these methods include, but are not limited to, chromophoric labels, scintillation labels, and mass labels. The expression levels of polynucleotides and polypeptides measured using these methods may be normalized to a control established for the purpose of the targeted determination.

Label detection will be based upon the type of label used in the particular assay. Such detection methods are known in the art. For example, radioisotope detection can be performed by autoradiography, scintillation counting or phosphor imaging. For hapten or biotin labels, detection is with an antibody or streptavidin bound to a reporter enzyme such as horseradish peroxidase or alkaline phosphatase, which is then detected by enzymatic means. For fluorophor or lanthanide-chelate labels, fluorescent signals may be measured with spectrofluorimeters with or without time-resolved mode or using automated microtitre plate readers. With enzyme labels, detection is by color or dye deposition (p-nitropheny phosphate or 5-bromo-4-chloro-3-indolyl phosphate/nitroblue tetrazolium for alkaline phosphatase and 3,3'-diaminobenzidine-$NiCl_2$ for horseradish peroxidase), fluorescence (e.g., 4-methyl umbelliferyl phosphate for alkaline phosphatase) or chemiluminescence (the alkaline phosphatase dioxetane substrates LumiPhos 530 from Lumigen Inc., Detroit Mich. or AMPPD and CSPD from Tropix, Inc.). Chemiluminescent detection may be carried out with X-ray or polaroid film or by using single photon counting luminometers.

In another aspect of this disclosure, expression levels of proteins comprising SEQ ID NO: 2, 4, 6, 8, 10, 12, 14, 16, 18, 20, 22, 24, 26, 28, 30, 32, 34, 36, 38, 40, 42 and/or 44 can be measured and quantitated using techniques known in the art including, for example, Western blots, ELISA assays and the like. The term "polypeptide" or "polypeptides" is used interchangeably with the term "protein" or "proteins" herein.

In another embodiment, a method for protein expression profiling comprises using one or more (e.g., a plurality of) antibodies to one or more biomarkers for measuring targeted polypeptide levels from a biological sample. In one embodiment contemplated for the method, the antibodies for the panel are bound to a solid support. The method for protein expression profiling may use a second antibody having specificity to some portion of the bound polypeptide. Such a second antibody may be detectably labeled with molecules useful for detection and quantitation of the bound polypeptides. Additionally, other reagents are contemplated for detection and quantitation including, for example, small molecules such as cofactors, substrates, complexing agents, and the like, or large molecules, such as lectins, peptides, olionucleotides, and the like. Such moieties may be either naturally occurring or synthetic.

The disclosure further contemplates, antibodies capable of specifically binding to a biomarker polypeptides encoded in proper frame, based upon transcriptional and translational starts, of the above-identified polynucleotide biomarker sequences (e.g., comprising SEQ ID NOs: 1, 3, 5, 7, 9, 11, 13, 15, 17, 19, 21, 23, 25, 27, 29, 31, 33, 35, 37, 39, 41, or 43). The disclosure thus includes isolated, purified, and recombinant polypeptides comprising a contiguous span of at least 4 amino acids, typically at least 6, more commonly at least 8 to 10 amino acids encoded by a polynucleotide comprising SEQ ID NOs: 1, 3, 5, 7, 9, 11, 13, 15, 17, 19, 21, 23, 25, 27, 29, 31, 33, 37, 39, 41, or 43.

The disclosure also contemplates the use of immunoassay techniques for measurement of polypeptide biomarkers identified herein. The polypeptide biomarker can be isolated and used to prepare antisera and monoclonal antibodies that specifically detect a biomarker gene product. Mutated gene products also can be used to immunize animals for the production of polyclonal antibodies. Recombinantly produced peptides can also be used to generate antibodies. For example, a recombinantly produced fragment of a polypeptide can be injected into a mouse along with an adjuvant so as to generate an immune response. Murine immunoglobulins which bind the recombinant fragment with a binding affinity of at least $1\times10^7 M^{-1}$ can be harvested from the immunized mouse as an antiserum, and may be further purified by affinity chromatography or other means. Additionally, spleen cells are harvested from the mouse and fused to myeloma cells to produce a bank of antibody-secreting hybridoma cells. The bank of hybridomas can be screened for clones that secrete immunoglobulins which bind the recombinantly produced fragment with an affinity of at least $1\times10^6 M^{-1}$. More specifically, immunoglobulins that selectively bind to the variant polypeptides but poorly or not at all to wild-type polypeptides are selected, either by pre-absorption with wild-type proteins or by screening of hybridoma cell lines for specific idiotypes that bind the variant, but not wild-type, polypeptides.

Polynucleotides capable of expressing the polypeptides can be generated using techniques skilled in the art based upon the identified sequences herein. Such polynucleotides can be expressed in hosts, wherein the polynucleotide is operably linked to (i.e., positioned to ensure the functioning of) an expression control sequence. Expression vectors are typically replicable in the host organisms either as episomes or as an integral part of the host chromosome. Expression vectors can contain selection markers (e.g., markers based on tetracyclin resistance or hygromycin resistance) to permit detection and/or selection of those cells transformed with the desired polynucleotide.

Polynucleotides encoding a variant polypeptide may include sequences that facilitate transcription and translation of the coding sequences such that the encoded polypeptide product is produced. Construction of such polynucleotides is known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

Prokaryotes can be used as host cells for the expression of a variant polypeptides, such techniques are known in the art. Other microbes, such as yeast, may also be used for expression. In addition to microorganisms, mammalian tissue cell culture may also be used to express and produce polypeptides of the disclosure. Eukaryotic cells useful in the methods of the disclosure include the CHO cell lines, various COS cell lines, HeLa cells, myeloma cell lines, Jurkat cells, and so forth. Expression vectors for these cells can include expression control sequences, such as an origin of replication, a promoter, an enhancer, an necessary information processing sites, such as ribosome binding sites, RNA splice sites, polyadenylation sites, and transcriptional terminator sequences.

The techniques for polynucleotide cloning and expression are useful in the disclosure for the generation of probes capable of hybridizing to polynucleotide biomarkers or the generation of antibodies useful for binding polypeptide biomarkers of the disclosure.

In further methods, peptides, drugs, fatty acids, lipoproteins, or small molecules which interact with a biomarker (e.g., a polynucleotide or polypeptide, protein, or a fragment comprising a contiguous span of at least 4 amino acids, at least 6 amino acids, or typically at least 8 to 10 amino acids or more of sequences corresponding to the biomarkers herein) can be used as detection agents for measuring biomarkers. The molecule to be tested for binding is labeled with a detectable label, such as a fluorescent, radioactive, or enzymatic tag. After removal of non-specifically bound molecules, bound molecules are detected using appropriate means.

These results, with reference to the figures and specific examples below, demonstrate that it is possible to sample cells through a minimally invasive swabbing collection method from an area distant from a cancerous lesion, but capable of indicating a non-normal colon condition. In that regard, samples taken either minimally invasively or non-invasively would render samples that could be analyzed using the disclosed panel of biomarkers. Such non-invasive procedures not only reduce the cost of determination of CRC, but reduce the discomfort and risk associated with current methodology. All these factors together increase the attractiveness of regular testing, and hence patient compliance. Increased patient compliance, coupled with an effective determination for CRC, enhance the prospects for early detection, and enhanced survival rates.

Table 15 below demonstrates the differences in expression profiles based upon biomarkers of the disclosure. FHSH refers to family and self history of the subject. FHSH subjects lacked a history of polyps. In addition, FHSH subject can lack a history of gastrointestinal diseases or disorders. As referenced in table 15, “Others” refer to subjects that have a history of gastrointestinal diseases or disorders. Accordingly, in one aspect of the disclosure, a predictive biomarker for gastrointestinal inflammatory disease or disorder would include detecting a change in expression of IL-8, CD44, c-myc, and/or P21, which all show larger changes (e.g., about 19, 63, 50 and 56%, respectively, relative to controls). It is important to note that a change in expression of a biomarker of the disclosure need not necessarily be an increase in expression relative to a control. Rather, a change can be an increase or decrease relative to a control so long as the change represents a statistically significant difference relative to the control. In one aspect, the change is at least 10%, 15%, 20%, 25%, 30%, 35%, 40%, 45%, 50%, 55%, 60%, 65%, 70%, 75% or more in an increase or decrease relative to a control. Where a panel of biomarkers are used in the detection of a disease or disorder, a smaller change relative to a control can be indicative of the disease or disorder or risk thereof in comparison to a change in each biomarker alone. A statistician of skill in the art will be capable of identifying statistically significant differences in a biomarker or panel of biomarkers relative to a control value(s).

In principle, the larger the number of genes used, the more sensitive the analysis is will be. The panel can comprise from 3 to fifteen or sixteen genes or biomarkers. In one aspect, the panel comprises 15 or 16 genes or biomarkers. However, for individuals with polyps or with history of cancer, the specificity is somewhat less, and fine-tuning the analysis by adding to or otherwise modifying the gene panel increases specificity. As discussed below, the procedure involves determining which genes in the panel make the largest contribution to significance.

Using the methods described herein, research on APCmin mice, identified a panel of mRNAs with highly up-regulated activities associated with colorectal cancer. Similar genes were seen upregulated in human samples. While the pathologist would describe the staging of the cancer in terms of depth of invasion and the presence or absence of lymph node involvement, among other variable, with the usual comment that the margins were clear, gene expression data demonstrated that the margins showed highly up-regulated mRNAs, and these values were high all over the entire specimen, not just adjacent to the cancer itself. Case after case of such resected colon cancer specimens showed the identical data. The panel of 16 selected mRNAs comprised of many different metabolic pathways resulted in a new panel useful for diagnostics.

These same mRNAs showed minimal activity in colons with no polyp or cancer. These patients were males and females, Caucasians and Asians and the results were the same, very low values with normal colons.

In patients with colon cancers and in many patients with pre-malignant polyps, these values were high not only in the region of the cancer or the polyp, but also far away from these lesions, as far away as the rectum. The rectal biopsy values were as abnormal even when the lesion was in the ascending colon or cecum.

Ninety patients were examined to demonstrate the methods and compositions of the disclosure. Although the activities of the panel of 16 genes may vary slightly between the two samples, they essentially yield the same results. This is probably due to the slight difference in the cells so collected, with the biopsy samples being deeper into the rectal mucosa and the smear samples coming entirely from the surface of the rectal lining. Thus, a simple rectal smear through an ordinary anoscope, without bowel preparation, will give a glimpse of what the rest of the colon looks like. Cancer cases had extremely high values. The data strongly support that a highly up-regulated mRNA activity in a selected panel of the disclosure from a simple rectal smear correlates with a colorectal cancer anywhere in the colon.

In one of the study population 52% were males and 48% females. 43% were Caucasians, 52% were Asians and 4% were African American. For the patients with a positive family history of colorectal cancer, some showed elevated activities and some did not. For the patients with polyps, some showed elevated activities, particularly those with significant polyps 2 cm or larger or with villous component. Most of the patients with hyperplastic polyps showed normal activities, although a few had abnormal values. Interestingly enough, for patients who simply had intermittently rectal bleeding without any risk factors, some showed abnormal levels and some did not. Those patients with no polyp or cancer and with no risk factors had very low values. Lastly, there were three patients with very high values without a polyp or a cancer. One had Crohns' disease involving the sigmoid colon and two had Barrett's esophagus.

In another aspect, the disclosure provides methods of early detection or diagnosis of a colorectal cancer or gastrointestinal inflammatory disease or disorder based upon measurement of any of the biomarkers in tables 3-14 by rectal, colon, or buccal swabs. This method can be followed by a determination at a later time by measuring the same, one or more additional genes, or one or more additional biomarker panels. For example, early detection or diagnosis can be based upon screening changes in any one or more of the biomarkers described, wherein a change in a biomarker's expression (e.g., IL-8, P21, c-myc, and/or CD44) relative to a control is indicative of a gastrointestinal inflammatory disease or disorder or the risk of acquiring an gastrointestinal inflammatory disease or disorder; following initial diagnosis or prediction the same or different makers (e.g., IL-8) can be measured to determine the prognosis or development of a disease. The data below indicate, for example, that the biomarker IL-8 and OPN may be indicative of later stage development of a gastrointestinal disease or disorder.

TABLE 15

| Overall | Swabs FHSH, n = 16 $p < 0.0000$ | Swabs Others, n = 9 $p < 0.0000$ | Biopsies FHSH, n = 17 $p < 0.0001$ | Biopsies Others, n = 8 $p < 0.0001$ |
|---|---|---|---|---|
| CXCR2 | 19% | 56% | 57% | 38% |
| OPN | 38 | 44 | 18 | 63 |
| COX1 | 42 | 33 | 18 | 13 |
| PPARα | 15 | 22 | 12 | 13 |
| COX2 | 38 | 44 | 12 | 13 |
| Groα | 50 | 56 | 29 | 25 |
| Groγ | 42 | 56 | 17 | 25 |
| IL8 | 23 | 67 | 12 | 13 |
| PPARγ | 31 | 33 | 17 | 25 |
| P21 | 31 | 78 | 12 | 25 |
| CMyC | 38 | 56 | 29 | 13 |
| CD44 | 46 | 67 | 17 | 13 |
| mCSF-1 | 35 | 33 | 0 | 0 |
| cycD | 31 | 44 | 12 | 0 |
| PPARδ | 31 | 56 | 24 | 50 |
| SAA1 | 27 | 22 | 12 | 25 |

In other embodiments, the computer-readable medium for determine a risk, prognosis or diagnosis of a gastrointestinal disorder or disease (e.g., an IBD, polyp or cancer) comprises instructions to apply a statistical process to a data set comprising a biomarker profile optionally in combination with a symptom profile provided by a technician, nurse or physician, which indicates the presence or severity of at least one symptom in the individual to produce a statistically derived decision classifying the sample as a (i) non-colorectal cancer gastrointestinal disease or disorder; (ii) a polyp stage disease or disorder or (iii) a colorectal cancer stage disease or disorder, based upon the biomarker profile or the biomarker profile and the symptom profile.

In another embodiment, a computer-readable medium including code for controlling one or more processors to classify whether a sample from an individual is associated (i) non-colorectal cancer gastrointestinal disease or disorder; (ii) a polyp stage disease or disorder or (iii) a colorectal cancer stage disease or disorder comprising: (a) instructions to apply a first statistical process to a data set comprising a biomarker profile to produce a statistically derived decision classifying the sample as (i) non-colorectal cancer gastrointestinal disease or disorder; (ii) a polyp stage disease or disorder or (iii) a colorectal cancer stage disease or disorder based upon the biomarker profile; and if the sample is classified as a (i) non-colorectal cancer gastrointestinal disease or disorder; (ii) a polyp stage disease or disorder or (iii) a colorectal cancer stage disease or disorder, (b) instructions to apply a second statistical process to the same or different data set to produce a second statistically derived decision classifying the (i) non-colorectal cancer gastrointestinal disease or disorder; (ii) a polyp stage disease or disorder or (iii) a colorectal cancer stage disease or disorder.

In another embodiment, a process can use a computer to apply a second statistic approach to a biomarker panel measurement based upon a earlier determine criteria (e.g., if a polyp diagnosis, then apply colorectal biomarker panel measurements and statistics; if a FHSH disposition then apply polyp biomarker panel measurements and statistics).

In yet another embodiment, the methods and systems of the disclosure provide for classifying whether a sample from an individual is associated with (i) non-colorectal cancer gastrointestinal disease or disorder; (ii) a polyp stage disease or disorder or (iii) a colorectal cancer stage disease or disorder, the system comprising: (a) a data acquisition module configured to produce a data set comprising a biomarker profile, wherein the biomarker profile indicates the presence or level of at least one biomarker in the sample; (b) a data processing module configured to process the data set by applying a statistical process to the data set to produce a statistically derived decision classifying the sample as an (i) non-colorectal cancer gastrointestinal disease or disorder; (ii) a polyp stage disease or disorder or (iii) a colorectal cancer stage disease or disorder sample based upon the diagnostic marker profile; and (c) a display module configured to display the statistically derived decision.

In certain instances, the statistical algorithm is a learning statistical classifier system. The learning statistical classifier system can be selected from the group consisting of a random forest (RF), classification and regression tree (C&RT), boosted tree, neural network (NN), support vector machine (SVM), general chi-squared automatic interaction detector model, interactive tree, multiadaptive regression spline, machine learning classifier, and combinations thereof. Preferably, the learning statistical classifier system is a tree-based statistical algorithm (e.g., RF, C&RT, etc.) and/or a NN (e.g., artificial NN, etc.).

In certain instances, the statistical algorithm is a single learning statistical classifier system. Typically, the single learning statistical classifier system comprises a tree-based statistical algorithm such as a RF or C&RT. As a non-limiting example, a single learning statistical classifier system can be used to classify the sample as an (i) non-colorectal cancer gastrointestinal disease or disorder; (ii) a polyp stage disease or disorder or (iii) a colorectal cancer stage disease or disorder based upon a prediction or probability value and the presence or level of at least one biomarker (or panel of biomarkers), alone or in combination with the presence or severity of at least one symptom (i.e., symptom profile). The use of a single learning statistical classifier system typically classifies the sample as an (i) non-colorectal cancer gastrointestinal disease or disorder; (ii) a polyp stage disease or disorder or (iii) a colorectal cancer stage disease or disorder with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In some instances, the data obtained from using the learning statistical classifier system or systems can be processed using a processing algorithm. Such a processing algorithm can be selected, for example, from the group consisting of a multilayer perceptron, backpropagation network, and Levenberg-Marquardt algorithm. In other instances, a combination of such processing algorithms can be used, such as in a parallel or serial fashion.

In a further embodiment, the methods of the disclosure further comprise sending the (i) non-colorectal cancer gastrointestinal disease or disorder; (ii) a polyp stage disease or disorder or (iii) a colorectal cancer stage disease or disorder classification results to a clinician, e.g., a gastroenterologist or a general practitioner. In another embodiment, the methods provides a diagnosis or prognosis in the form of a probability that the individual has (i) non-colorectal cancer gastrointestinal disease or disorder; (ii) a polyp stage disease or disorder or (iii) a colorectal cancer stage disease or disorder. For example, the individual can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having (i) non-colorectal cancer gastrointestinal disease or disorder; (ii) a polyp stage disease or disorder or (iii) a colorectal cancer stage disease or disorder.

In another embodiment, a method of the disclosure provides a method for classifying whether a sample from an individual is associated with (i) a polyp stage disease or disorder comprising: (a) determining a biomarker profile by detecting the presence or level of at least one biomarker in the sample associated with polyps; (b) classifying the sample as a polyp sample using a first statistical algorithm based upon the biomarker profile; and if the sample is classified as a polyp sample, (c) classifying the polyp sample as an polyp or colorectal cancer stage sample using a second statistical algorithm based upon a biomarker profile by detecting the presence or level of at least one biomarker in the sample associated with colorectal cancer (e.g., by swab or biopsy) and classifying the sample as a colorectal cancer sample suing a second statistical algorithm based upon a colorectal cancer biomarker panel.

One skilled in the art will appreciate that the presence or level of a plurality of biomarkers can be determined simultaneously or sequentially, using, for example, an aliquot or dilution of the individual's sample. As described above, the level of a particular biomarker in the individual's sample is generally considered to be elevated when it is at least about 25%, 50%, 75%, 100%, 125%, 150%, 175%, 200%, 250%, 300%, 350%, 400%, 450%, 500%, 600%, 700%, 800%, 900%, or 1000% greater than the level of the same marker in a comparative sample or population of samples (e.g., greater than a median level). Similarly, the level of a particular diagnostic marker in the individual's sample is typically considered to be lowered when it is at least about 5%, 10%, 15%, 20%, 25%, 30%, 35%, 40%, 45%, 50%, 55%, 60%, 65%, 70%, 75%, 80%, 85%, 90%, or 95% less than the level of the same marker in a comparative sample or population of samples (e.g., less than a median level).

Methods and kits for the polynucleotide and polypeptide expression profiling for the panel of molecular markers are also contemplated as part of the present disclosure.

In one embodiment, a kit for gene expression profiling comprises the reagents and instructions necessary for the gene expression profiling of the biomarkers or biomarker panel. Thus, for example, the reagents may include primers, enzymes, and other reagents for the preparation, detection, and quantitation of cDNAs for the claimed panel of biomarkers. The primers listed in SEQ ID NOs: 45-88 are particularly suited for use in gene expression profiling using RT-PCR based on the claimed panel. The primers listed in SEQ ID NOs: 45-88 were specifically designed, selected, and tested accordingly. In addition to the primers, reagents such as dinucleotide triphosphate comprising dinucleotide triphosphates (e.g., dATP, dGTP, dCTP, and dTTP), reverse transcriptase, and a thermostable DNA polymerase. Additionally buffers, inhibitors and activators used for the RT-PCR process are suitable reagents for inclusion in the kit embodiment. Once the cDNA has been sufficiently amplified to a specified end point, the cDNA sample must be prepared for detection and quantitation. One method contemplated for detection of polynucleotides is fluorescence spectroscopy using fluorescent moieties or labels that are suited to fluorescence spectroscopy are desirable for labeling polynucleotides and may also be included in reagents of the kit embodiment.

In one embodiment, the disclosure provides a kit useful for identifying biomarkers indicative of a gastrointestinal disease or disorder. For example, the kit of the disclosure can comprise one or more oligonucleotides designed for identifying alleles and/or biomarkers of the disclosure. In another embodiment, the kit further comprises a manual with instructions for (a) performing one or more reactions on a human nucleic acid sample to identify biomarkers and/or alleles present in the subject.

The oligonucleotides in a kit of the disclosure may also be immobilized on or synthesized on a solid surface such as a microchip, bead, or glass slide (see, e.g., WO 98/20020 and WO 98/20019). Such immobilized oligonucleotides may be used in a variety of detection assays, including but not limited to, probe hybridization and polymerase extension assays. Immobilized oligonucleotides useful in practicing the disclosure may comprise an ordered array of oligonucleotides designed to rapidly screen a nucleic acid sample.

Kits of the disclosure may also contain other components such as hybridization buffer (e.g., where the oligonucleotide probes) or dideoxynucleotide triphosphates (ddNTPs; e.g., for primer extension). In one embodiment, the set of oligonucleotides consists of primer-extension oligonucleotides. The kit may also contain a polymerase and a reaction buffer optimized for primer-extension mediated by the polymerase. Kits may also include detection reagents, such as biotin- or fluorescent-tagged oligonucleotides or ddNTPs and/or an enzyme-labeled antibody and one or more substrates that generate a detectable signal when acted on by the enzyme. It is also contemplated that the above described methods and compositions of the disclosure may be utilized in combination with other biomarker techniques.

Nucleic acid samples, for example for use in variance identification, can be obtained from a variety of sources as known to those skilled in the art, or can be obtained from genomic or cDNA sources by known methods.

In another embodiment, a kit for protein expression profiling comprises the reagents and instructions necessary for protein expression profiling of a polypeptide biomarker panel. Thus, in this embodiment, the kit for protein expression profiling includes supplying an antibody panel based on a panel of biomarkers for measuring targeted polypeptide levels from a biological sample. One embodiment contemplated for such a panel includes the antibody panel bound to a solid support. Additionally, the reagents included with the kit for protein expression profiling may use a second antibody having specificity to some portion of the bound polypeptide.

Such a second antibody may be labeled with molecules useful for detection and quantitation of the bound polypeptides.

Generally, the diagnostic test of the disclosure involves determining whether an individual has a variance or variant form of a gene or a change in expression.

Integrated systems can be envisaged mainly when microfluidic systems are used. These systems comprise a pattern of microchannels designed onto a glass, silicon, quartz, or plastic wafer included on a microchip. The movements of the samples are controlled by electric, electroosmotic or hydrostatic forces applied across different areas of the microchip. The microfluidic system may integrate nucleic acid amplification, microsequencing, capillary electrophoresis and a detection method such as laser-induced fluorescence detection.

It is also contemplated that the gene expression profile may be transmitted to a remote location for analysis. For example, changes in a detectable signal related to gene expression from a first time and a second time are communicated to a remote location for analysis.

The digital representation of the detectable signal is transmittable over any number of media. For example, such digital data can be transmitted over the Internet in encrypted or in publicly available form. The data can be transmitted over phone lines, fiber optic cables or various air-wave frequencies. The data are then analyzed by a central processing unit at a remote site, and/or archived for compilation of a data set that could be mined to determine, for example, changes with respect to historical mean "normal" values of a genetic expression profile of a subject.

Embodiments of the disclosure include systems (e.g., internet based systems) particularly computer systems which store and manipulate the data corresponding to the detectable signal obtained an expression profile. As used herein, "a computer system" refers to the hardware components, software components, and data storage components used to analyze the digital representative of an expression profile or plurality of profiles. The computer system typically includes a processor for processing, accessing and manipulating the data. The processor can be any well-known type of central processing unit.

Typically the computer system is a general purpose system that comprises the processor and one or more internal data storage components for storing data, and one or more data retrieving devices for retrieving the data stored on the data storage components. A skilled artisan can readily appreciate that any one of the currently available computer systems are suitable.

In one particular embodiment, the computer system includes a processor connected to a bus which is connected to a main memory (preferably implemented as RAM) and one or more internal data storage devices, such as a hard drive and/or other computer readable media having data recorded thereon. In some embodiments, the computer system further includes one or more data retrieving device for reading the data stored on the internal data storage devices.

The data retrieving device may represent, for example, a floppy disk drive, a compact disk drive, a magnetic tape drive, or a modem capable of connection to a remote data storage system (e.g., via the internet) and the like. In some embodiments, the internal data storage device is a removable computer readable medium such as a floppy disk, a compact disk, a magnetic tape, and the like, containing control logic and/or data recorded thereon. The computer system may advantageously include or be programmed by appropriate software for reading the control logic and/or the data from the data storage component once inserted in the data retrieving device.

EXAMPLES

The genes in the expression panel fall into four major groups: 1) APC/b-catenin pathway, including c-myc, cyclin D1, and proliferating peroxisome activating receptor (PPAR alpha, delta and gamma); 2) NF-kB/inflammation pathway, including the growth-related oncogenes (Gro)-alpha and gamma osteopontin (OPN), and colony-stimulating factor (M-CSF-1), cyclo-oxygenases (COX)-1 and 2, interleukin-8 (IL-8), and the cytokine receptor CXCR2; 3) cell cycle/transcription factors, including p21, cyclin D1, c-myc, PPAR alpha, delta and gamma and 4) cell communication signals, including IL-8, PPAR alpha, delta and gamma, CXCR2, CD44, and OPN. Most of these genes are shown to be up-regulated in human colon cancers, though a few, such as the p21, as well as PPAR alpha, delta and gamma are down-regulated.

The disclosure also provides information comparing rectal swabs vs. biopsies as a means of tissue collection, in about 90 individuals, 37 individuals with history, 25 individuals with polyps (with or without history), and 23 controls with no polyps, no family or self history of cancer, and no known obvious upper GI problems. In this 90 patient study there was no cancer in situ case, 5 individuals scheduled for surgery due to colon cancer were swabbed.

The methods compare gene expression values of normal appearing mucosa of individuals or a group with cancer or cancer risk with values from controls. The statistical approach generally begins with a global multivariate analysis of variance (ANOVA), that takes into account correlations among the expression levels of different genes. This type of analysis controls the false positive rate by providing a single test of whether the expression patterns, based on all the genes in the subset, differ between groups or individuals. If the global test is significant for a particular individual or for a particular group, a univariate test was then used to determine which genes are contributing to the global difference.

This was supplemented by an analysis based on Mahalanobis-distance (M-dist). M-dist is a multivariate measure of the distance between a single gene expression value from a patient and the mean of a pool of samples from controls. M-dist is expected to have a chi-square distribution with degrees of freedom equal to the number of genes. An arbitrary cut-off point, such as the 95th percentile, is chosen, below which most individual control values will fall. Thus an experimental subject with an M-dist sample value above this criterion can be thought of as being significantly different from a control sample.

M-dist values can be determined for either each individual biopsy or swab removed from an individual, or for the mean of gene expression values from all samples taken from an individual. These M-dist values can then be plotted on a graph, with the value from each sample or each individual represented by a single point. The sensitivity and specificity of the approach can be readily visualized from these plots. The sensitivity is the proportion of values in the experimental group that are above the 95th percentile—represented as a horizontal line on the graph—while the specificity is the proportion of all values above the line which belong to individuals in the experimental group.

Biopsies of colonic mucosa, from rectosigmoid or rectal areas, were taken from subjects during the course of colonoscopy. The subjects included individuals with adenomatous polyps, the precursor of most colon cancers; individuals with a family history or self history of cancer; and individuals with no polyps or family/self history, who served as normal controls. In all cases, the biopsies were composed of normal appearing mucosa.

In addition, mucosal samples were obtained from individuals in all these groups by a rectal smear, using a small anoscope. A small brush was inserted through the anoscope several centimeters into rectum, and cells removed by gentle scraping.

Total RNA was extracted from each tissue sample, and reverse transcriptase used to convert RNA to cDNA. The expression of each of fifteen genes was then determined using PCR, with primers designed to amplify each gene.

Mahalanobis (M-dist) was selected as the measure of statistical significance because it summarizes in a single number the differences between a pattern of gene expression for any individual against the average of a pool of individuals, taking into account variability of each gene's expression and correlations among pairs of genes. This allowed us to determine on a probability scale, how different one gene expression pattern is from another. First, for each control biopsy, The M-dist was calculated from the multivariate mean of the other normal control biopsies. Then an M-dist was computed for each biopsy from each individual with polyps, family/self history of cancer, in which M-dist measured the individual's multivariate distance (i.e., difference in pattern of expression) from the pooled mean of the normal control samples. Using this approach, one can determine an upper bound for the normal controls, at any arbitrary level of significance, such as the 95th percentile. This allows analysis of significance of gene expression values of any individual experimental patient compared with the pool of normal controls.

FIG. 1 shows the Mahalanobis distance for biopsy samples, taken from (left to right), controls, resected colon cancer, individuals with family history, and individuals with polyps. Each circle represents the M-distance of a single tissue sample, and all the circles in a single vertical line represent samples from a single individual. The horizontal line represents an M-dist corresponding to the 95th percentile for normal controls, so that any values above this line are significantly different from the pooled normal control values at a significance level of $p<0.05$ (i.e. result is not like that for normal controls).

As expected, most of the samples from control individuals (99/104) fell below the 95th percentile. Four out of seventeen individuals had at least one sample above the line, and just one 1/17 had two samples. In contrast, all biopsy samples from resected colon cancer tissue had M-dist values above the 95th percentile, and for 6/7 individuals, each value was far above the line ($p<0.001$). For individuals with family history and individuals with polyps, some samples were above the 95th percentile and some below it, but all 13 individuals with family history had at least one sample above the line, as did 21/24 (87.5%) individuals with polyps. Ten of thirteen (77%) individuals with family history had more than one biopsy with an M-dist value above the line, while 14/24 (58%) individuals with polyps did.

Figure 1B:
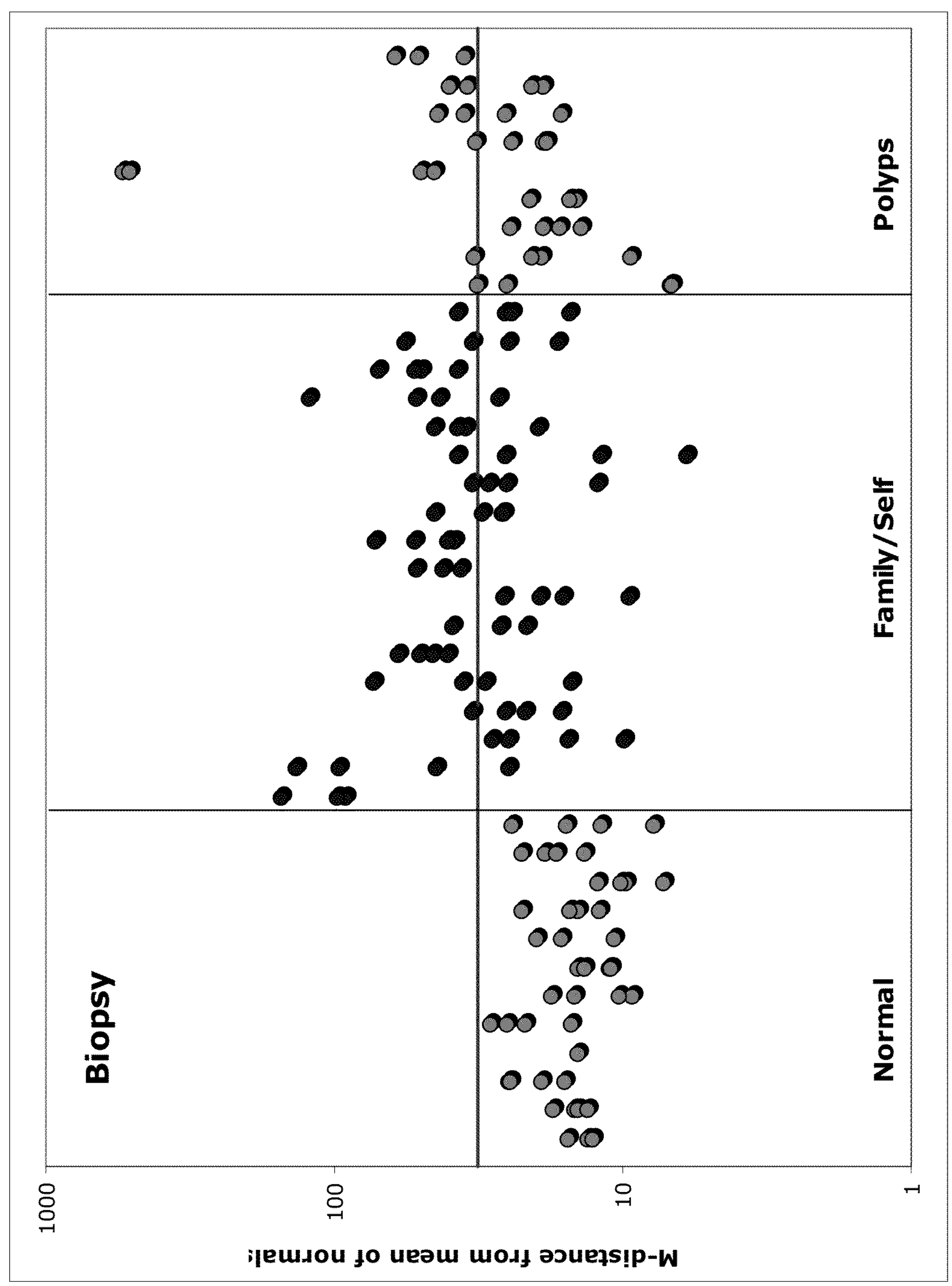

FIG. 1B shows analysis carried out on a second patient pool, one including individuals with no polyps or family/self history (Control), individuals with family history, individuals with polyps. The results are similar to those of the earlier study. All of the control biopsies had M-dist values below the 95th percentile. Fifteen of eighteen (83%) individuals with family history had at least one value above this percentile, while 4/9 (44%) individuals with polyps did.

Figure 1C:
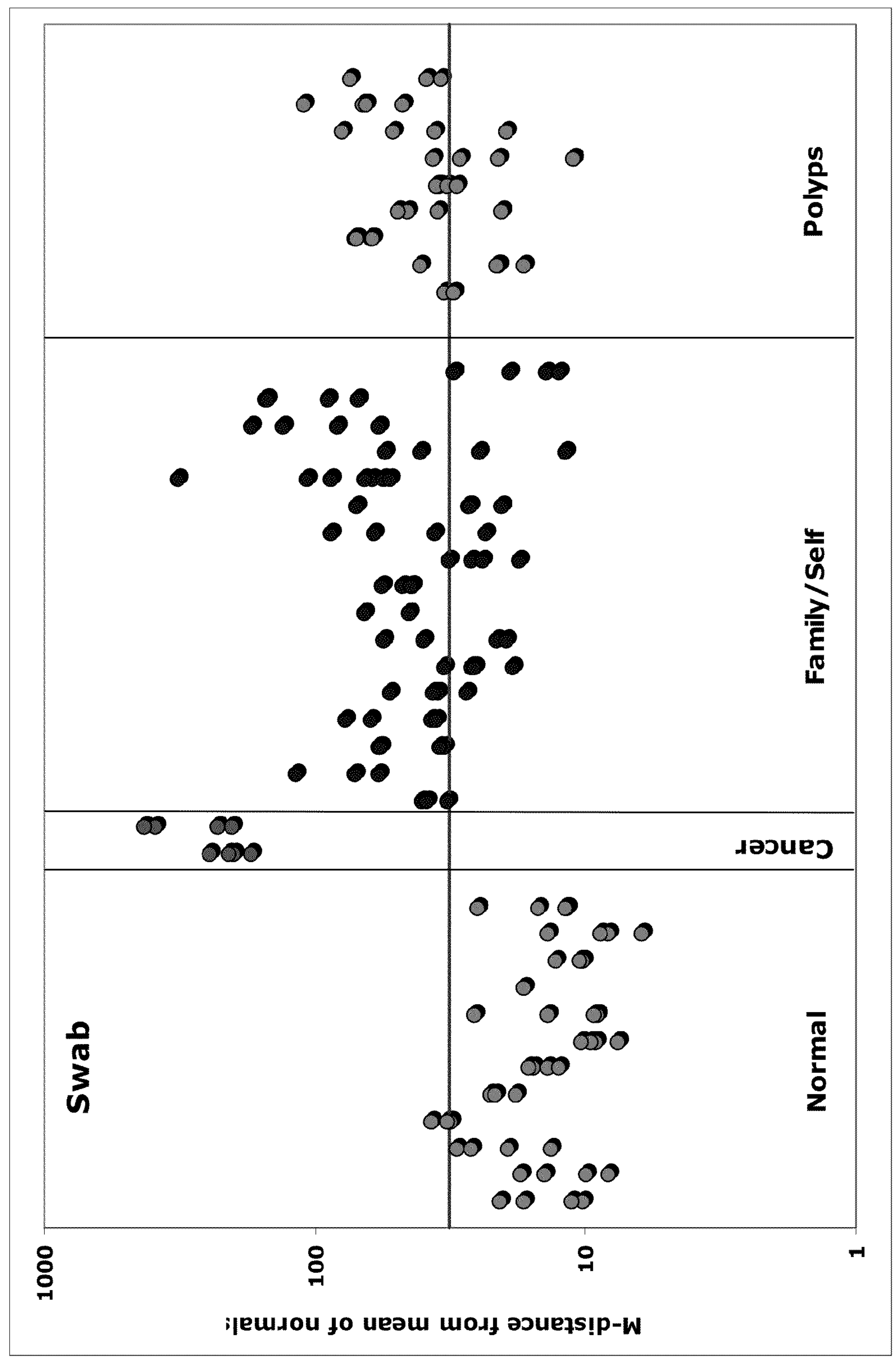

FIG. 1C shows the same analysis carried out on rectal smear samples taken from the same individuals used in the study presented in FIG. 1B. All but one normal control biopsy were at or below the 95th percentile. 15/17 (88%) individuals with family/self history had at least one M-dist value above the 95th percentile, and 13/17 (76.5%) had at least two values above it. All 9 individuals with polyps had at least one value above the 95th percentile, and 5/9 (56%) had at least two values above this criterion. In addition, all smear taken from known colon cancer from two individuals had M-dist values far above the 95th percentile.

Figure 2A:
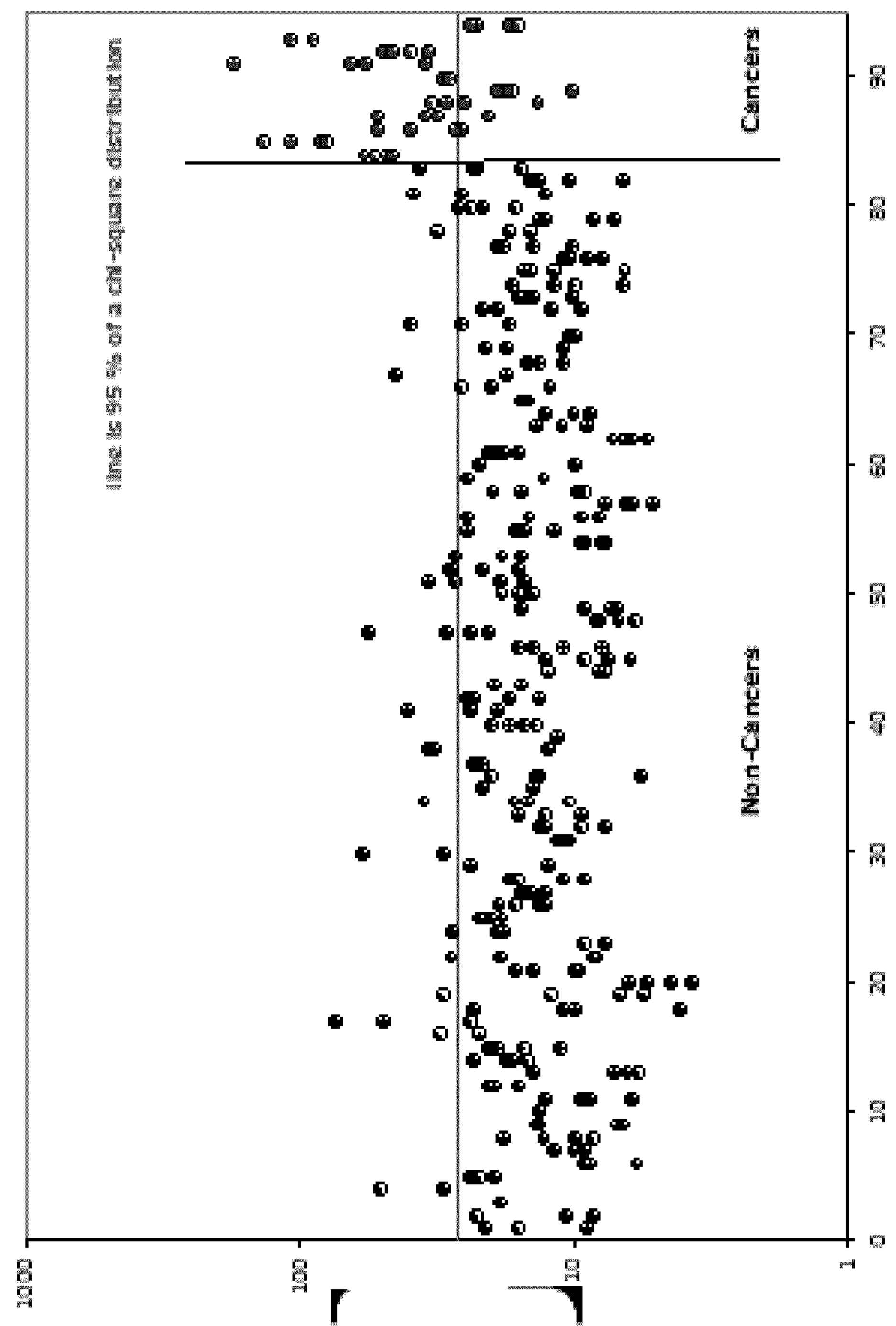
FIGS. 2A and B shows swab data. (A) shows a 90 patient study of gene expression values for 16 genes from each subject obtained by rectal swab, controls tend to fall below the 95% chi-square distribution line. A tendency of subjects with cancer to fall above the like can be seen at the far right. (B) shows the 95% chi-square distribution of gene analysis from buccal swabs of 21 controls and 8 cancer subjects.
Figure 2B:
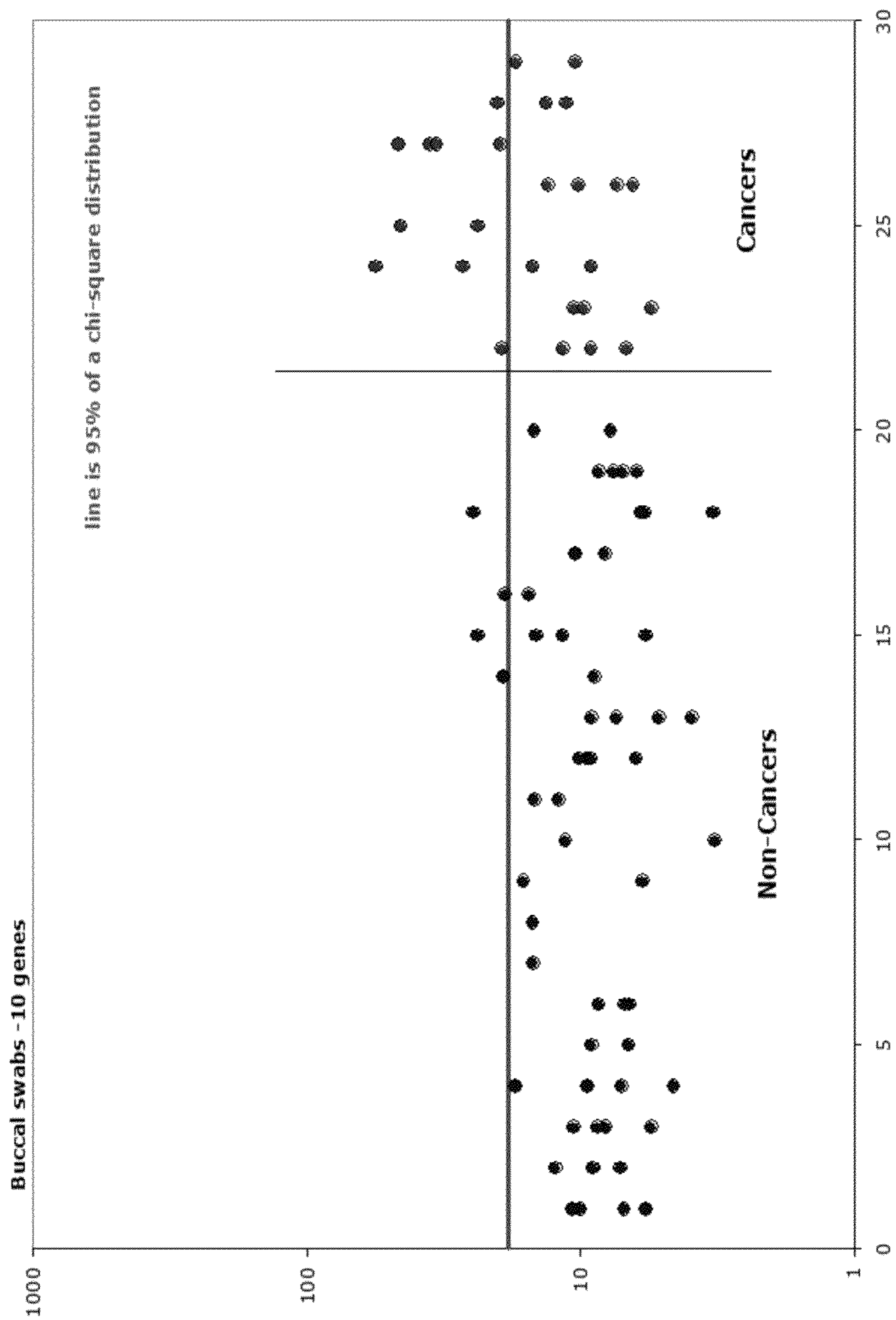

FIG. 2A-B show the similar analysis based upon a swab. FIG. 2A shows a 90 patient study of gene expression values for 16 genes from each subject, controls tend to fall below the 95% chi-square distribution line. A tendency of subjects with cancer fall above the line can be seen at the far right. FIG. 2B shows the 95% chi-square distribution of gene analysis from buccal swabs of 21 controls and 8 cancer subjects. The data demonstrate that a buccal swab and analysis of a panel of genes in the sample can be used to identify subject with a gene expression profile different than that a normal control. The difference being indicative of a risk factor for colorectal cancer.

Colon cancer is the result of a progression of molecular and cellular changes in the mucosal tissue lining the colon. While these changes are not completely understood, they are accompanied by alterations in the expression levels of many genes. Taking advantage of this fact, we have previously shown that normal appearing colon mucosa from individuals with polyps, family/self history of cancer has a different expression profile. The tissue samples from these studies were obtained by colonoscopy, but here we have shown that samples can also be obtained by rectal smear, a non-invasive procedure that can be carried out quickly and cheaply in any physician's office, without bowel preparation or anesthesia.

These results indicate that one can identify all cases of colon cancer and distinguish a high % of individuals with adenomatous polyps from those without polyps. Individuals at risk for cancer can be recommended for colonoscopies, while those with no risk may choose to avoid this costly and invasive procedure.

A number of embodiments have been described. Nevertheless, it will be understood that various modifications may be made without departing from the spirit and scope of the description. Accordingly, other embodiments are within the scope of the following claims.

What is claimed is:

1. A method for determining if a human subject has an increased risk of having colorectal cancer comprising:

collecting a buccal swab sample of mucosal cells from the subject;

generating cDNA from RNA isolated from the buccal swab sample;

measuring a cancer biomarker panel using the cDNA, wherein the cancer biomarker panel comprises three or more biomarkers selected from the group consisting of COX1, GROα, GROγ, PPARγ, p21, and cycD;

applying the measured cancer biomarker panel from the subject against a database of measured cancer biomarker panels from control subjects, wherein the database is stored on a computer system;

determining that the subject has an increased risk of having colorectal cancer by measuring a change of at least 15% in the cancer biomarker panel relative to measured cancer biomarker panels from control subjects.

2. The method of claim 1, wherein the cancer biomarker panel was obtained by using a buccal swab in the absence of an RNA protection cocktail.

3. The method of claim 2, wherein the cancer biomarker panel comprises four or more biomarkers selected from the group consisting of COX1, GROα, GROγ, PPARγ, p21, and cycD.

4. The method of claim 3, wherein the cancer biomarker panel comprises the biomarkers for COX1, GROα, GROγ, PPARγ, and p21.

5. The method of claim 2, wherein the cancer biomarker panel further comprises one or more biomarkers selected from the group consisting of CXCR2, PPARα, cMyc, and CD44.

6. The method of claim 2, wherein the cancer biomarker panel further comprises one or more biomarkers selected from the group consisting of OPN, COX2, GROα, IL8, SAA1, and PPARδ.

7. The method of claim 1, wherein the cancer biomarker panel was obtained by using a buccal swab in the presence of an RNA protection cocktail.

8. The method of claim 7, wherein the cancer biomarker panel comprises the biomarkers for GROγ, COX1, and cycD.

9. The method of claim 7, wherein the cancer biomarker panel further comprises biomarkers for COX2 and/or IL8.

10. The method of claim 7, wherein the cancer biomarker panel further comprises one or more biomarkers selected from the group consisting of CD44, OPN, cMyc, and mCSF1.

11. The method of claim 1, wherein a subject has a risk of having or has a colorectal cancer if the cancer biomarker panel measurements show a change in expression of a cancer biomarker of at least 15% compared to a control subject population.

12. The method of claim 11, wherein the subject who has a change in expression of each of the cancer biomarkers in the panel of at least 15% compared to a control subject population, is further screened for colorectal cancer comprising:

screening for hidden blood in a stool by using a fecal occult blood test (FOBT), and/or screening for signs of cancerous growth or lesions by using a proctoscopy examination.

13. The method of claim 1, wherein measuring a cancer biomarker panel is carried out by using an array comprising oligonucleotides that comprises the biomarkers for COX1, GROα, GROγ, PPARγ, P21, and cycD.

14. The method of claim 13, wherein the array further comprises one or more biomarkers selected the groups consisting of CXCR2, PPARα, cMyc, CD44, COX2, IL8, OPN, SAA1, PPARδ, and mCSF1.

15. The method of claim 13, wherein the array further comprises the biomarkers for CXCR2, PPARα, cMyc, CD44, COX2, IL8, OPN, SAA1, PPARδ, and mCSF1.

16. The method of claim 1, wherein the cDNA generated from the sample is fluorescently labeled, and wherein measuring the cancer biomarker panel comprises quantitating the fluorescence of the one or more biomarkers using a spectrofluorimeter.

17. The method of claim 1, wherein the subject has a risk of having or has a colorectal cancer if the cancer biomarker panel measurements have a Mahalanobis (M-dist) for the three or more biomarkers which exceed the $95^{th}$ percentile from pooled control values.

18. A method for determining if a human subject has an increased risk of having colorectal cancer comprising:

obtaining a buccal swab of mucosal cells from the subject;

isolating RNA from the mucosal cells;

generating cDNA from the isolated RNA;

measuring a cancer biomarker panel from the generated cDNA, wherein the cancer biomarker panel comprises three or more biomarkers selected from the group consisting of COX1, GROα, GROγ, PPARγ, p21, and cycD;

applying the measured cancer biomarker panel from the subject against a database of measured cancer biomarker panels from control subjects, wherein the database is stored on a computer system;

determining that the subject has an increased risk of having colorectal cancer by measuring a change of at least 15% in the cancer biomarker panel relative to measured cancer biomarker panels from control subjects.

* * * * *